US007259217B2

(12) United States Patent
Klaerner et al.

(10) Patent No.: US 7,259,217 B2
(45) Date of Patent: Aug. 21, 2007

(54) CONTROLLED-ARCHITECTURE POLYMERS AND USE THEREOF AS SEPARATION MEDIA

(75) Inventors: Gerrit Klaerner, San Jose, CA (US); Miroslav Petro, San Jose, CA (US); Dominique Charmot, Campbell, CA (US); Didier Benoit, Santa Clara, CA (US)

(73) Assignee: Symyx Technologies, Inc., Sunnyvale, CA (US)

( * ) Notice: Subject to any disclaimer, the term of this patent is extended or adjusted under 35 U.S.C. 154(b) by 347 days.

(21) Appl. No.: 10/775,672

(22) Filed: Feb. 10, 2004

(65) Prior Publication Data

US 2006/0128917 A1  Jun. 15, 2006

Related U.S. Application Data

(63) Continuation of application No. 09/630,328, filed on Jul. 31, 2000, now Pat. No. 6,716,948.

(60) Provisional application No. 60/146,936, filed on Jul. 31, 1999.

(51) Int. Cl.
*C08F 120/54* (2006.01)

(52) U.S. Cl. .................. 526/303.1; 526/209; 526/210; 526/217; 526/222; 526/236; 524/555

(58) Field of Classification Search ................ 526/209, 526/210, 217, 222, 236, 303.1; 524/555
See application file for complete search history.

(56) References Cited

U.S. PATENT DOCUMENTS

| 3,422,144 A | 1/1969 | Hoffmann et al. ........... 260/570 |
| 4,093,586 A | 6/1978 | Stephen ...................... 260/45.8 |
| 4,581,429 A | 4/1986 | Solomon et al. ............. 526/220 |
| 4,783,508 A | 11/1988 | Moore et al. ................ 525/310 |
| 4,792,593 A | 12/1988 | Schulz et al. ............... 526/240 |
| 5,126,021 A | 6/1992 | Grossman ................ 204/180.1 |
| 5,264,101 A | 11/1993 | Demorest et al. ........ 204/299 R |
| 5,270,271 A | 12/1993 | Lundin et al. ................. 502/8 |
| 5,290,418 A | 3/1994 | Menchen et al. ........ 204/299 R |
| 5,322,912 A | 6/1994 | Georges et al. ............. 526/204 |
| 5,346,545 A | 9/1994 | Chassot ....................... 106/410 |
| 5,374,527 A | 12/1994 | Grossman ...................... 435/6 |
| 5,374,729 A | 12/1994 | Galbo ......................... 546/242 |
| 5,385,996 A | 1/1995 | Rizzardo et al. ............. 526/240 |
| 5,389,141 A | 2/1995 | Chassot ....................... 106/498 |
| 5,401,804 A | 3/1995 | Georges et al. ............. 525/267 |
| 5,468,365 A | 11/1995 | Menchen et al. ........ 204/299 R |
| 5,498,679 A | 3/1996 | Moffat et al. ................ 526/204 |
| 5,504,243 A | 4/1996 | Sakamoto et al. ........... 560/205 |
| 5,552,028 A | 9/1996 | Madabhushi et al. ....... 204/451 |
| 5,567,292 A | 10/1996 | Madabhushi et al. ....... 204/451 |
| 5,582,960 A | 12/1996 | Nielsen et al. .............. 430/508 |
| 5,631,337 A | 5/1997 | Sassi et al. ............... 526/307.2 |
| 5,633,129 A | 5/1997 | Karger et al. .................. 435/6 |
| 5,652,289 A | 7/1997 | Eisenhart et al. ........... 524/376 |
| 5,698,648 A | 12/1997 | Rizzardo et al. ............. 526/232 |
| 5,711,767 A | 1/1998 | Gande et al. .................. 44/423 |
| 5,728,747 A | 3/1998 | Kazmaier et al. ............. 522/11 |
| 5,759,369 A | 6/1998 | Menchen et al. ........... 204/456 |
| 5,804,619 A | 9/1998 | Nicol et al. ................... 524/68 |
| 5,830,966 A | 11/1998 | Thang et al. ................ 526/321 |
| 5,844,025 A | 12/1998 | Cunkle et al. ................ 524/99 |
| 5,852,118 A | 12/1998 | Horrion et al. ............... 525/90 |
| 5,874,511 A | 2/1999 | Rizzardo et al. ............. 526/286 |
| 5,877,344 A | 3/1999 | Gande et al. ................ 560/205 |
| 5,883,211 A | 3/1999 | Sassi et al. ............... 526/307.2 |
| 5,885,432 A | 3/1999 | Hooper et al. .............. 204/469 |
| 5,919,861 A | 7/1999 | Kazmaier et al. ............. 525/26 |
| 5,919,871 A | 7/1999 | Nicol et al. .................. 525/333 |
| 6,001,232 A | 12/1999 | Chu et al. .................... 204/455 |
| 6,124,396 A * | 9/2000 | Hahn et al. .................. 524/801 |
| 6,177,540 B1 * | 1/2001 | Harlan et al. ................ 528/364 |
| 6,201,099 B1 * | 3/2001 | Petersen et al. ............. 528/376 |

FOREIGN PATENT DOCUMENTS

| EP | 0 135 280 A2 | 3/1985 |
| EP | 0 545 184 | 6/1993 |
| EP | 0 887 362 A1 | 12/1996 |
| EP | 0 891 986 A1 | 1/1999 |
| EP | 0 891 997 A1 | 1/1999 |
| EP | 0 970 973 A1 | 1/2000 |
| GB | 1 218 456 | 1/1971 |
| JP | 08-269891 | * 10/1996 |
| WO | WO96/24620 | 8/1996 |
| WO | WO97/36944 | 10/1997 |
| WO | WO97/46593 | 12/1997 |
| WO | WO98/01478 | 1/1998 |
| WO | WO98/07758 | 2/1998 |
| WO | WO98/13392 | 4/1998 |
| WO | WO98/20050 | 5/1998 |
| WO | WO98/30601 | 7/1998 |
| WO | WO98/58974 | 12/1998 |

(Continued)

OTHER PUBLICATIONS

Fanood et al. Iranian Polymer Journal (1998), 7(1), 59-65.*

(Continued)

*Primary Examiner*—Helen L Pezzuto

(57) ABSTRACT

Controlled architecture polymers made preferably with acrylamide type monomers are prepared in living-type or semi-living-type free radical polymerizations, with the architecture preferably being other than linear, such as star, branched, grafted or hyper-branched. The controlled architecture polymers have high weight average molecular weights and low viscosities, which make they particularly useful in replaceable capillary electrophoresis separation media for biological molecules, such as DNA fragments.

20 Claims, 15 Drawing Sheets

FOREIGN PATENT DOCUMENTS

| | | |
|---|---|---|
| WO | WO99/00426 | 1/1999 |
| WO | WO99/03894 | 1/1999 |
| WO | WO99/46261 | 9/1999 |
| WO | WO 00/42423 | 7/2000 |
| WO | WO 00/75207 | 12/2000 |
| WO | WO 02/090409 | 11/2002 |

OTHER PUBLICATIONS

B. L. Carvalho and E.L Thomas, *Phys. Rev. Lett.*, 1994, 73, pp. 3321-3324.

Barron, Annelise E., et al., "A Transient Entanglement Coupling Mechanism for DNA Separation by Capillary Electrophoresis in Ultradilute Polymer Solutions," *Electrophoresis*, 1994, 15, 597-615.

Barron, Annelise E., et al., "Capillary Electrophoresis of DNA in Uncross-Linked Polymer Solutions," *Journal of Chromatography A*. 652 (1993) 3-16.

Barron, Annelise E., et al., "DNA Separations by Slab Gel and Capillary Electrophoresis: Theory and Practice," *Separation and Purification Methods*, 24(1), 1-118 (1995).

Benoit et al. "Controlling Free-Radical Polymerization in the Presence of a Novel Asymmetric Nitroxyl Radical," Polymer Preprints, 38 (1), pp. 729-730, (1997).

Benoit, Didier, et al., "Development of a Universal Alkoxyamine for "Living" Free Radial Polymerizations," *J. Am. Chem. Soc.*, 1999, 121, 3904-3920.

Hawker et al., (*J. Polym. Sci. Part A: Pol. Chem.* 1998, 36, 2161-2167.

Chiari, Marcella, et al., "Separation of Oligonucleotides and DNA Fragments by Capillary Electrophoresis in Dynamically and Permanently Coated Capillaries, Using a Copolymer of Acrylamide and β-D-Glucopyranoside as a New Low Viscosity Matrix with High Sieving Capacity," *Electrophoresis*, 1998, 19, 3154-3159.

Chiari, Marcella, et al., "Separations of DNA Fragments by Capillary Electrophoresis in N-substituted Polyacrylamides," Journal of Chromatography A., 781 (1997) 347-355.

Marestin, Catherine, et al., Laboratoire de Chimie et Procedes de Polymerisation, CNRS-CPE, Villeurbanne, Fr., "Direct Measurement of Oligomers Entry Rate onto Latex Particles in a Emulsion Polymerization," Macromolecules (1998), 31(5), 1686-1689.

Dondoni, et al., (*Synth. Commun.* 1994, 24, 2537-2550).

Fitch, R.M., et al., Ins. Mater. Sci., Univ. Connecticut, Storrs, Conn., "Emulsion polymerization. Kinetics of radical capture by particles," Prog. Colloid Polym. Sci. (1975), 56 1-11.

Maxwell, Ian A., et al., Sch. Chem., Univ. Sydney, Sydney, Australia, "Entry of free radicals into latex particles in emulsion polymerization," Macromolecules (1991), 24(7), 1629-40.

Heller, Christoph, Finding a Universal Low Viscosity Polymer for DNA Separation (II), *Electrophoresis*, 1998, 19, 3114-3127.

G. Coulon, D. Ausserre, and T.P. Russell, *J. Phys.* (Paris) 51, 777 (1990).

Georges et al., "The Stable Free-Radical Polymerization Process: Role of Excess Nitroxide," *Controlled Radical Polymerization* (ACS Symposium Series #685, 1998), pp. 170-179.

German, et al., "Controlled Radical Polymerization in Emulsion," *Macromolecule*, 1997, 30, 324-326.

Goetzinger, Wolfgang, et al., "Characterization of High Molecular Mass Linear Polyacrylamide Powder Prepared By Emulsion Polymerization as a Replaceable Polymer Matrix for DNA Sequencing by Capillary Electrophoresis," *Electrophoresis* 1998, 19, 242-248.

Grimaldi, et al., "Synthesis and Applications to "Living" Free Radical Polymerization of a New Class of Nitroxyl Radicals," Polymer Preprints, vol. 38, No. 1, Apr. 1997, 651-654.

Han, Futian, et al., "High-Efficiency DNA Separation by Capillary Electrophoresis in a Polymer Solution with Ultralow Viscosity," Anal. Chem. 1999, 71, 2385-2389.

Hawker et al., "Development of a New Class of Rate-Accelerating Additivies for Nitroxide-Mediated 'Living' Free Radical Polymerization," Tetrahedron, vol. 53, No. 45, pp. 15225-15236 (1997).

J.C. Roberts, et al. *Tetrahedron Lett.*, 1997, 38, 355-358.

Janzen et al., *J. Am. Chem. Soc.*, 91:16, pp. 4481-4490 (Jul. 30, 1969).

Kotake et al., "Bimodal Inclusion of Nitroxide Radicals by b-cyclodextrin in Water as Studied by Electron Spin Resonance and Electron Nuclear Double Resonance," J. Am. Chem. Soc. 1989, 111, 2066-2070.

Lansalot, M., et al., "Nitroxide-Mediated Controlled Free-Radical Emulsion Polymerization of Styrene," Am. Chem. Society, (1999) 40, 2, 317-318.

Madabhushi, R. S., "Separation of 4-Color DNA Sequencing Extension Products in Noncovalently Coated Capillaries Using Low Viscosity Polymer Solutions," *Electrophoresis*, 1998, 19, 224-230.

Marestin, C., et al., "Nitroxide Mediated Living Radical Polymerization of Styrene in Emulsion," Macromolecules (1998), 31, 12, 4041-4044.

Poehlein et al., "Characterization of Water-Soluble Oligomer in Acrylic Acit-Styrene Emulsion Copolymerization,"0 *J. Appl. Polym. Sci.*, vol. 50, pp. 2173-2183 (1993).

Prodpran et al., "Nitroxide-Mediated Living Free Radical Miniemulsion Polymerization of Styrene," Presented at 217th National Meeting, Amer. Chem. Soc., Anaheim, CA Mar. 24, 1999, 534-535.

Ruiz-Martinez, Marie C., et al., "A Sample Purification Method for Rugged and High-Performance DNA Sequencing by Capillary Electrophoresis Using Replaceable Polymer Solutions. A. Development of the Cleanup Protocol," Anal. Chem. 1998, 70, 1516-1527.

Salas-Solano, Oscar, et al., "A Sample Purification Method for Rugged and High-Performance DNA Sequencing by Capillary Electrophoresis Using Replaceable Polymer Solutions. B. Quantitative Determination of the Role of Sample Matrix Components on Sequencing Analysis," Anal. Chem. 1998, 70, 1528-1535.

Salas-Solano, Oscar, et al., "Routine DNA Sequencing of 1000 Bases in Less Than One Hour by Capillary Electrophoresis with Replaceable Linear Polyacrylamide Solutions," Ana. Chem. 1998, 70, 3996-4003.

Senoo, Masahide, et al., "Living Radical Polymerization of N,N-Dimethylacrylamide with $RuCl_2(PPh_3)_3$-Based Inititating Systems," *Macromolecules* 1999, 32, 8005-8009.

T.P. Russell, G. Coulon, V.R. Deline, and D.C. Miller, *Macromolecules* 22, 4600-6 (1989).

Ugelstad, et al., "A Kinetic Investigation of the Emulsion Polymerization of Vinyl Chloride," *J. Polymer Sci., Part C*, No. 27, pp. 49-68 (1969).

Zhou, Haihong, et al., "DNA Sequencing Up To 1300 Bases in Two Hours by Capillary Electrophoresis With Mixed Replaceable Linear Polyacrylamide Solutions," *Anal. Chem.* 2000, 72, 1045-1052.

\* cited by examiner (LINEAR)

(6-ARM STAR)

(12-ARM STAR)

(BRANCHED)

(BRANCHED)

(BRANCHED)

(CROSS-LINKED)

(BRUSH)

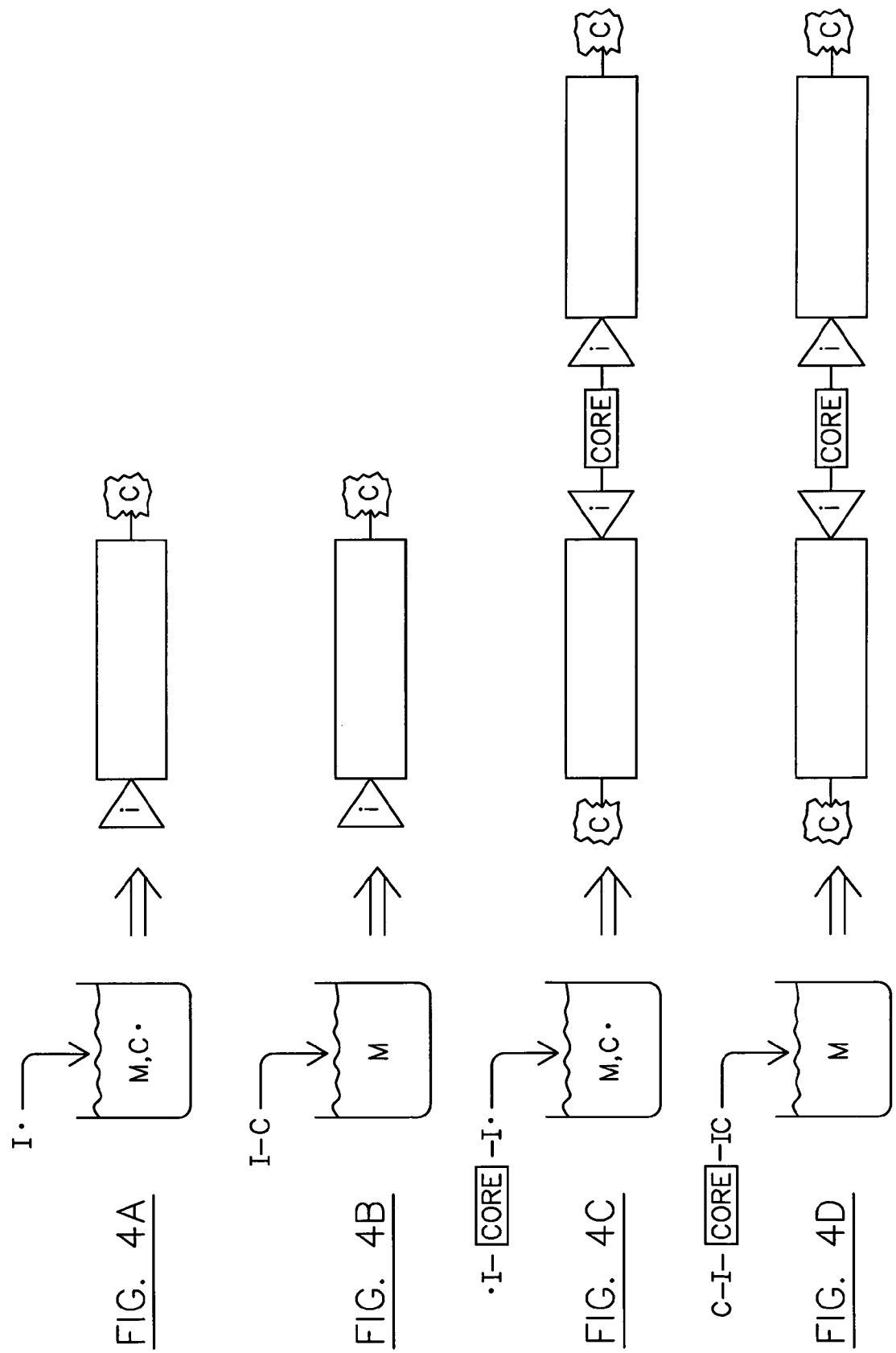

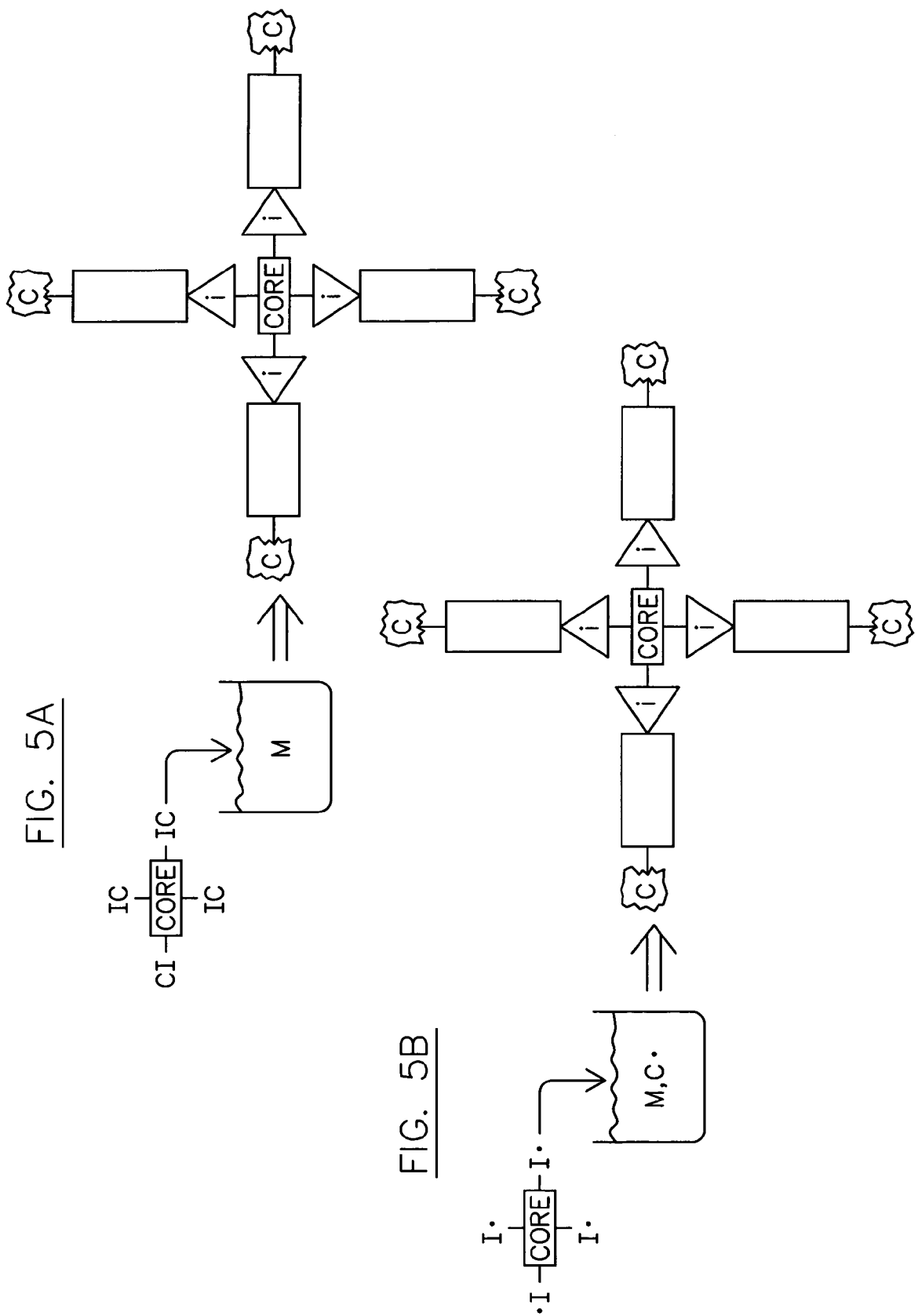

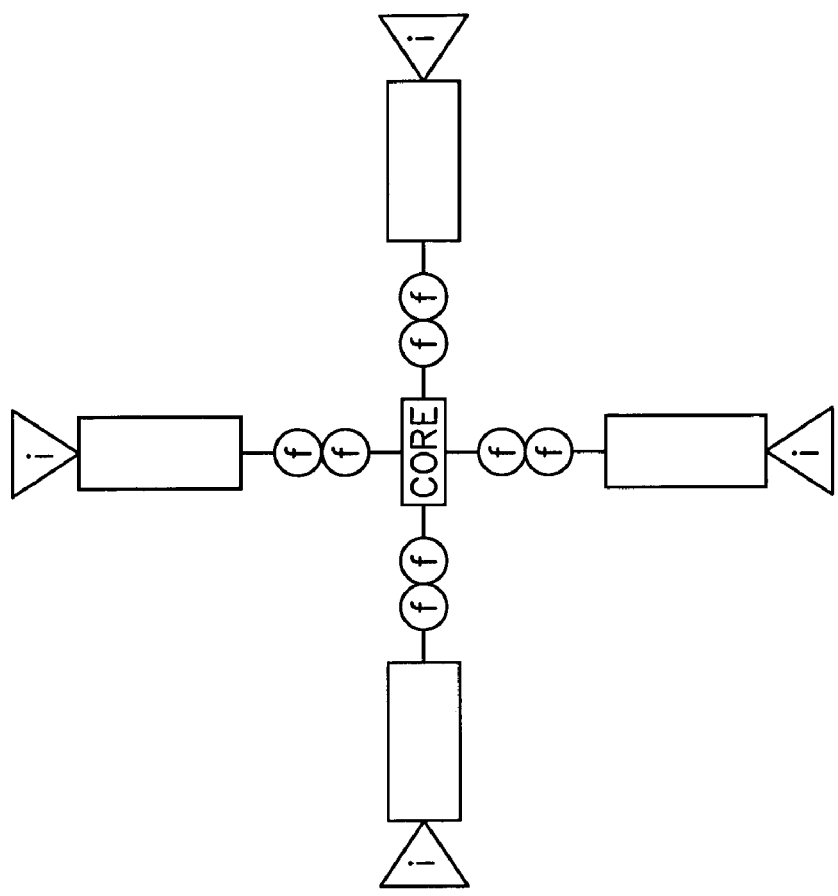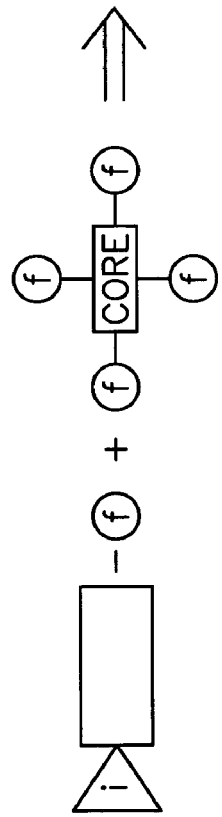
FIG. 5C

CONTROLLED-ARCHITECTURE POLYMERS AND USE THEREOF AS SEPARATION MEDIA

This application is a continuation application of application Ser. No. 09/630,328 filed Jul. 31, 2000 now issued as U.S. Pat. No. 6,716,948, which itself claims the benefit of application Ser. No. 60/146,936 filed Jul. 31, 1999.

CROSS REFERENCE TO RELATED APPLICATIONS

This application is related to the following pending, commonly assigned, U.S. patent applications, each of which is incorporated by reference in its entirety: (a) Provisional Application No. 60/123,498 entitled "Controlled Stable Free Radical Emulsion and Water-Based Polymerizations" filed Mar. 9, 1999; (b) Provisional Application No. 60/131,407 entitled "Nitroxide Mediated Free Radical Polymerizations" filed Apr. 28, 1999; (c) Ser. No. 09/347,608, entitled, "Polymerizable Compositions Containing Nitroxide Control Agents," filed Jul. 2, 1999; (d) Ser. No. 09/347,606, entitled, "Polymer Emulsions Containing Alkoxyamines," filed Jul. 2, 1999; (e) Ser. No. 09/347,607, entitled, "Block Copolymers," filed Jul. 2, 1999; and (f) Ser. No. 09/347,609, entitled, "Controlled Stable Free Radical Emulsion Polymerization Processes," filed Jul. 2, 1999.

BACKGROUND OF THE INVENTION

The present invention relates generally to polymers having controlled architectures, to controlled free-radical polymerization methods for preparing such polymers, to separation media prepared from such polymers, and to separation applications for such media. The invention relates, more specifically, to non-linear polyacrylamidic polymers having useful properties, such as controlled weight-average molecular weights, narrow polydispersity indices, flow-enabling viscosities, and water- or aqueous medium-solubility or dispersability, and to flowable separation media prepared from such polymers for use in capillary electrophoresis. The invention also specifically relates to living-type, nitroxide-mediated free-radical polymerization for preparing such polymers, as well as other polymers, in aqueous solution.

Electrophoresis and/or electroosmotic flow is a technique used for separation and analysis of charged molecules such as biopolymers (e.g., nucleic acid polymers such as DNA, RNA and amino acid polymers such as proteins). Typically, one or more samples containing molecules to be separated or analyzed are loaded onto a separation media, and a voltage is applied across the media. The applied voltage causes the charged molecules to move differentially, thereby fractionating the sample into its various components.

Gel electrophoresis typically employs a stationary, relatively flat separation media, referred to in the art as a "slab-gel", and usually comprising a highly cross-linked polymer.

Gel electrophoresis enhances separation of macromolecules by introducing a sieving effect, which helps separate such molecules according to size, and which complements separation according to electrophoretic mobilities. In capillary gel electrophoresis, a voltage is generally applied across a capillary that comprises a separation media. The separation medium can be stationary or flowing relative to the capillary. Typically, stationary separation media comprises either a crosslinked gel, a polymer solution, or other flowable media. Samples such as biomolecules are loaded or otherwise disposed onto or into stationary or flowing separation media. The applied voltage causes the biomolecules to differentially migrate, relative to the separation media, to a detector. The rate at which the biomolecule migrates depends upon a number of factors including the nature of the biomolecule, the size and weight of the biomolecule, the charge on the biomolecule, the nature and properties of the separation media, and the conditions under which the separation is performed.

Capillary electrophoretic separation approaches have been automated, but such approaches have limitations with respect to sample component resolution. Known separation media for capillary gel electrophoresis typically comprise linear molecular chains that may become entangled and thereby impart a mesh-like characteristic to the separation media. The pore-size of such an entangled mesh is dynamic such that the size and persistence time of the mesh in a linear polymer is related to both the chain length and the number of chains per unit volume. Hence, both polymer molecular weight and polymer concentration will impact the separation capabilities of the media for different sample components (e.g., different lengths of DNA). Resolution of relatively smaller sample molecules is more effective with a more closely-knit mesh—requiring lower molecular weight chains and/or higher polymer concentrations, whereas higher molecular weights are preferred for larger molecules. However, known separation media for capillary electrophoresis become unsuitably viscous when higher-molecular weight polymers and/or higher concentrations of polymer are employed in such media, sometimes referred to as replaceable media.

Overly-viscous media are generally disadvantageous in capillary electrophoresis systems due to the reduced flowability of the media, and due to the increased shear stresses between polymer molecules, and between polymer molecules and the capillary wall. In particular, shear stresses can interfere with the electrophoretic analysis and can cause polymer degradation. In addition, high viscosity may result in microbubble-spikes in the electropherogram. The relatively high viscosity of known separation media also presents a substantial barrier to improving performance and versatility in smaller scale capillary gel electrophoresis systems—particularly, for example, for micro-scale applications thereof, known in the art as microelectrophoresis systems.

The separation media for capillary electrophoresis have also been limited, heretofore, by the lack of narrow-band polymers for use in such media. Polymers typically comprise a number of different polymer molecules, each of which comprises substantially the same type of repeat unit(s) but which can vary in the number of repeat units (i.e., chain length). The polydispersity index—the ratio of the weight-average molecular weight to the number-average molecular weight for the polymer ($M_w/M_n$), is a measure of the homogeneity of the polymer with respect to hydrodynamic volume, and therefore, for linear polymers, with respect to chain-length. The state-of-the-art separation media for capillary gel electrophoresis comprise polymers having a polydispersity index greater than two, and typically ranging from about 3 to about 4. Moreover, the use of polymers with relatively high polydispersity indices limits the degree of flexibility available for formulating separation media—particularly for applications such as capillary gel electrophoresis where viscosity constraints apply.

Although present commercial capillary gel electrophoresis separation media comprise linear polymers, non-linear, star-shaped block copolymers have also been contemplated for use in such separation media. Specifically, U.S. Pat. No. 5,290,418, No. U.S. Pat No. 5,759,369 and U.S. Pat. No. 5,468,365 to Menchen et al. report lower molecular weight star-copolymers having arms comprising alternating, regularly repeating, hydrophobic segments (e.g., fluorinated hydrocarbons) and hydrophilic segments (e.g.; polyethylene oxide). A sieving effect is apparently achieved based on association between the hydrophobic regions of polymer segments—forming a physical, non-covalent cross-link. The attachment polymerization methods employed by Menchen et al., however, lead to polymers that are polydisperse, are limited with respect to yields for attaching long polymer chains onto a common central core (e.g., are of low molecular weight), and are constrained with respect to the choice of monomer.

Hence, there remains a need in the art for improved polymeric materials suitable for use in connection with capillary gel electrophoresis.

Living-type free-radical polymerization is generally known in the art. Mediation of such free-radical polymerization using nitroxide free-radical control agents is also known for some applications.

SUMMARY OF THE INVENTION

It is, therefore, an object of the invention to provide separation media having improved separation capabilities. It is also an object of the invention to provide controlled-architecture polymers having useful properties. It is likewise an object of the invention to demonstrate controlled free-radical polymerization in aqueous solutions and in bulk.

In particular, it is a feature of this invention that low viscosity polymers, yet of high molecular weight, are provided. Due to the surprising relationship between the molecular weight of the polymer in the separation media and the ability of the separation media to separate increasing numbers of base pairs, high molecular weight polymers are particularly desirable. This invention thus meets the particular requirements for separation media for biological molecule separation. This invention preferably provides non-linear, controlled architecture polymers that have high molecular weights, but sufficiently low viscosity such that the polymers can be incorporated into separation media in higher concentrations than previously practical.

Briefly, therefore, the present invention is directed to polymers, the preparation of polymers, blends of polymers, separation media, the preparation of separation media, capillary gel electrophoresis apparatus comprising such media, and analysis of samples by capillary gel electrophoresis, as described and set forth herein.

The controlled-architecture polymers of the present invention can be employed to prepare improved separation media for capillary gel electrophoresis. In particular, these polymers provide a substantial degree of flexibility for separation media formulation—particularly with respect to molecular weight, viscosity, polydispersity index and polymer loading (i.e., weight concentration), among other important properties. As such, it is now possible to prepare separation media suitable for separation and/or analyses of samples having broadly varying component characteristics. It is likewise possible to prepare tailored separation media for more specific separations and/or analyses of particular samples of interest. In addition, performance characteristics, such as sample throughput, resolution and peak capacity can be significantly enhanced. Moreover, the substantially reduced viscosity of the controlled architecture polymers of the invention offer substantial advantages for applications such as separation media for capillary gel electrophoresis— particularly for micro-scale applications thereof (i.e., micro-electrophoresis).

Other features, objects and advantages of the present invention will be in part apparent to those skilled in art and in part pointed out hereinafter. All references cited in the instant specification are incorporated by reference for all purposes. Moreover, as the patent and non-patent literature relating to the subject matter disclosed and/or claimed herein is substantial, many relevant references are available to a skilled artisan that will provide further instruction with respect to such subject matter.

BRIEF DESCRIPTION OF THE DRAWINGS

FIG. 3A shows modification of the initiator; FIG. 3B shows synthesis of the macromonomers; and FIG. 3C shows two paths for incorporation of the macromonomers.

FIGS. 4A through 4D are schematic representations of various schemes for preparing linear polymers. In these figures, "I." represents a free radical initiator, M represents monomer, "C." represents a stable free radical control agent, "I-C" or "C-I" represent an initiator-control agent adduct, "CORE" represents a poly-functional core molecule, "i" represents a free-radical initiator fragment (i.e., initiation site), the "C" within squiggly lines represents a "living" control agent end-group of a polymer chain, and the rectangular boxes represent linear chains or segments of polymer. FIG. 4A shows adding a free radical initiator into a polymerization solution that includes a monomer and a stable free radical control agent. FIG. 4B shows adding an initiator-control agent adduct into a polymerization solution that includes a monomer. FIG. 4C shows adding a bi-functional free radical initiator into a polymerization solution that includes a monomer and a stable free radical control agent. FIG. 4D shows adding a bi-functional initiator-control agent adduct into a polymerization solution that includes a monomer.

FIGS. 5A through 5C are schematic representations of various schemes for preparing star polymers. In these figures, "I." represents a free radical initiator, M represents monomer, "C." represents a stable free radical control agent, "I-C" or "C-I" represent an initiator-control agent adduct, "f" represents a functional group, "CORE" represents a polyfunctional core molecule, "i" represents a free-radical initiator fragment (i.e., initiation site), the "C" within squiggly lines represents a "living" control agent end-group of a polymer chain, and the rectangular boxes represent linear chains or segments of polymer. FIG. 5A shows adding a tetra-functional initiator-control agent adduct into a polymerization solution that includes a monomer. FIG. 5B shows adding a tetra-functional initiator into a polymerization solution that includes a monomer and a control agent. FIG. 5C shows a less preferred process of adding a tetra-functionalized core to a functionalized polymer or oligomer that has been formed via free radical polymerization.

FIG. 6A shows adding a polymer or polymer segment having free radical initiators incorporated into the backbone of the polymer or polymer segment into a polymer solution having monomer and a control agent to form a branched polymer. FIG. 6B shows a less preferred process of adding a polymer or polymer fragment having functional sites in the backbone to a functionalized polymer or oligomer that has been formed via free radical polymerization. FIG. 6C shows adding a free radical initiator to a polymer solution that includes monomer, a control agent and a second monomer that includes an initiator fragment to form a branched polymer where the branches are derived from the second monomer. FIG. 6D shows a hyper-branching schematic where monomers having initiators and/or initiator-control agent adducts attached to them are polymerized forming hyper-branched polymers.

DETAILED DESCRIPTION

Figure 1A:
FIGS. 1A through 1H are sketches showing various controlled-architecture polymers, including linear polymers (FIG. 1A), six-arm and twelve-arm star polymers (FIGS. 1B and 1C), various branched polymers (FIGS. 1D, 1E and 1F), cross-linked polymers (FIG. 1G) and brush polymers (FIG. 1H).
Figure 1B:
Figure 1C:
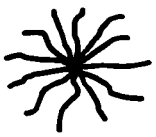
Figure 1D:
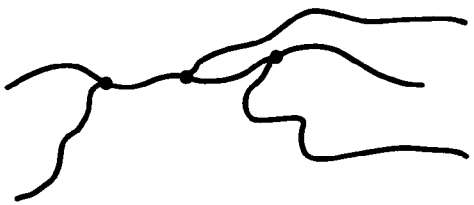
Figure 1E:
Figure 1F:
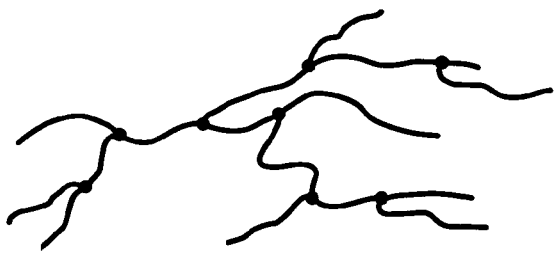
Figure 1G:
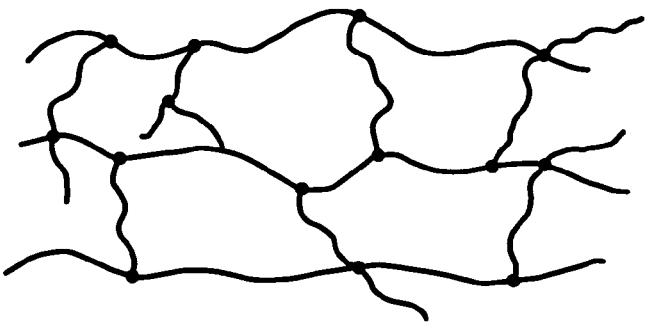
Figure 1H:

According to the present invention, controlled-architecture polymers comprising polyacrylimidic repeat units have properties that are advantageous for separation systems, and especially for electrophoretic separation systems such as capillary gel electrophoresis. In specific preferred embodiments, the polymers of the invention have controlled molecular weights, narrow polydispersity indices, flow-enabling viscosities, and/or water- or aqueous media-solubility or dispersability, among other desirably properties. Separation media comprising such polymers, individually or as blends, can be tailored for a particular separation objective of interest. Moreover, separation media of low viscosity, but suitable resolution, can be advantageously applied to increase the read-length for biological polymer samples (e.g., DNA), to improve the sample throughput, to reduce the dimensions of the capillary gel electrophoresis systems and/or to improve heat-transfer.

The polymers of the invention can, in the general case, be linear or non-linear, and can be homopolymers or copolymers. The non-linear polymers of the invention can have a number of architectures, including for example star-polymers, branched polymers, graft polymers, semi-cross-linked polymers, and combinations thereof, among others. These various polymer architectures are achieved with a high degree of control by the polymer preparation methods of the invention. Some of these methods—particularly, those directed to the preparation of polymers in aqueous solution or in bulk by the addition of monomer to a polyfunctional core molecule—also have applications with other repeat units (in addition to polyacrylamidic repeat units). These and other aspects of the invention are described in greater detail below. While the polymers are advantageously applied for use in separation media as detailed herein, other applications are also contemplated (e.g., rheology control, thermosets).

Definitions

As used herein, the phrase "characterized by the formula" is not intended to be limiting and is used in the same way that "comprising" is commonly used. The term "independently selected" is used herein to indicate that the R groups, e.g., $R^1$, $R^2$ and $R^3$ can be identical or different (e.g. $R^1$, $R^2$ and $R^3$ may all be substituted alkyls or $R^1$ and $R^2$ may be a substituted alkyl and $R^3$ may be an aryl, etc.). A named R group will generally have the structure that is recognized in the art as corresponding to R groups having that name. For the purposes of illustration, representative R groups as enumerated above are defined herein. These definitions are intended to supplement and illustrate, not preclude, the definitions known to those of skill in the art.

The term "alkyl" is used herein to refer to a branched or unbranched, saturated or unsaturated acyclic hydrocarbon radical. Suitable alkyl radicals include, for example, methyl, ethyl, n-propyl, isopropyl, propenyl (or allyl), hexyl, vinyl, n-butyl, tert-butyl, iso-butyl (or 2-methylpropyl), etc. In particular embodiments, alkyls have between 1 and 200 carbon atoms, between 1 and 50 carbon atoms or between 1 and 20 carbon atoms.

"Substituted alkyl" refers to an alkyl as just described in which one or more hydrogen atom to any carbon of the alkyl is replaced by another group such as a halogen, aryl, substituted aryl, cycloalkyl, substituted cycloalkyl, and combinations thereof. Suitable substituted alkyls include, for example, benzyl, trifluoromethyl and the like.

The term "heteroalkyl" refers to an alkyl as described above in which one or more carbon atoms of the alkyl is replaced by a heteroatom selected from the group consisting of N, O, P, B, S, Si, Se and Ge. The bond between the carbon atom and the heteroatom may be saturated or unsaturated. Thus, an alkyl substituted with a heterocycloalkyl, substituted heterocycloalkyl, heteroaryl, substituted heteroaryl, alkoxy, aryloxy, boryl, phosphino, amino, silyl, thio, or seleno is within the scope of the term heteroalkyl. Suitable heteroalkyls include cyano, benzoyl, 2-pyridyl, 2-furyl, $Me_3SiOCH_2(CH_3)_2C—$ and the like.

The term "cycloalkyl" is used herein to refer to a saturated or unsaturated cyclic non-aromatic hydrocarbon radical having a single ring or multiple condensed rings. Suitable cycloalkyl radicals include, for example, cyclopentyl, cyclohexyl, cyclooctenyl, bicyclooctyl, etc. In particular embodiments, cycloalkyls have between 3 and 200 carbon atoms, between 3 and 50 carbon atoms or between 3 and 20 carbon atoms.

"Substituted cycloalkyl" refers to cycloalkyl as just described including in which one or more hydrogen atom to any carbon of the cycloalkyl is replaced by another group such as a halogen, alkyl, substituted alkyl, aryl, substituted aryl, cycloalkyl, substituted cycloalkyl, heterocycloalkyl, substituted heterocycloalkyl, heteroaryl, substituted heteroaryl, alkoxy, aryloxy, boryl, phosphino, amino, silyl, thio, seleno and combinations thereof. Suitable substituted cycloalkyl radicals include, for example, 4-dimethylaminocyclohexyl, 4,5-dibromocyclohept-4-enyl, and the like.

The term "heterocycloalkyl" is used herein to refer to a cycloalkyl radical as described, but in which one or more or all carbon atoms of the saturated or unsaturated cyclic radical are replaced by a heteroatom such as nitrogen, phosphorus, oxygen, sulfur, silicon, germanium, selenium, or boron. Suitable heterocycloalkyls include, for example, piperazinyl, morpholinyl, tetrahydropyranyl, tetrahydrofuranyl, piperidinyl, pyrrolidinyl, oxazolinyl, and the like.

"Substituted heterocycloalkyl" refers to heterocycloalkyl as just described including in which one or more hydrogen atom to any atom of the heterocycloalkyl is replaced by another group such as a halogen, alkyl, substituted alkyl, aryl, substituted aryl, heteroaryl, substituted heteroaryl, alkoxy, aryloxy, boryl, phosphino, amino, silyl, thio, seleno and combinations thereof. Suitable substituted heterocycloalkyl radicals include, for example, N-methylpiperazinyl, 3-dimethylaminomorpholine, and the like.

The term "aryl" is used herein to refer to an aromatic substituent which may be a single aromatic ring or multiple aromatic rings which are fused together, linked covalently, or linked to a common group such as a methylene or ethylene moiety. The common linking group may also be a carbonyl as in benzophenone or oxygen as in diphenylether or nitrogen in diphenylamine. The aromatic ring(s) may include phenyl, naphthyl, biphenyl, diphenylether, diphenylamine and benzophenone among others. In particular embodiments, aryls have between 1 and 200 carbon atoms, between 1 and 50 carbon atoms or between 1 and 20 carbon atoms.

"Substituted aryl" refers to aryl as just described in which one or more hydrogen atom to any carbon is replaced by one or more functional groups such as alkyl, substituted alkyl, cycloalkyl, substituted cycloalkyl, heterocycloalkyl, substituted heterocycloalkyl, halogen, alkylhalos (e.g., $CF_3$), hydroxy, amino, phosphino, alkoxy, amino, thio and both saturated and unsaturated cyclic hydrocarbons which are fused to the aromatic ring(s), linked covalently or linked to a common group such as a methylene or ethylene moiety. The linking group may also be a carbonyl such as in cyclohexyl phenyl ketone. Specific examples of substituted aryls include perfluorophenyl, chlorophenyl, 3,5-dimethylphenyl, 2,6-diisopropylphenyl and the like.

The term "heteroaryl" as used herein refers to aromatic rings in which one or more carbon atoms of the aromatic ring(s) are replaced by a heteroatom(s) such as nitrogen, oxygen, boron, selenium, phosphorus, silicon or sulfur. Heteroaryl refers to structures that may be a single aromatic ring, multiple aromatic ring(s), or one or more aromatic rings coupled to one or more nonaromatic ring(s). In structures having multiple rings, the rings can be fused together, linked covalently, or linked to a common group such as a methylene or ethylene moiety. The common linking group may also be a carbonyl as in phenyl pyridyl ketone. As used herein, rings such as thiophene, pyridine, isoxazole, phthalimide, pyrazole, indole, furan, etc. or benzo-fused analogues of these rings are defined by the term "heteroaryl."

"Substituted heteroaryl" refers to heteroaryl as just described including in which one or more hydrogen atoms to any atom of the heteroaryl moiety is replaced by another group such as a halogen, alkyl, substituted alkyl, aryl, substituted aryl, heteroaryl, substituted heteroaryl, alkoxy, aryloxy, boryl, phosphino, amino, silyl, thio, seleno and combinations thereof. Suitable substituted heteroaryl radicals include, for example, 4-N,N-dimethylaminopyridine.

The term "alkoxy" is used herein to refer to the $—OZ^1$ radical, where $Z^1$ is selected from the group consisting of alkyl, substituted alkyl, cycloalkyl, substituted cycloalkyl, heterocylcoalkyl, substituted heterocycloalkyl, silyl groups and combinations thereof as described herein. Suitable alkoxy radicals include, for example, methoxy, ethoxy, benzyloxy, t-butoxy, etc. A related term is "aryloxy" where $Z^1$ is selected from the group consisting of aryl, substituted aryl, heteroaryl, substituted heteroaryl, and combinations thereof. Examples of suitable aryloxy radicals include phenoxy, substituted phenoxy, 2-pyridinoxy, 8-quinalinoxy and the like.

As used herein the term "silyl" refers to the $—SiZ^1Z^2Z^3$ radical, where each of $Z^1$, $Z^2$, and $Z^3$ is independently selected from the group consisting of alkyl, substituted alkyl, cycloalkyl, heterocycloalkyl, heterocyclic, aryl, substituted aryl, heteroaryl, substituted heteroaryl, alkoxy, aryloxy, amino, silyl and combinations thereof.

As used herein the term "boryl" refers to the $—BZ^1Z^2$ group, where each of $Z^1$ and $Z^2$ is independently selected from the group consisting of alkyl, substituted alkyl, cycloalkyl, heterocycloalkyl, heterocyclic, aryl, substituted aryl, heteroaryl, substituted heteroaryl, alkoxy, aryloxy, amino, silyl and combinations thereof.

As used herein, the term "phosphino" refers to the group—$PZ^n$, where each of $Z^n$ is independently selected from the group consisting of hydrogen oxygen, substituted or unsubstituted alkyl, cycloalkyl, heterocycloalkyl, heterocyclic, aryl, heteroaryl, silyl, alkoxy, aryloxy, amino and combinations thereof, where n is z to 4 depending on the phosphorus oxidation state.

The term "amino" is used herein to refer to the group—$NZ^1Z^2$, where each of $Z^1$ and $Z^2$ is independently selected from the group consisting of hydrogen; alkyl, substituted alkyl, cycloalkyl, substituted cycloalkyl, heterocycloalkyl, substituted heterocycloalkyl, aryl, substituted aryl, heteroaryl, substituted heteroaryl, alkoxy, aryloxy, silyl and combinations thereof.

The term "thio" is used herein to refer to the group —$SZ^1$, where $Z^1$ is selected from the group consisting of hydrogen; alkyl, substituted alkyl, cycloalkyl, substituted cycloalkyl, heterocycloalkyl, substituted heterocycloalkyl, aryl, substituted aryl, heteroaryl, substituted heteroaryl, alkoxy, aryloxy, silyl and combinations thereof.

The term "seleno" is used herein to refer to the group —$SeZ^1$, where $Z^1$ is selected from the group consisting of hydrogen; alkyl, substituted alkyl, cycloalkyl, substituted cycloalkyl, heterocycloalkyl, substituted heterocycloalkyl, aryl, substituted aryl, heteroaryl, substituted heteroaryl, alkoxy, aryloxy, silyl and combinations thereof.

The term "saturated" refers to lack of double and triple bonds between atoms of a radical group such as ethyl, cyclohexyl, pyrrolidinyl, and the like.

The term "unsaturated" refers to the presence one or more double and triple bonds between atoms of a radical group such as vinyl, acetylenyl, oxazolinyl, cyclohexenyl, acetyl and the like.

Controlled-Architecture Polymers

The controlled-architecture polymers of the present invention generally comprise, or alternatively consist essentially of, acrylimidic repeat units derived from monomers having the formula I:

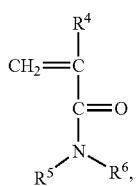

(I)

where $R^4$ is H or an alkyl group; and $R^5$ and $R^6$, independently, are selected from the group consisting of hydrogen, alkyl, substituted alkyl, cycloalkyl, substituted cycloalkyl, heteroalkyl, heterocycloalkyl, substituted heterocycloalkyl, aryl, substituted aryl, heteroaryl, substituted heteroaryl, alkoxy, aryloxy, and combinations thereof; $R^5$ and $R^6$ may be joined together in a cyclic ring structure, including heterocyclic ring structure, and that may have fused with it another saturated or aromatic ring. In preferred embodiments, the polymers comprise, or alternatively consist essentially of, the acrylamide-based repeat units derived from monomers such as acrylamide, methacrylamide, N-alkylacrylamide (e.g., N-methylacrylamide, N-tert-butylacrylamide, and N-n-butylacrylamide), N-alkylmethacrylamide (e.g., N-tert-butylmethacrylamide and N-n-butylmethacrylamide), N,N-dialkylacrylamide (e.g., N,N-dimethylacrylamide), N,N-dialkylmethacrylamide, N-methylolmethacrylamide, N-ethylolmethacrylamide, N-methylolacrylamide, N-ethylolacrylamide, and combinations thereof. In another preferred embodiment, the polymers comprise acyrlamidic repeat units derived from monomers selected from N-alkylacyrlamide, N-alkylmethacrylamide, N,N-dialkylacrylamide and N,N-dialkylmethacrylamide. Preferred repeat units can be derived, specifically, from acrylamide, methacrylamide, N,N-dimethylacrylamide, and tert-butylacrylamide. Although polymers comprising the acrylamidic repeat units as described above are generally preferred, some embodiments of the present invention (as specifically noted below) have more general application with respect to the repeat unit, and can comprise, or alternatively consist essentially of, repeat units other than the aforementiond acrylamidic repeat units.

The polymers of the invention can be homopolymers or copolymers. Homopolymers can consist essentially of any one of the aforementioned acrylamide-based repeat units. The copolymers of the invention can be random copolymers, block copolymers or graft copolymers. The copolymers can comprise, or alternatively consist essentially of, two or more of the aforementioned acrylamide-based repeat units. Copolymers of the invention can also comprise, or alternative, consist essentially of, one or more of the aforementioned polyacrylamide-based repeat units in combination with one or more other repeat units. Examples of other such repeat units include those derived from monomers suitable for forming copolymers—such as styrene, substituted styrene, alkyl acrylate, substituted alkyl acrylate, alkyl methacrylate, substituted alkyl methacrylate, acrylonitrile, methacrylonitrile, isoprene, butadiene, ethylene, vinyl acetate and combinations thereof. Functionalized versions of these monomers may also be used. Specific examples include methyl methacrylate, ethyl methacrylate, propyl methacrylate (all isomers), butyl methacrylate (all isomers), 2-ethylhexyl methacrylate, isobornyl methacrylate, methacrylic acid, benzyl methacrylate, phenyl methacrylate, methacrylonitrile, α-methylstyrene, methyl acrylate, ethyl acrylate, propyl acrylate (all isomers), butyl acrylate (all isomers), 2-ethylhexyl acrylate, isobornyl acrylate, acrylic acid, benzyl acrylate, phenyl acrylate, acrylonitrile, styrene, glycidyl methacrylate, 2-hydroxyethyl methacrylate, hydroxypropyl methacrylate (all isomers), hydroxybutyl methacrylate (all isomers), N,N-dimethylaminoethyl methacrylate, N,N-diethylaminoethyl methacrylate, triethyleneglycol methacrylate, itaconic anhydride, itaconic acid, glycidyl acrylate, 2-hydroxyethyl acrylate, hydroxypropyl acrylate (all isomers), hydroxybutyl acrylate (all isomers), N,N-dimethylaminoethyl acrylate, N,N-diethylaminoethyl acrylate, triethyleneglycol acrylate, vinyl benzoic acid (all isomers), diethylaminostyrene (all isomers), α-methylvinyl benzoic acid (all isomers), diethylamino α-methylstyrene (all isomers), p-vinylbenzene sulfonic acid, p-vinylbenzene sulfonic sodium salt, trimethoxysilylpropyl methacrylate, triethoxysilylpropyl methacrylate, tributoxysilylpropyl methacrylate, dimethoxymethylsilylpropyl methacrylate, diethoxymethylsilylpropyl methacrylate, dibutoxymethylsilylpropyl methacrylate, diisopropoxymethylsilylpropyl methacrylate, dimethoxysilylpropyl methacrylate, diethoxysilylpropyl methacrylate, dibutoxysilylpropyl methacrylate, diisopropoxysilylpropyl methacrylate, trimethoxysilylpropyl acrylate, triethoxysilylpropyl acrylate, tributoxysilylpropyl acrylate, dimethoxymethylsilylpropyl acrylate, diethoxymethylsilylpropyl acrylate, dibutoxymethylsilylpropyl acrylate, diisopropoxymethylsilylpropyl acrylate, dimethoxysilylpropyl acrylate, diethoxysilylpropyl acrylate, dibutoxysilylpropyl acrylate, diisopropoxysilylpropyl acrylate, maleic anhydride, N-phenylmaleimide, N-butylmaleimide, butadiene, isoprene, chloroprene, ethylene, vinyl acetate, 2-(2-oxo-1-imidazolidinyl)ethyl 2-methyl-2-propenoate, 1-[2-[[2-hydroxy-3-(2-propyl)]amino]ethyl]-2- imidazolidinone, N-vinyl pyrrolidone, N-vinyl imidazole, crotonic acid, vinyl sulfonic acid, and combinations thereof. Co-polymer repeat units derived from water-soluble monomers are preferred.

In some preferred embodiments, the controlled-architecture polymers of the present invention are homopolymers, random copolymers or branched copolymers. Additionally or alternatively, the polymers can consist essentially of hydrophilic repeat units, including specifically the hydrophilic acrylamide-based repeat units discussed above.

The controlled-architecture polymers of the invention can be linear or non-linear. (See, generally, for example, FIG. 1A through FIG. 1H, and Examples 2A through 2E).

Linear polymers having one or more particular properties of interest—such as a high weight-average molecular weight with a narrow polydispersity index—are especially preferred. Particularly characterized ranges for such properties for linear polymers of the invention are discussed below. In preferred embodiments, the linear polymer can comprise a central core carrying one or two initiating units (i.e., initiating fragments) and one or two polymeric arms covalently bonded to and extending from each of the initiating sites, respectively. (See, for example, Example 2C and 2D).

The non-linear polymers of the present invention can have numerous different architectures (FIG. 1B through FIG. 1H). Moreover, the architectures of the non-linear polymers can be controllably tailored to achieve specific properties of interest—typically dictated or constrained, in whole or in part, by the application for which the polymer will be used. Non-linear polymers of the present invention preferably comprise, or alternatively consist essentially of the repeat units discussed above, and can be homopolymers or copolymers as discussed above. In general, non-linear polymers comprise polymer molecules having at least one branching point—to or from another polymer molecule segment, or alternatively, to or from a central core moiety. Preferred, non-linear architectures of the polymers include, without limitiation, star-polymers and branched polymers (including, for example, graft polymers, graft-on-graft polymers, brush polymers, etc.) See FIG. 1. Combinations of such structures are also contemplated—such as branches on stars, branches on branches, stars on brush, etc. As discussed below, a degree of cross-linking is also contemplated—generally up to solubility limits for the partially cross-linked polymer.

Figure 2A:
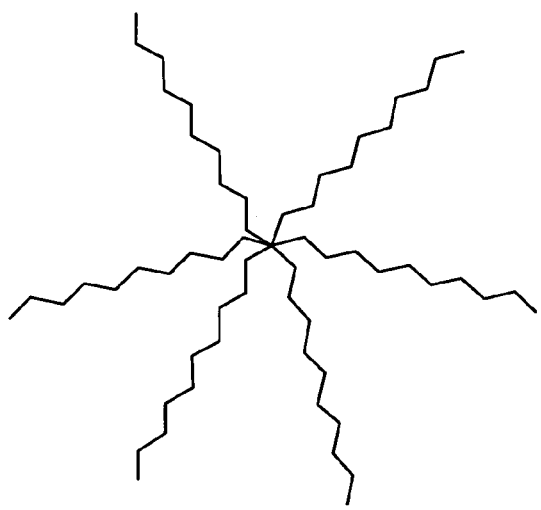
FIGS. 2A through 2E are schematic and structural representations showing six-arm (FIG. 2A) and twelve-arm (FIG. 2B) star polymers, as well as preferred two-arm (FIG. 2C), six-arm (FIG. 2D) and twelve-arm (FIG. 2E) initiator-control agent adducts.
Figure 2B:
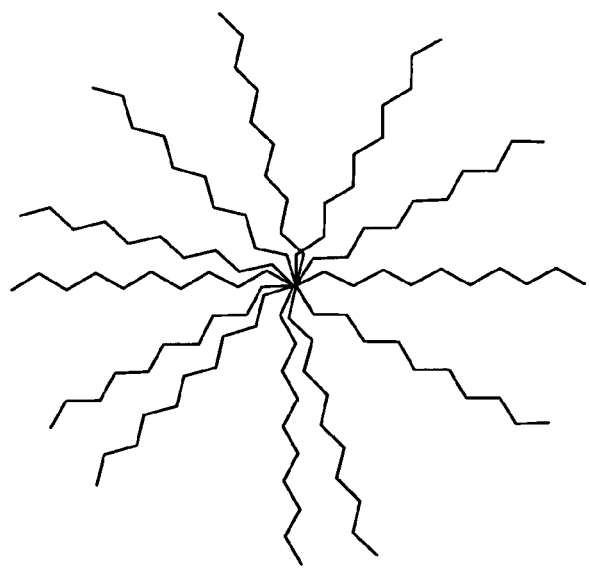

Star polymers generally comprise a central core and three or more polymeric arms covalently bonded to and extending from the core of the polymer. (See, for example, FIG. 2A and FIG. 2B).

In a preferred embodiment, the central core carries three or more initiating units, and arms covalently bonded to and extending from each of the initiating sites. It is also contemplated that the polymer can comprise functional linking groups other than an initiating unit to covalently link the arms to the core. The star-polymer core can be polymeric or non-polymeric, or combinations thereof; that is, the core itself can comprise one or more repeat units or can comprise one or more non-repeating moieties. A polymeric core can be a homopolymer or a copolymer (random, block or graft), can be an oligomer or a polymer, and can be linear or non-linear (e.g., branched or dendritic). In particular, the core can be another star polymer (e.g., with each arm of the core star polymer acting as a linker to another star). A non-polymeric core can be an organic moiety or an inorganic moiety, in either case being linked to the arms through functional groups—directly or through a linker. A preferred inorganic core can be a silica or silicon substrate functionalized to covalently carry initiator moieties (e.g., on which polymer arms can be formed to yield polymer surface brushes). Preferred core moieties, whether organic or inorganic, include initiator-functionalized cores. The size of the core moiety is not critical, and can range from very small moieties (e.g., moieties comprising only a few atoms—sufficient to provide linking to at least three arms) to larger moieties (including macroscopic substrates). Preferred organic cores for solution-phase polymerizations, however, have a core size, characterized with respect to weight-average molecular weight determined by size exclusion chromatography (under conditions detailed below), ranging from about 100 to about 500,000, and preferably from about 300 to about 300,000. Preferred inorganic cores include functionalized inorganic substrates (e.g., silica or silicon), or functionalized polymer coatings on such substrates.

The arms of star-polymers, or at least a substantial portion thereof, are polymeric, are preferably substantially polymeric in nature, and are more preferably entirely polymeric in nature—except optionally with respect to non-polymeric linkage (via intitator units, functional groups or linking moieties) to the core and/or with respect to non-polymeric linkage (via initiator units, functional groups or linking moieties) to other polymer chains (e.g., branches on star arms). The arms can be homopolymers or copolymers, and can be linear or non-linear, as generally described above (including with respect to preferred repeat units). The number of arms on the star-polymer of the invention can range from about 3 to about 100, and preferably ranges from about 3 to about 50, or from 3 to about 20, and most preferably from about 4 to about 12. Particularly preferred star-polymers include 4-arm, 6-arm and 12-arm polymers. (See, for example, Examples 2A and 2B). The chain lengths of the various arms can be substantially the same for each chain, but are typically, due to statistical probability for variation in the reactivities of the growing chains, varied somewhat. Schemes to selectively or randomly vary the arm length are also contemplated.

Branched polymers comprise polymer molecules in which there are side branches of linked monomer molecules protruding from various central branch points along the main polymer chain. (FIG.'s 1D, 1E and 1F) (See, for example, Example 2E). Hence a branched polymer molecule can comprise two or more polymeric segments covalently bonded to each other at a point other than their common ends—either directly (e.g., through functional groups on side chains thereof), or indirectly through a linking moiety. The various "branches" of branched polymers can comprise polymeric segments having substantially the same or different repeat units, and can themselves be homopolymers or copolymers. In one embodiment, branched polymers include a polymeric or non-polymeric core, as described above in connection with star polymers. The extent of branching is not narrowly critical, and can vary substantially within the scope of the invention. With respect to a particular application, however, the degree of branching can have a substantial impact. It is contemplated, for example, that the polymer molecules can comprise extensive branch on branch structures. The degree of branching is preferably less than the degree of branching that would make the resulting polymer substantially insoluble or non-dispersible in water or in the aqueous medium (as defined below in connection with the separation medium). That is, although the polymers of the invention can be extensively branched, they remain at least partially soluble or dispersible in water or in the aqueous medium, and are preferably substantially or completely soluble or dispersible in water or in the aqueous medium.

The polymer can also be a cross-linked polymer. In general, however, the polymers of the present invention are not extensively cross-linked. The degree of cross-linking for the polyarylamidic polymers of the invention is preferably less than the degree of cross-linking that would make the resulting polymer substantially insoluble or nondispersible in water or in the aqueous medium (of the separation medium). That is, although the polymers of the invention can be cross-linked to some degree, they remain at least partially soluble or dispersible in water or in the aqueous medium, and are preferably substantially or completely soluble or dispersible in water or aqueous medium.

Such partially branched and/or partially cross-linked polymers are particularly advantageous with respect to applications for separation media. Without being bound by theory, the sieving capability of the partially branched or cross-linked polymer will be enhanced relative to linear, non-cross-linked polymers having the same repeat unit, thereby providing more flexibility with respect to loadings, throughput, etc., while still providing adequate resolution. The sieving capability of such polymer will, however, be less than highly cross-linked polymers, such as employed in gel electrophoresis (i.e., "slab-gel"), but advantageously, such partially branched or cross-linked polymers are at least partially soluble or dispersible in water or in an aqueous medium.

The molecular weight of the polymers is not narrowly critical in the general case. The molecular weight is an important property of interest, however, for specific applications of the controlled-architecture polymers—such as separation media. In such applications, the molecular weight for linear or non-linear polymers is preferably at least about 75,000, more preferably at least about 100,000, and can also be at least about 150,000, at least about 200,000, at least about 300,000, at least about 500,000, at least about 1,000,000, at least about 2,000,000, at least about 5,000,000, or at least about 10,000,000 or more. For non-linear polymers of the invention, the molecular weight can, in addition to those aforementioned molecular weights, be even higher, including at least about 12,000,000, at least about 15,000,000, at least about 20,000,000 or at least about 25,000,000 or more. The molecular weight for linear polymers can generally range from about 75,000 to about 10,000,000, and preferably from about 100,000 to about 1,000,000. For non-linear polymers such as a star-polymer, the molecular weight can generally range from about 1000 to about 100,000,000, preferably from about 10,000 to about 25,000,000, and more preferably from about 100,000 to about 12,000,000. These and other more specific ranges may be preferred in particular combinations with other polymer properties, as discussed below.

Unless otherwise specifically noted, the molecular weight values recited herein are weight-average molecular weights as determined by size-exclusion chromatography (SEC), based on correlation to narrow linear polystyrene standards. For example, a SEC-observed Mw value of 100,000 means that the measured polymer has the same hydrodynamic volume as the polystyrene of the molecular weight 100,000 under the conditions used for both calibration and characterization (DMF+0.1% TFA) of all samples.

In one embodiment of the invention, the observed molecular weight of the polymer, as determined by SEC under the aforementioned conditions, is substantially less than the actual molecular weight of the polymer. Because SEC methods determine weight-average molecular weight based on the relative hydrodynamic volume of the polymer as compared to the hydrodynamic volume of a polymer standard of known molecular weight (and typically narrow polydispersity index), the observed molecular weight can vary depending on the particular architecture of the polymer. Hence, compact, high density polymer architectures, such as star-polymers, have an observed molecular weight based on SEC that is substantially less than its actual molecular weight. As shown in Examples 2A through 2E, and as consistently observed in unreported experiments, the observed Mw values obtained by SEC correlate well with the targeted molecular weight values for linear polymers; however, the observed-SEC Mw values for non-linear are typically substantially lower than the targeted Mw. Hence, these polymers have a smaller hydrodynamic volume than that of their linear counterparts of the same actual molecular weight. This deviation, and increases in this deviation with an increase in targeted arm length is consistent with the star-like architecture of the polymers.

In the general case, the observed molecular weight of the polymer as determined by SEC can be at least about 10% less than the actual molecular weight, more preferably at least about 25% less than the actual molecular weight and still more preferably at least about 50% less than the actual molecular weight. The actual molecular weight, as used herein, means the weight-average of the actual weight of polymer molecules in the polymer based on the actual atomic structure thereof. Because of the inherent difficulties in determining actual molecular weight, however, the actual molecular weight can be approximated by other suitable means. For example, for purposes of the present invention, the actual molecular weight can be approximated as the target molecular weight. The target molecular weight refers to the estimated molecular weight based on the total amount (e.g., moles) of monomer to be incorporated into polymer during the polymerization reaction, as determined by the amount (e.g., moles) of initiator, and the monomer to initiator ratio, assuming that each initiator starts one chain, and that all monomer is incorporated. In situations where initiator efficiency is 0.9 or less, and/or monomer conversion is less than 95%, then adjustments for the target molecular weight are made based on initiator efficiency and/or monomer conversion, respectively.

The polydispersity index of the polymer can generally range from about 1 to about 3, and preferably from about 1 to about 2.5. In preferred embodiments, the polydispersity index is preferably not more than about 2.0, and preferably ranges from about 1 to about 2.0. In more preferred embodiments, the polydispersity index of the polymer is preferably not more than about 1.8, more preferably not more than about 1.6, and even more preferably not more than about 1.5. The polydispersity index can be even lower, including not more than about 1.4, not more than about 1.3, not more than about 1.2, or not more than about 1.1. Hence, in preferred embodiments, the polydispersity index can range from about 1 to about 1.8, from about 1 to about 1.6, or from about 1 to about 1.5.

The viscosity of the polymer solution is not critical in the general case, but can be important in some applications—particularly in applications in which flow of the polymer is desired or required. Hence, the viscosity of the polymer should, in general, be suitable for use in the particular application at hand (e.g., capillary gel electrophoresis—discussed in greater detail in connection with separation media therefore).

The polymers are preferably water-soluble or water dispersible. More specifically, the soluble polymers are at least partially water soluble, and are preferably substantially water-soluble or completely water soluble. As used herein, the term "at least partially soluble" means that at least some amount of the compound of interest is present as a solute in a continuous phase solution medium. The dispersible polymers are preferably uniformly dispersed mixtures of solid polymer particles in a liquid, preferably aqueous, continuous phase. The size of the particles in such a dispersion is, in preferred applications, small enough to form a stable dispersion. Water-soluble and water-dispersible polymers have numerous applications and can provide numerous advantages in such applications. For polymers employed in capillary gel electrophoresis, the polymers are preferably water soluble or water dispersible as described, but can, less stringently, be soluble (at least partially soluble) or dispersible (preferably uniformly dispersible) in the aqueous-medium of the separation medium (as defined below). Capillary gel electrophoresis medium that are aqueous solutions or aqueous dispersions are preferred over non-aqueous separation medium, because they provide the necessary environment for electrophoresis (e.g. ions) and provide good solubility for most biomolecules of interest. Aqueous solutions also provide for ease of handling, low toxicity and cost-savings as compared to organic solvents.

The invention comprises a number of preferred controlled-architecture polymers—variously characterized with respect to structure and/or properties of interest, and in some embodiments, by its method of preparation. With respect to these preferred polymers, generally described as follows, it is to be understood that the aforementioned details relating to a particular property or feature of the polymer apply as well to the propoerty or feature as generally referred to below—without further mentioning of every such detail each time that reference is made to such property or feature. For example, with regard to a reference to polymers having acrylamide-based repeat units, it is to be understood that the polymer can comprise such repeat units or consist essentially of such units, that the polymer can include, collectively or individually, the various types of polyacrylamide repeat units (e.g., methacrylamide, NN-dialkylacrylamide, etc.), and that the polymer can be a homopolymer, a copolymer, a linear polymer, a non-linear polymer, etc., as described above, unless characterized in a manner that specifically includes or excludes certain additional requirements. As another example, if a polymer of an embodiment set forth as follows is described as having a molecular weight of at least about 75,000, it is to be understood that the other, specifically delineated molecular weights as described above, will likewise apply to that embodiment. Additionally, while the variously characterized polymers described as follow are suitable for and preferred for use in connection with separation media, such as capillary gel electrophoresis, the polymers as characterized are not limited to use in such applications, except to the extent specifically and positively required in the claims.

In one preferred embodiment, the polymer comprises acrylamide-based repeat units, is at least partially water—or aqueous medium-soluble or water—or aqueous medium—dispersible, has a weight-average molecular weight at least about 75,000 and has a polydispersity index of not more than about 2.0. Hence, this embodiment includes linear and non-linear polymers of higher molecular weight that have a carefully-controlled chain lengths and/or architecture—therefore providing a narrower range of hydrodynamic volume.

In another preferred embodiment, the polymer comprises acrylamide-based repeat units, is at least partially water—or aqueous medium-soluble or water—or aqueous medium—dispersible, and is non-linear. In preferred cases of this embodiment, the polymer is a homopolymer, a random copolymer or a branched copolymer. In another preferred case of this embodiment, the polymer consists essentially of hydrophilic repeat units. With regard to architecture, star-polymers are particularly preferred in connection with this embodiment.

In an additional preferred embodiment, the polymer comprises acrylamide-based repeat units, is at least partially water—or aqueous medium-soluble or water—or aqueous medium—dispersible, has a weight-average molecular weight of at least about 75,000, and has a viscosity suitable for capillary gel electrophoresis. As such, this embodiment includes linear and non-linear polymers of higher molecular weight that can be used to form a flowable separation media.

Methods for preparing the controlled-architecture polymers of the invention, as variously characterized in the above discussion, are set forth in detail below. Preferred embodiments also include polymers prepared by such methods.

Although the polymers of the present invention, including those of the immediately aforementioned preferred embodiments, are suitable for use in various applications by themselves, it is also contemplated that they can be advantageously applied in various applications as blends with each other and/or with other, unrelated polymers. Hence, a further preferred embodiment of the invention is directed to blends of two or more different polymers (defined below in connection with separation media comprising different polymers), with at least one of the polymers being a polymer of the invention, as variously characterized above. Such blends can be particularly advantageous for use in separation media formulations, and especially in media for capillary gel electrophoresis. Specifically, a composition comprising such blends of polymers can be "fine tuned" with respect to particular physical and/or chemical properties of interest for a particular application.

Also, many polymer aqueous solutions exhibit a a cloud point phenomenon, which occurs at the Low Critical Solubility Temperature (LCST), below which the polymer is soluble and the solution is clear, and beyond which the polymer is not soluble anymore and the solution is turbid or opaque. A typical way to measure the LCST of a polymer in a given solvent, in this instance water, is to record the transmitted light of the solution when increasing temperature. The LCST is not generally concentration dependent for the preferred polymers in water. The LCST is given by the onset of precipitation that translates into a drop of the transmitted light. Upon incorporating more hydrophobic monomers (such as N-isopropylacrylamide) into the polymer LCST behavior can lead to non-covalent polymer to polymer interactions. In preferred embodiments, the LCST is at least about 80° C., more preferably at least about 85° C. and even most preferably at least about 90° C.

Separation Media

The controlled-architecture polymers of the invention can be used to form a separation medium for fractional separation of samples having more than one component. When applied in connection with capillary gel electrophoresis, for example, such separation media facilitates the separation and/or analysis of a variety of biomolecules including proteins, polysaccharides and polynucleotides (i.e., nucleic acid oligomers and polymers), among others. Separation media formed from the polymers described above are particularly useful for fractionating nucleic acid polymers such as deoxyribonucleic acid (DNA) polymers. While much of the discussion and examples presented herein for the separation media are directed to capillary gel electrophoresis, use in such applications is to be considered as exemplary and non-limiting, except as required in the claims. The separation medium comprises a polymer—preferably one or more of the aforementioned polymers of the invention—and an aqueous medium.

The particular polymer (or blend of polymers) to be employed in the separation media can be selected to achieve particular desired properties of the separation medium (e.g., viscosity) as well as particularly desired capabilities (performance characteristics) of the separation media. For example, the polymer(s) of the separation media can be selected (tailored) to achieve a particular resolution, throughput or peak capacity for a particular sample or sample fraction (e.g., a polynucleotide having a specific number of base pairs).

Star-polymers of the present invention are particularly attractive for use in separation media. Without being bound by theory, the controlled-architecture star-polymers are believed to form a mesh in aqueous solution, where the central-core branching points constitute centers of concentrated mass that could resemble cross-linking points in cross-linked water-insoluble polymers (e.g., used in slab-gel applications). Moreover, for star-polymers of higher molecular weights, the arms of the polymers can also create mesh-like structures similar to those of entangled linear polymers. The particular nature of the mesh can be controlled by varying the number of arms of the star, the chain-length for arms, the composition (e.g., repeat units) of the arms, and the concentration of polymer in the separation medium. Hence, the controlled-architecture polymers of the invention offer substantial flexibility to tailor separation media for particular applications.

The aqueous medium comprises water, and preferably at least about 50% water by weight relative to total weight of the aqueous medium. The weight-percentage of water in the aqueous medium can generally range from about 50% water to about 100% water. Water can be combined with water-miscible liquids, such as methanol or other alcohols. The aqueous medium can also be a buffer or an electrolyte solution. Aqueous buffer solutions having a pH range suitable for the sample molecules of interest. For DNA separation, for example, pH can range from about 6 to about 9. For protein separation, the pH can vary over a larger range, depending on the particular protein of interest. Some proteins and other biopolymers can require relatively extreme pH conditions for separation.

The separation medium can be prepared by combining one or more polymers with the aqueous medium, and mixing to form an aqueous solution or an uniformly dispersed aqueous dispersion. As noted, the molecular weight of the polymer, the architecture of the polymer, the amount of polymer (i.e., polymer loading) and the nature of the aqueous medium can be controlled to provide the desired properties (e.g., viscosity) and/to provide the optimum analysis for a particular sample. Separation media formulated with star polymers, or with blends comprising star polymers, are particularly useful for fractionating polynucleotides by capillary electrophoretic methods.

The polymer loading in the separation media is not narrowly critical, but can be important in some cases—with respect to performance criteria (e.g., sample resolution, throughput and/or peak capacity) and/or properties of interest (e.g., viscosity, solubility, dispersibility and/or flowability). For applications directed to capillary gel electrophoresis, the polymer loading should be sufficient to provide adequate resolution for the sample fraction of interest, without adversely affecting flowability and/or other desirable properties of the separation media.

Significantly, polymer loading, in combination with other properties, especially molecular weight and viscosity of the separation medium, can be an effective control parameter for performance features (e.g., flowability, sample throughput, etc.). For capillary gel electrophoresis, for example, the high-end loading limit may be functionally constrained by viscosity, solubility and/or more generally, flowability. In general, for such applications, the separation media comprises polymer at a loading of at least about 1%, more preferably at least about 3%, and most preferably at least about 5%, in each case the percentage being by total weight of polymeric components relative to total weight of the separation media. In some embodiments, the polymer loading is preferably at least about 10%, more preferably at least about 15%, and most preferably at least about 20%, and in some cases, at least about 25%, or at least about 30%, at least about 40% or at least about 50%, in each case by total weight of polymeric components relative to total weight of the separation media. Hence, the separation media can generally comprise polymer(s) at a loading ranging from about 1% to about 50%, and preferably from about 2% to about 20% or from about 20% to about 50%, in each case the percentage being by total weight of polymeric components relative to total weight of the separation media. In some embodiments, relative low polymer loading are preferred, including for example, polymer loadings ranging from about 1% to about 10%, and preferably from about 1% to about 5%, in each case by total weight of polymeric components relative to total weight of the separation media.

The viscosity of the separation medium is preferably suitable for the application of interest, and in preferred embodiments, suitable for capillary gel electrophoresis. (See, for example, Example 2F). In particular, the viscosity of the separation medium should be controlled or adjusted such that the separation media is a flowable medium at the analysis temperature—typically about 50° C., and in some cases preferably up to about 60° C. or higher for capillary gel electrophoresis. As used herein, the term "flowable medium" means generally, a medium which can flow under a motive force (e.g., pressure head developed by a pump) through a capillary with an internal diameter or width of the system in which it will be used—typically of not more than about 100 µm. Other parameters, such as the temperature at which the separation/analysis of sample molecules is effected, polymer loading, and degree of solubility could each, independently and cumulatively, also have an effect on viscosity and/or flowability at a given polymer loading. The viscosity and, independently and cumulatively, the flowability of the separation medium are preferably suitable for capillary gel electrophoresis in a system comprising a capillary having an interior diameter or width of about 100 µm or less, preferably of about 75 µm or less, more preferably of about 50 µm or less, still more preferably of about 25 um or less, even more preferably of about 10 µm or less, and most preferably of about 5 µm or less. As such, the viscosity of the separation medium is suitable for microelectrophoretic applications. Characterized with respect to other aspects of particular importance with respect to automation, for example, the viscosity is suitable for filling, flushing and refilling the separation medium from such capillaries (e.g., for stationary separation-medium systems) and/or for flowing within the capillary (e.g., for flow or counter-flow systems) at the molecular weights and polymer loadings of interest.

More particularly, the viscosity of the separation media, based on typical conditions of 6.5% polymer loading in 8M urea and 100 mM TAPS (pH=8), as measured at 30° C. with a Brookfield viscometer is: (i) for polymers having a molecular weight of about 200,000 D, preferably no more than about 900 cP, more preferably no more than about 600 cP and most preferably no more than about 300 cP; (ii) for polymers having a molecular weight of about 150,000 D, preferably no more than about 300 cP, more preferably no more than about 200 cP and most preferably no more than about 100 cP; and (iii) for polymers having a molecular weight of about 100,000 D, preferably no more than about 50 cP, more preferably no more than about 35 cP and most preferably no more than about 20 cP. In other embodiments, for polymers having a molecular weight of about 1,000,000 D and higher (e.g., up to a molecular weight of about 12,000,000) the viscosity is preferably no more than about 900 cP, more preferably no more than about 600 cP and most preferably no more than about 300 cP. The aforementioned molecular weights are measured by gel permeation chromatography. The aforementioned ranges are particularly preferred for N,N-dimethylacrylamide polymers. As another benchmark, the viscosity of the separation media for capillary gel electrophoresis can be about 300 cP or less, based on a 10% poly N,N-dimethylacrylamide loading measured as set forth in Example 2F for a polymer having non-linear architecture and a target molecular weight of about 6,000,000. This compares favorably to literature values for polyN,N-dimethylacrylamide reported in R. S. Madabhushi, *Electrophoresis*, 19:224-230 (1998) (1200 cP for a 200,000 D polymer loaded in media at 6.5%), which is incorporated herein by reference. In another test, using a Brookfield low volume cone and plate viscometer at room temperature, star and hyperbranched poly N,N-dimethylacrylamide was compared to linear poly N,N-dimethylacrylamide with the following results: (1) a 12 arm star having a molecular weight of about 3,000,000 at a loading of 5 weight % in water had a viscosity of 230 cps; (2) a hyperbranched poly N,N-dimethylacrylamide polymer having a molecular weight of about 1,300,000 at a loading of 5 weight % in water had a viscosity of 130 cps; and (3) a linear poly N,N-dimethylacrylamlide polymer having a molecular weight of about 1,000,000 at a loading of 5 weight % in water had a viscosity of 720 cps. This demonstrates the preferred embodiments of creating high molecular weight polymers of controlled architecture that can be used at higher loading to achieve an acceptable viscosity in a replaceable separation media for capillary electrophoresis.

Significantly, separation media having low-viscosity and/or high flowability offer important commercial advantages over the present state-of the art in capillary gel electrophoresis systems. First, improved viscosity/flowability of the separation media can translate into improved robustness—capability of separating a broader range of sample molecule sizes, with suitable performance (e.g., resolution, throughput and/or peak capacity). With respect to DNA separation/analysis, such robustness is referred to in the art as "read length"—the capability to read DNA molecules of a certain length. Additionally, improved viscosity/flowability of the separation media allows for a reduction in capillary geometry—e.g., capillaries having interior diameter or widths of about 75 µm or less, of about 50 µm or less, of about 25 µm or less, of about 10 µm or less and/or of about 5 µm or less. Reduced scales with respect to the flowable-capillary geometries have other advantageous implications, such as overall system-size reduction (representing cost savings, particularly for pressure applications), alternative fabrication methods (e.g., microfabrication/microelectro-mechanical systems (MEMS), etc.), improved sample throughput, higher capillary density, and/or improved surface area to volume ratios, and therefore, improved heat transfer—ultimately allowing for increased flexibility with respect to temperature for the sample separation/analysis (particularly meaningful, with respect to DNA separation/analysis). As a further advantage, reduced viscosity/flowability allows for microelectrophoretic capillary gel electrophoresis systems to be fillable, flushable, and refillable—manually, or as particularly preferred, in an automated fashion. In addition, the microelectrophoretic capillary gel electrophoresis systems may have open or closed channels. Also, multi-channel capillary electrophoresis apparatus that use sheet-flow detection (such as those made by PE Biosystems) may tolerate viscosities of up to only 600 cps, making lower viscosity polymeric separation media commercially significant.

Another property of some concern for use of a separation media in capillary gel electrophoresis relates to reducing sample molecule interactions (especially DNA) with the interior surface of the capillary wall. In general, the interactions are minimized with a polymer having an appropriate degree of hydrophilicity, among other factors known in the art. A preferred polymer, in this regard, is N,N-dimethylacrylamide. Thus, with proper selection of the monomers used in the polymers, the polymers can coat the walls of otherwise "un-coated" fused silica capillaries. This wall coating may be a dynamic wall coating, suppressing both interactions of the wall with the sample and electroosmotic flow.

In addition, optical properties of the separation medium should not interfere with the detection mechanism for the electrophoresis—which are typically optical in nature. In general, polyacrylamides of the invention are accepted in the art as being suitable—particularly for fluorescence-based detection.

Preferred embodiments of the separation media are discussed as follows. With respect to these preferred separation media, it is to be understood that the aforementioned details relating to a particular property or feature of the polymer, or of the separation media apply as well to the property or feature as generally referred to below—without further mentioning of every such detail each time that reference is made to such property or feature.

In one separation media, one or more polymer(s) comprise acrylamide-based repeat units (as described above), are at least partially soluble in water or aqueous medium, or dispersible in water or aqueous medium and have a weight-average molecular weight greater than about 75,000. Such polymers are combined with (e.g., solubilized or dispersed in) an aqueous medium to form a solution with a (total) polymer concentration of at least about 20%, by weight, relative to the total weight of the medium, and a viscosity suitable for capillary gel electrophoresis.

Another preferred separation media includes one or more polymer(s), at least one of which comprises acrylamide-based repeat units (as described above), is at least partially soluble in water or aqueous medium, or dispersible in water or aqueous medium, and is non-linear. Such polymer(s) are combined with (e.g., solubilized or dispersed in) an aqueous medium to form a solution with a viscosity suitable for capillary gel electrophoresis. The non-linear polymers are preferably star-polymers.

In yet another preferred embodiment of the invention, the separation media comprises one or more polymer(s), at least one of which comprises acrylamide-based repeat units (as described above), and is at least partially soluble in water or aqueous medium, or dispersible in water or aqueous medium, and is non-linear. Such polymer(s) are combined with (e.g., solubilized or dispersed in) an aqueous medium to form a solution having a low polymer loading—preferably less than about 10%, and in some cases less than 5% by total weight of polymer relative to total weight of the separation medium—and with a viscosity suitable for capillary gel electrophoresis. For such non-linear architectures, such as star-polymers, the viscosity can be substantially lowered, whereby the overall sample throughput can be greatly improved over the present state-of-the art systems, and preferably without substantially affecting resolution of the sample components.

A further class of embodiments of the invention are directed to separation media for capillary gel electrophoresis that comprise a blend of polymers. Such separation media comprise at least two different polymers and an aqueous medium. As used herein, the term "different polymers" means that the polymers differ with respect to composition, chain length (e.g. especially for linear polymers), architecture (e.g., especially for non-linear polymers), crystallinity, and/or hydrodynamic volume. Hence, two linear polymers having the same repeat units can be different polymers if they have different average chain lengths (typically characterized by size exclusion chromatography/hydrodynamic volume). Two linear polymers having identical chain lengths, but different repeat units, or different arrangement of repeat units are also considered to be different polymers. Moreover, in these embodiments, the contemplated scope of the repeat units for the polymers is broader—in that such media can consist essentially of polymeric components that do not include polymers having acrylamide-based repeat units. Preferably, however, one or more of the polymers will include acrylamide-based repeat units.

Hence, in one embodiment with a blend of polymers, the separation media for capillary gel electrophoresis can include a first polymer and second polymer. The first and the second polymer are different polymers, but each are at least partially soluble in water or aqueous medium, or dispersible in water or aqueous medium. The polydispersity index of each of the first and second polymers is not more than about 2.0. These polymers can differ from each other, among other features or properties, based on molecular weight. Each of such polymers are combined with (e.g., solubilized or dispersed in) an aqueous medium to form a solution or dispersion with a viscosity suitable for capillary gel electrophoresis. At least one of the polymers can preferably (but does not necessarily) comprise acrylamide-based repeat units.

In another preferred embodiment with a blend of polymers, the separation media for capillary gel electrophoresis comprises three or more different polymers—a first polymer, a second polymer and a third polymer, each of which are at least partially soluble in water or aqueous medium, or dispersible in water or aqueous medium, and have a polydispersity index of not more than about 2.0, but which are different from each other with respect to molecular weight. The first polymer is preferably a relatively low-molecular weight polymer, and can have, for example, a molecular weight ranging from about 10,000 to about 250,000. The second polymer is preferably a relatively medium-molecular weight polymer, and can have, for example, a molecular weight ranging from about 250,000 to about 750,000. The third polymer is preferably a relatively high-molecular weight polymer, and can have, for example, a molecular weight greater than about 750,000, and preferably ranging from about 750,000 to about 25,000,000. Each of such polymers are combined with (e.g., solubilized or dispersed in) an aqueous medium to form a solution with a viscosity suitable for capillary gel electrophoresis. At least one of the polymers, preferably at least two of the polymers and more preferably each of the three or more polymers can preferably (but not necessarily) comprise acrylamide-based repeat units. This particular embodiment, which offers a blend of narrow-band polymers of different molecular weights, is particularly advantageous with respect to high-resolution of DNA polynucleotides of widely-varying numbers of nucleotides (base pairs).

In another embodiment with a blend of polymers, the separation media for capillary gel electrophoresis can include a first polymer and second polymer. The first and the second polymer are different polymers, but each are at least partially soluble in water or aqueous medium, or dispersible in water or aqueous medium. The first polymer has a polydispersity index of not more than about 2.0. The second polymer has a weight-average molecular weight of at least about 75,000. Each of such polymers are combined with (e.g., solubilized or dispersed in) an aqueous medium to form a solution or dispersion with a viscosity suitable for capillary gel electrophoresis. At least one of the polymers can preferably (but does not necessarily) comprise acrylamide-based repeat units.

In still another embodiment with a blend of polymers, the separation media for capillary gel electrophoresis can include a first polymer and second polymer. The first and the second polymer are different polymers, but each are at least partially soluble in water or aqueous medium, or dispersible in water or aqueous medium. At least one of the first and second polymer is non-linear. Each of the polymers are combined with (e.g., solubilized or dispersed in) an aqueous medium to form a solution or dispersion with a viscosity suitable for capillary gel electrophoresis. Preferably, the at least one non-linear polymer has a star-polymer architecture. At least one of the polymers can preferably (but does not necessarily) comprise acrylamide-based repeat units.

In a further embodiment with a blend of polymers, the separation media for capillary gel electrophoresis includes a first polymer and second polymer. The first and the second polymer are different polymers, but each at least partially soluble in water or aqueous medium, or dispersible in water or aqueous medium. The first polymer is a linear polymer, and the second polymer is a non-linear. Each of the polymers are combined with (e.g., solubilized or dispersed in) an aqueous medium to form a solution or dispersion with a viscosity suitable for capillary gel electrophoresis. Preferably, the non-linear polymer has a star-polymer architecture. At least one of the polymers, and preferably both, can preferably (but do not necessarily) comprise acrylamide-based repeat units. A blend comprising linear and non-liner polymers is particularly advantageous for capillary gel electrophoresis. Without being bound by theory not specifically recited in the claims, such a blend provides a combination of benefits associated with non-linear polymers (e.g., stars), having centers of concentrated mass, as discussed above, and between or among such centers, regions of entangled linear polymers and/or regions of linear polymers entangled with portions of the non-linear polymer (e.g., the arms of the star-polymers).

Also, the separation media may include other components that are commonly employed for different applications. Other components may include buffering agents or solutions, denaturing agents and the like. See, e.g., U.S. Pat. No. 5,885,432, incorporated herein by reference.

Capillary Gel Electrophoresis

Capillary gel electrophoresis systems are commercially available from a variety of manufacturers including, e.g., Perkin Elmer Applied Biosystems, Beckman, and Molecular Dynamics. Capillary gel electrophoresis instruments generally include a capillary capable of being connected at opposite ends to opposing polarity terminals of a voltage source, a detector, a sampling mechanism, and a separation medium disposed within the capillary. The geometry of the capillary is not critical. Typically, the capillary can be a tube (e.g., a silica tube) and/or a channel (e.g., formed in the surface of a substrate).

The capillaries of the present invention can have an inner diameter or width ranging from about 5 µm to about 200 um, preferably ranging from about 5 µm to about 100 µm, and more preferably ranging from about 10 µm to about 75 µm. In particular, the s preferably have a diameter or width of not more than about 100 µm, preferably not more than about 75 µm, not more than about 50 µm, not more than about 25 um, not more than about 10 µm, and not more than about 5 µm. Such capillaries can be closed or open capillaries, and can have a cylindrical-shaped interior geometry or a non-cylindrical interior geometry (e.g., oval, square, triangular, parallelogram). Such geometries may be dictated (or even preferred), for example, due to the fabrication techniques (e.g., etch angles associated with microfabrication). Hence, more generally, the capillaries can have a hydraulic radius (i.e., cross-sectional area divided by circumference (or partial circumference for open channels) ranging from about 0.25 µm to about 50 um, preferably ranging from about 0.25 µm to about 25 µm, and more preferably ranging from about 2 µm to about 20 µm. In particular, the capillaries preferably have a hydraulic radius of not more than about 25 µm, preferably not more than about 20 µm, not more than about 15 µm, not more than about 10 um, not more than about 2 µm, and not more than about 0.25 µm. The length of the capillary can range from about 1 cm to about 100 cm, and preferably from about 10 cm to about 100 cm. The capillaries are often made of fused silica. Flow of the separation medium can be restricted by, e.g., the use of a frit or constricted plug, which prevents the flow of the separation medium out of the tube.

According to one aspect of the present invention, even relatively small-diameter or width capillaries—e.g., having an interior diameter or width of not more than about 75 µm (and preferably less, with incrementally smaller diameter or widths/hydraulic radius as described above) can be filled, flushed and refilled. Hence, the capillary gel electrophoresis system can comprise a fill port for providing separation medium to one or more capillaries, a flushing port for removing spent medium therefrom, a motive force source (e.g., pump) for effecting movement of the separation media into and/or out of the capillary, and optionally, and preferably, a process control system for controlling such operations. Such a process control system can include a computer, software providing a control logic, and one or more control elements (e.g., valves, pump speed controller, etc).

In operation, the separation medium is pumped into the tube so as to fill the tube with the separation medium. Volumetric flowrates for filling the tube are controlled by the pump speed to range, generally, from about 50 µl/min to about 100 µl/min. The separation medium should fill the tube substantially uniformly and homogeneously, such that voids or discontinuities that would interfere with the sample analysis are minimized, and preferably substantially nonexistent. Typically, the medium is stationary (not flowing) during the analysis. In some applications, however, flow—in the same direction as sample-molecule migration or counter-current thereto—can be maintained through the capillary throughout the analysis. The sample(s) to be analyzed can be placed into the separation media prior to loading such media into the capillary, or alternatively, such sample(s) can be applied to an exposed surface of the separation media or applied to a subsurface volume of the separation media after the separation medium has been established into the capillary, for example, by electro-kinetic injection. An electric field is applied across the capillary. The sample, now subjected to the electric field, migrates through the separation medium to the detector, with different sample components migrating at different relative speeds through the separation medium. The detector provides an output signal, typically versus a time domain. The output signal is typically generated, for DNA sample fractions, by detecting tags incorporated into the particular nucleotides (A, C, T and/or G). The output signal can be correlated to the signal obtained from samples comprising standards of known fractions. For example, for analysis of DNA samples, DNA ladders with fractions having a known number and sequence of base pairs can be used for the correlation.

The capillaries of the aforementioned capillary gel electrophoresis systems preferably comprise one of the separation medium described above, alone, or in combination with other separation media.

Preparation of Controlled-Architecture Polymers

The controlled-architecture polymers, as variously characterized above, can be prepared by several different approaches, depending on the desired architecture and desired properties of the polymer. In general, those of skill in the art will appreciate that the polymerization processes of this invention are preferably living-type polymerization and more preferably a nitroxide mediated polymerization process. However, a "semi-controlled" process may be employed, where semi-controlled refers to a free radical polymerization process that starts out with living-type kinetics (e.g., controlled), but thereafter is run out of control, typically in order to achieve the desired molecular weights in a more timely polymerization process. A controlled free radical polymerization can be driven out of control by several different methods, such as by destroying the control agent (i.e., adding a chemical to react with the control agent and/or heat and/or light) or reducing the concentration of controlled chains in the polymerization reaction to a level that does not supply control. Uncontrolled polymerizations may also be employed. Those of skill in the art can chose between the known different living type polymerization processes to find a process that best fits a particular application, with such techniques typically including nitroxide mediated, radical addition fragmentation transfer (RAFT or MADIX), iniferter and atom transfer radical polymerization (ATRP).

In order to generalize these different types of techniques, several different notations are used herein. First, the notation "YE" is used to describe a free radical initiator, where the —Y-E bond breaks in a reversible or irreversible manner. After the YE bond breaks, E will be a radical, generally, and can act in accord with the various mechanisms known to those of skill in the art. Thus, both controlled, un-controlled and semi-controlled free radical polymerization processes are within this definition. Another notation used herein, when an initiator-control agent adduct is intended, is the more specific notation —IC, where the C may appear in squiggly lines, which refers to a controlled polymerization that proceeds via a radical capping mechanism, such as nitroxide radical controlled or ATRP polymerization. The YE or IC notations are not intended to limit the other reactants or components of the polymerization mixture. Therefore, YE may irreversibly cleave, but the polymerization may proceed via a nitroxide mediated process if stable free nitroxide radical is added to the polymerization mixture. The YE bond may also reversibly cleave.

The polymers are preferably prepared by controlled, living free radical polymerization methods. Controlled, living free radical polymerization approaches offer the flexibility of reproducibly preparing polymers of specific tailored architecture, molecular weight, low polydispersity index, and low viscosity, among other properties of interest. Although controlled, living free radical polymerization approaches have been developed and employed for other applications, such approaches have not heretofore been applied to the preparation of controlled-architecture polymers comprising acrylamide-based repeat units and having the architectures and/or characterizing properties described above. Moreover, controlled living free radical polymerization has not heretofore been demonstrated in the solution phase using the preferred control agents of the present invention (i.e., alpha-destabilizing moiety nitroxides such as alpha-hydrido nitroxides)—regardless of the vinyl ("vinyl" being used, in this regard, to broadly include monomers having a polymerizable double carbon-carbon bond) monomer.

Polymers are prepared according to a controlled, living free-radical polymerization method, in general, by reacting a free-radical initiator with a monomer in the presence of a free-radical control agent or other controlling technique. Solvents (e.g., water) and polymerization-enhancing additives, such as accelerators or control-agent destabilizing reagents, can also be present during the reaction. Without being bound by theory, the controlled, living free-radical polymerization involves a reaction between the free-radical initiator and a monomer having a carbon-carbon double bond to form an intiator-monomer radical ($I-M_1 \cdot$). This radical can itself undergo further reaction with a second such monomer to form an intiator-monomer-monomer radical ($I-M_1-M_2 \cdot$), which can then itself undergo further reaction with an additional monomer, etc.—repeating "n" times to incorporate "n" monomers into the chain ($I-M_1-M_2-M_3 \ldots -M_n$), until the chain reaction is terminated. In the reversible capping mechanism, control agents, typically stable free-radicals in the absence of other radicals, can react with the free radical of the growing polymer chain to "cap" the chain. However, an equilibrium established between the free-radical control agent and the control-agent "caps" allows the "capped" chain to become "uncapped" for definitive periods sufficient to react with another monomer. The control-agent equilibrium can be controlled, at least to some extent, by changing the reaction conditions—thereby providing livingness to the system. The polymerization can, in general, be carried out in homogeneous or heterogeneous media, including in bulk (i.e., in a solvent which is also a monomer), in solution (aqueous or organic), or in emulsion. The polymerization is preferably effected in aqueous solution or in bulk.

A polymerization reaction mixture of this invention uses those components that are needed for the particular mechanism being practiced. For the preferred embodiments of a branched or star architecture, a mulit-functional initiator (or initiator-control agent adduct) may be all that is needed with monomer. Alternatively or in addition, a reversible capping control agent (e.g., free radical (e.g., a nitroxide radical) or metal-ligand in an ATPR scheme) may be added, or the mulitfunctional initiator can be an iniferter modified molecule, etc. In other preferred embodiments, a multifunctional monomer is used, with a monofunctional initiator (e.g., a conventional initiator) or a multifunctional initiator or initiator-control agent adduct.

A reaction mixture comprising the free-radical intiator, monomer and a stable free-radical control agent can be formed in a number of different ways. The control agent can be provided to the reaction mixture as a stable free-radical, or alternatively, can be formed in situ under polymerization reaction conditions from a stable free-radical control agent precursor. Likewise, the free-radical initiator can be provided as such to the reaction mixture, or can be formed in situ under initiation conditions or under polymerization reaction conditions from a free-radical initiator precursor. In one approach, both the free-radical initiator and the control agent can be formed in situ from a common initiator-control agent adduct. Each of the reaction mixture components and the variations for forming the reaction mixture are discussed and exemplified in greater detail below.

As used herein the term "multi-functional initiator" refers to a molecule that has more than 2 points from which a free radical polymerization may be initiated. Multi-functional initiators can have a variety of structures and atoms, but are generally used to form star or branched polymers. In addition, multi-function initiators are used to distinguish a less preferred method of polymer formation, which is generally referred to as convergent synthesis. Convergent synthesis is shown, for example, in U.S. Pat. No. 5,759,369, where a star center group or linking group is used to join polymer fragments together in a desired format. This method of polymer formation is less desired due to its complexity and slow, multi-step synthesis requirements. Moreover, convergent polymer formation limits the molecular weight of the resultant polymer. Multi-functional initiators eliminate the need for such a slow, complex process of polymer formation and allow for much higher molecular weights, more complex branching and a simpler polymerization process, including one-pot synthesis processes. As used herein, multi-functional initiators, include multi-arm star initiators as well as polymers or polymer fragments that have initiators built into the backbone or chain. These types of multi-functional initiators are discussed herein especially in connection with star and branched polymer architectures.

Nitroxide Control Agents

The free-radical control agent of the present invention is preferably a nitroxide control agent, and more preferably, a nitroxide control agent having an alpha-destabilizing moiety. Alpha-hydrido-nitroxide control agents are particularly preferred. In preferred embodiments, the free radical control agents that are useful in this invention may be characterized by the general formula II:

(II)

where each of $R^1$, $R^2$ and $R^3$ are the same or different straight chain, branched or cyclic substituted or unsubstituted alkyl groups, including, for example, hydrogen, alkyl, substituted alkyl, cycloalkyl, substituted cycloalkyl, heteroalkyl, heterocycloalkyl, substituted heterocycloalkyl, aryl, substituted aryl, heteroaryl, substituted heteroaryl, alkoxy, aryloxy, silyl, boryl, phosphino, amino, thio, seleno, and combinations thereof; $R^1$ and $R^2$ may be joined together in a cyclic ring structure; likewise, $R^2$ and $R^3$ may be joined together in a cyclic ring structure that may have fused with it another saturated or aromatic ring; and X is a moiety that is capable of destabilizing the free radical. By "destabilizing moiety" or by "capable of destabilizing" it is meant that the moiety, "X", allows the free radical to destabilize, decompose, destroy, or otherwise remove itself from the reaction (e.g. spontaneously or by interaction with another such control agent), or to be destabilized, be decomposed, be destroyed or be removed from the reaction by the addition of a reagent. The R groups should be chosen so that there is only one hydrogen atom alpha to the nitrogen. Thus, when X is hydrogen, $R^3$ is selected from the group consisting of tertiary alkyl, substituted tertiary alkyl, aryl, substituted aryl, tertiary cycloalkyl, substituted tertiary cycloalkyl, tertiary heteroalkyl, tertiary heterocycloalkyl, substituted tertiary heterocycloalkyl, heteroaryl, substituted heteroaryl, alkoxy, aryloxy and silyl. For the aqueous solution polymerization, it is preferred that one of the R groups ($R^1$, $R^2$ or $R^3$) includes a water-solubilizing group, such as sulfonate, sulfate, carboxylate, hydroxyl, amino, ammonium and the like, to enhance the solubility of the control agent. The presence of monomer in the reaction mixture can, in some cases, also enhance the solubility of the control agent.

In more specific embodiments, each $R^1$, $R^2$ and $R^3$ is independently selected from a group consisting of alkyl, substituted alkyl, cycloalkyl, substituted cycloalkyl, heteroalkyl, substituted heteroalkyl, heterocycloalkyl, substituted heterocycloalkyl, aryl, substituted aryl, heteroaryl, substituted heteroaryl and silyl. Specific examples of $R^1$, $R^2$ and $R^3$ are methyl, ethyl, propyl, butyl, cyclopentyl, cyclohexyl, cyclooctyl, phenyl, benzyl, trimethylsilyl, those specific moieties listed in the above definitions and the like. In alternative embodiments, $R^1$, $R^2$ or $R^3$ may include a water-solubilizing group, such as $SO_3G$, where G is Na, K and the like. In a preferred embodiment, $R^1$ is an aryl (such as phenyl), $R^2$ is an alkyl (such as isopropyl) and $R^3$ is either an alkyl or a heteroalkyl (such as tert-butyl or $Me_3SiOCH_2(CH_3)_2C$). In an alternative preferred embodiment, $R^1$ is an aryl (such as phenyl), R is a cycloalkyl (such as cyclohexyl or cyclopentyl) or a tertiary alkyl (such as tert-butyl) and $R^3$ is either a tertiary alkyl or a heteroalkyl (such as tert-butyl or $Me_3SiOCH_2(CH_3)_2C$). In still another preferred embodiment, $R^1$ is a substituted alkyl (such as $NC(CH_3)_2C$) and $R^2CNR^3$ form a cyclic ring structure.

Initiators

The initiators employed in the present invention can be a commercially available free-radical initiator. In general, however, initiators having a short half-life at the polymerization temperature are preferred. Such initiators are preferred because the speed of the initiation process can affect the polydispersity index of the resulting polymer. That is, the kinetics of controlled, living polymerization are such that less polydisperse polymer samples are prepared if initiation of all chains occurs at substantially the same time. The initiators are preferably water-soluble initiators and/or monomer-soluble initiators, but can also include non-aqueous solvent-soluble initators. More specifically, suitable free radical initiators include any thermal, redox or photo initiators, including, for example, alkyl peroxides, substituted alkyl peroxides, aryl peroxides, substituted aryl peroxides, acyl peroxides, alkyl hydroperoxides, substituted alkyl hydroperoxides, aryl hydroperoxides, substituted aryl hydroperoxides, heteroalkyl peroxides, substituted heteroalkyl peroxides, heteroalkyl hydroperoxides, substituted heteroalkyl hydroperoxides, heteroaryl peroxides, substituted heteroaryl peroxides, heteroaryl hydroperoxides, substituted heteroaryl hydroperoxides, alkyl peresters, substituted alkyl peresters, aryl peresters, substituted aryl peresters, azo compounds and halide compounds. Specific initiators include cumene hydroperoxide (CHP), t-butyl hydroperoxide (TBHP), t-butyl perbenzoate (TBPB), sodium carbonateperoxide, benzoyl peroxide (BPO), lauroyl peroxide (LPO), methylethylketone peroxide 45%, potasium persulfate, ammonium persulfate, 2,2-azobis(2,4-dimethylvaleronitrile) (VAZO®-65), 1,1-azobis (cyclo-hexanecarbonitrile) (VAZO®-40), 2,2-azobis(N,N'-dimethyleneisobutyramidine)dihydrochloride (VAZO®-044), 2,2-azobis(2-amidino-propane) dihydrochloride (VAZO®-50) and 2,2-azobis(2-amido-propane)dihydrochloride. Redox pairs such as persulfate/sulfite and Fe(2+)/peroxide are also useful. As noted above, and as used herein, the initiator may be added to the polymerization mixture independently or may be incorporated into another molecule, such as a monomer (discussed below for hyper branching) or a polymer or polymer fragment (for grafting, etc.). Thus, the notation for the initiator or a fragment thereof may be I, i, Y or YE, etc., depending on the embodiment being practiced. The initiators useful herein may also be mulit-functional initiators, as discussed herein. Initiation may also be by heat or UV light, as is known in the art, depending on the embodiment being practiced (e.g., UV light may be used for the modified iniferter or RAFT or MADIX techniques discussed herein). Those of skill in the art can select a proper initiator within the scope of this invention.

Nitroxide Control Agent/Initiator Adducts

In one embodiment, free-radical control agent and free-radical initiator are each generated in situ from a control agent—initiator adduct. Such an adduct can be characterized by the general formula III:

where $R^1$, $R^2$, $R^3$ and X have the above meanings, while Y is a residue capable of initiating free radical polymerization upon homolytic cleavage of the Y—O bond, including, for example, alkyl, substituted alkyl, alkoxy, substituted alkoxy, heteroalkyl, substituted heteroalkyl, aryl, and substituted aryl residues. Use of such adducts can eliminate concerns about the speed of initiation of polymer chains, effectively initiating all polymer chains at substantially the same time upon addition of the adduct to the monomer-under polymerization conditions. The adducts may be prepared by methods known in the art, such as disclosed in WO 99/03894, which is incorporated herein by reference. In another such embodiment, the control agent is generated in situ from the nitrone precursor, as is also discussed below and in WO 99/03894. The adducts of the invention are, for polymerization in aqueous solution, preferably water soluble, or at least water soluble in the presence of the monomer.

Figure 2C:
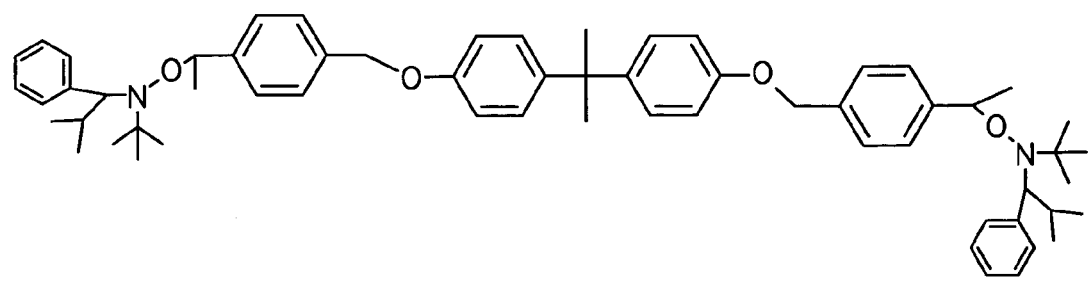
Figure 2D:
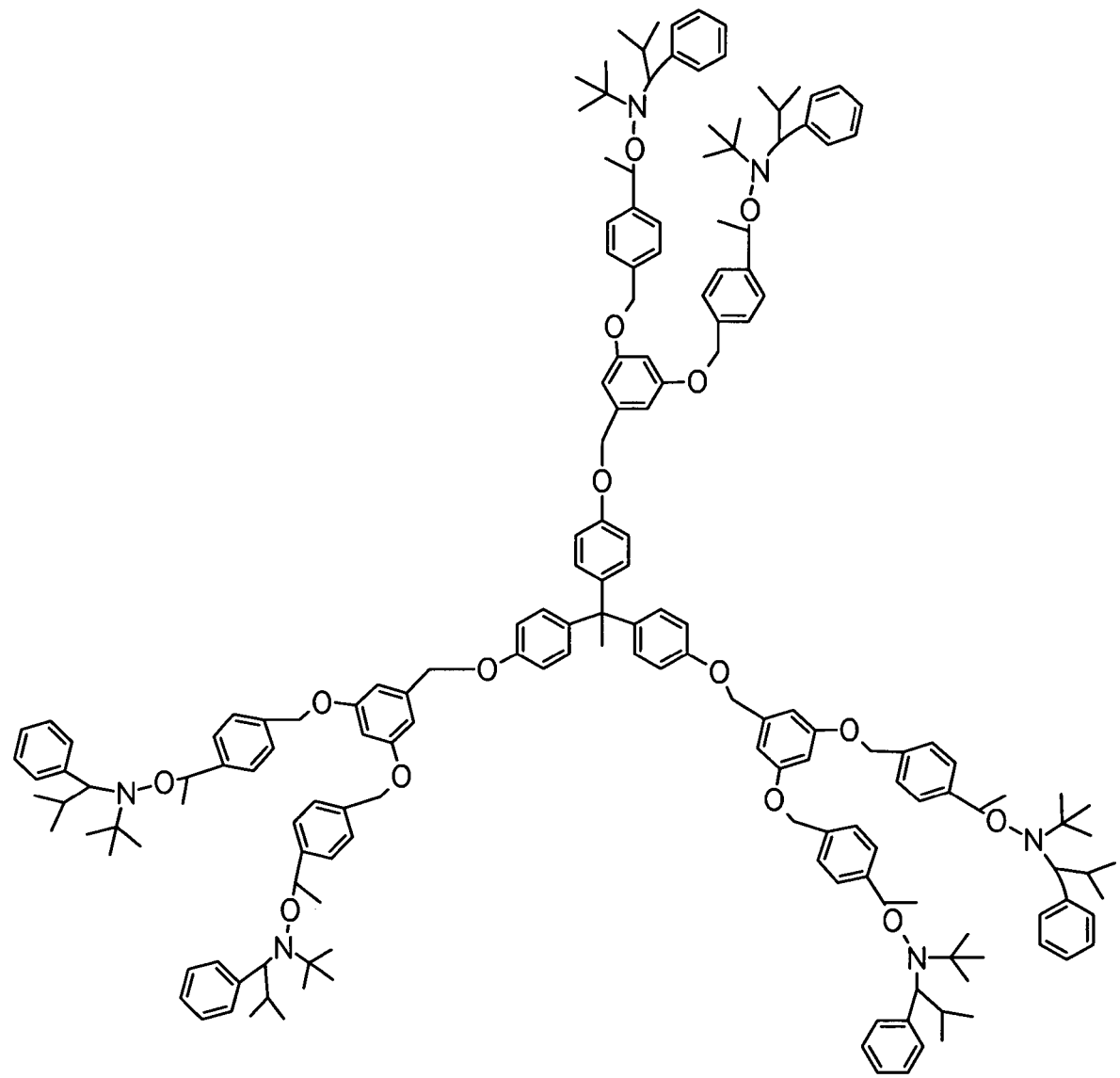
Figure 2E:
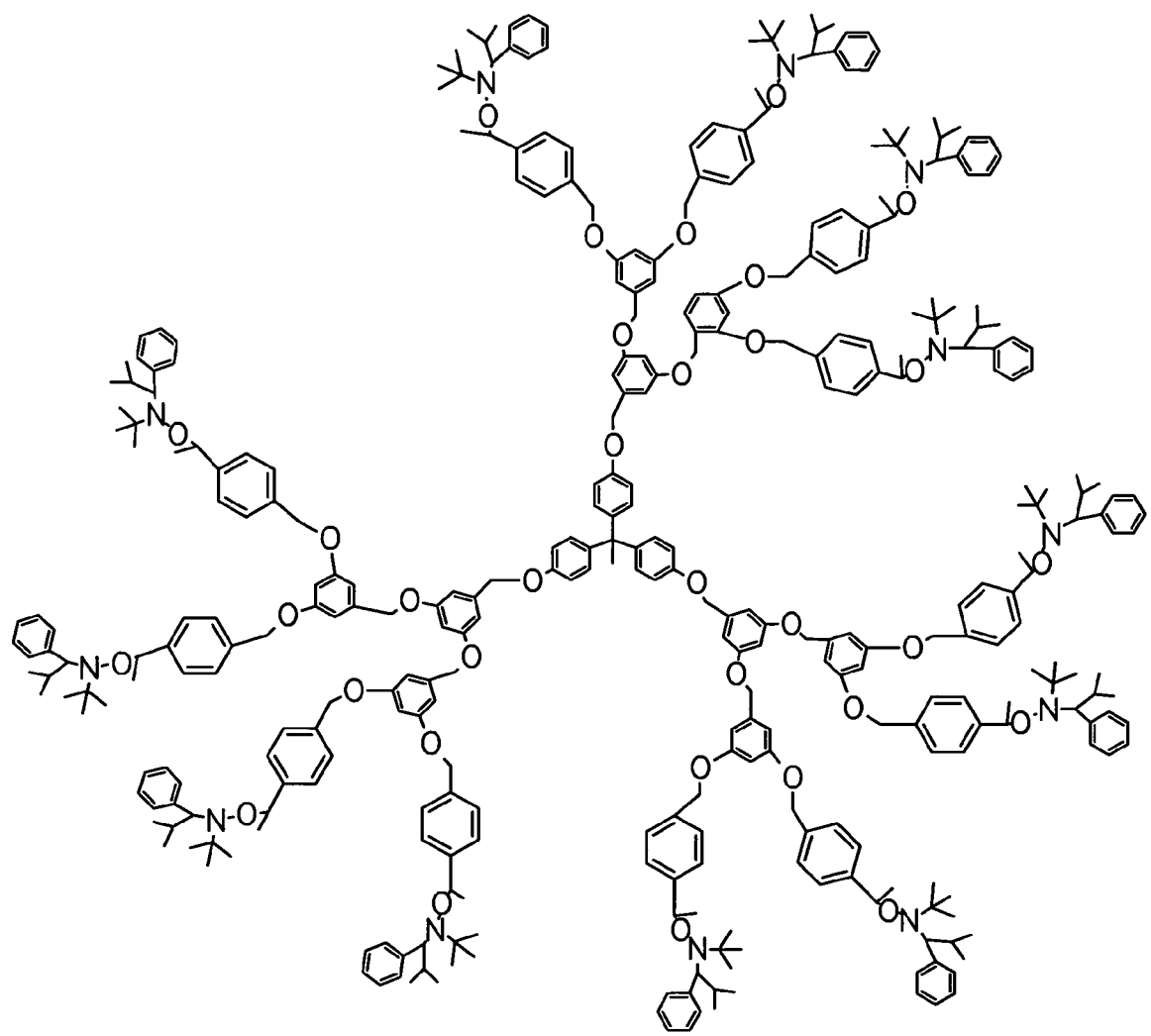

Preferred adducts for the preparation of "2-arm" linear polymers and 6-arm and 12-arm star-polymers are shown in FIGS. 2C, 2D and 2E. These preferred adducts can be prepared as described in Example 1A and 1B.

In another embodiment, the adducts useful in this invention encompass compounds having monomer, oligomer or polymer disposed between the Y residue and the oxygen atom of the adduct, as shown in formula IV, below. Thus, embodiments including compounds of the structure shown in formula IV are within the definition of "adduct" as that term is applied to the invention. That is, the growing polymer chain, as well as the "capped" chain can themselves be considered adducts (with $Y'\text{-}(M)_n$—being considered the Y moiety as referred to above in connection with formula III). An adduct comprising an oligomer or polymer of this invention may be characterized by the formula:

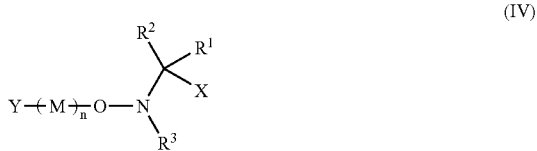

(IV)

where $R^1$, $R^2$, $R^3$ and X have the above-recited meanings and scope, and $Y^1$ can be the same as Y as recited above (Y may also be derived from the list of initiators discussed above); M is one or more monomer units selected from the monomers described below, and n is an integer that may be zero, 1 or greater than 1. Thus, for example, when n is zero, the compound of formula IV collapses to the compound of formula III. When n equals 1, the compound of formula IV can be considered a first-monomer adduct. When n is 2 or more, the compounds of formula IV are considered to be oligomer adducts or polymer adduct. All of such various adducts are capable of initiating the free radical polymerizations of the invention—due to the livingness of the nitroxide control agent acting as a "cap" on the initiating fragment of such adduct.

Preparation of Preferred Initiator-Control Agent Adducts is Exemplified in Examples 1A through 1C.

It is frequently convenient to generate the Y (or Y') radical in the presence of monomer and control agent, and to isolate an adduct of formula IV where n ranges from 1 to about 5, is preferably 2 or 3, and is more preferably 1. These are isolable compounds that can be easily purified and used in subsequent polymerization processes of the invention.

Monomers

The monomers used in the polymerization process of the invention are those discussed above in connection with the polymers and as discussed in this section. Hence, in general, the monomers are acrylimidic monomers, and are preferably selected from monomers having the formulas I or I':

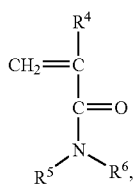

I

-continued

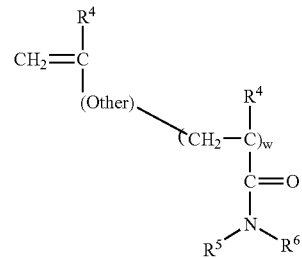

I' where $R^4$, $R^5$ and $R^6$ are as defined above, w is an integer of 1 or more; "Other" refers to any other possible atoms in the monomer, such as linker atoms, and typically is up to 50 non-hydrogen atoms, more preferably to to 20 non-hydrogen atoms. In preferred embodiments w is more than 50, preferably more than 100 and most preferable more than 300. In preferred embodiments, the monomers can be acrylamide, methacrylamide, N-alkylacrylamide (e.g., N-methylacrylamide, N-tert-butylacrylamide, and N-n-butylacrylamide), N-alkylmethacrylamide (e.g., N-tert-butylmethacrylamide and N-n-butylmethacrylamide), N,N-dialkylacrylamide (e.g., N,N-dimethylacrylamide), N,N-dialkylmethacrylamide, N-methylolmethacrylamide, N-ethylolmethacrylamide, N-methylolacrylamide, N-ethylolacrylamide, and combinations thereof. In another preferred embodiment, the polymers comprise acyrlamidic repeat units derived from monomers selected from N-alkylacyrlamide, N-alkylmethacrylamide, N,N-dialkylacrylamide and N,N-dialkylmethacrylamide. Preferred repeat units can be derived, specifically, from acrylamide, methacrylamide, N,N-dimethylacrylamide, and tert-butylacrylamide.

Figure 3A:
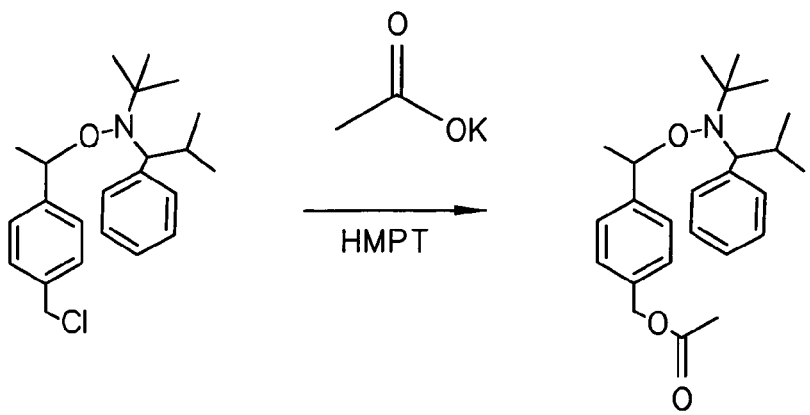
FIGS. 3A-3C show the reaction scheme for making hyper-branched structures with macromonomers, as exemplified in Example 2 h.
Figure 3B:
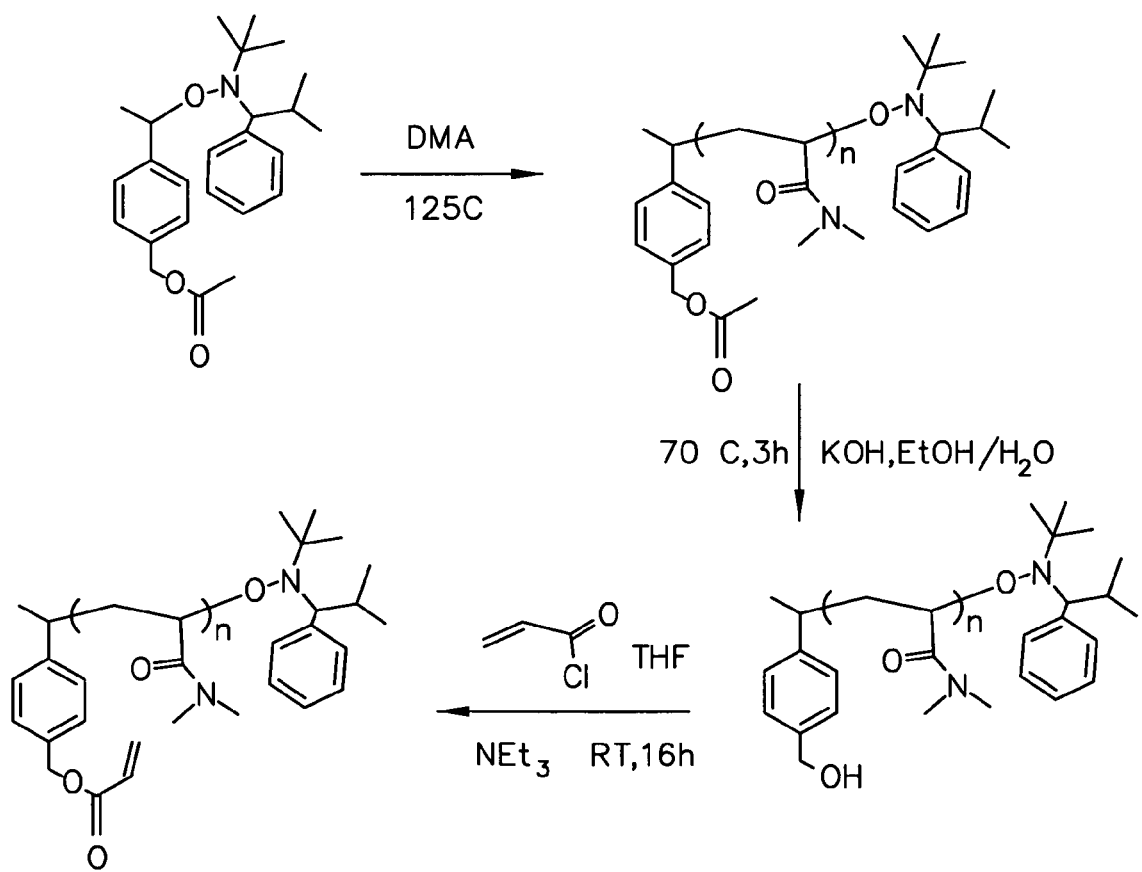

The monomers of formula I' are generally macro-monomers (sometimes referred to a macromers), and typically provide branches in the polymer, either off of the polymer backbone or off a branch. Thus, for example, a star architecture polymer may have branches off the arms of the star, most preferably prepared by using a macromonomer of formula I'. Thus, Other in formula I' refers to any other possible atoms that may come between the repeating portion of the macromonomer and the vinylic double bond. Preferably Other atoms comprise up to 20 non-hydrogen atoms, including for example a phenyl group, a ester group, an carboxamide group, and the like. A specific example of a macromonomer used herein is shown in FIG. 3B. It should be noted that the macromonomers may fall within formula IV, above, which is the specific example shown in FIG. 3B.

While polymers comprising the acrylamidic repeat units as described above are generally preferred, a broader scope of monomers is contemplated with respect to controlled, living free-radical polymerization reactions in the aqueous phase. For aqueous-solution polymerization by controlled, living free-radical approaches, the monomer can, in addition to the aforementioned acrylimidic monomers, also be selected from monomers such as styrene, substituted styrene, alkyl acrylate, substituted alkyl acrylate, alkyl methacrylate, substituted alkyl methacrylate, acrylonitrile, methacrylonitrile, isoprene, butadiene, ethylene, vinyl acetate and combinations thereof. Functionalized versions of these monomers may also be used. Specific examples include methyl methacrylate, ethyl methacrylate, propyl methacrylate (all isomers), butyl methacrylate (all isomers), 2-ethylhexyl methacrylate, isobornyl methacrylate, methacrylic acid, benzyl methacrylate, phenyl methacrylate, methacrylonitrile, α-methylstyrene, methyl acrylate, ethyl acrylate, propyl acrylate (all isomers), butyl acrylate (all isomers), 2-ethylhexyl acrylate, isobornyl acrylate, acrylic acid, benzyl acrylate, phenyl acrylate, acrylonitrile, styrene, glycidyl methacrylate, 2-hydroxyethyl methacrylate, hydroxypropyl methacrylate (all isomers), hydroxybutyl methacrylate (all isomers), N,N-dimethylaminoethyl methacrylate, N,N-diethylaminoethyl methacrylate, triethyleneglycol methacrylate, itaconic anhydride, itaconic acid, glycidyl acrylate, 2-hydroxyethyl acrylate, hydroxypropyl acrylate (all isomers), hydroxybutyl acrylate (all isomers), N,N-dimethylaminoethyl acrylate, N,N-diethylaminoethyl acrylate, triethyleneglycol acrylate, vinyl benzoic acid (all isomers), diethylaminostyrene (all isomers), α-methylvinyl benzoic acid (all isomers), diethylamino α-methylstyrene (all isomers), p-vinylbenzene sulfonic acid, p-vinylbenzene sulfonic sodium salt, trimethoxysilylpropyl methacrylate, triethoxysilylpropyl methacrylate, tributoxysilylpropyl methacrylate, dimethoxymethylsilylpropyl methacrylate, diethoxymethylsilylpropyl methacrylate, dibutoxymethylsilylpropyl methacrylate, diisopropoxymethylsilylpropyl methacrylate, dimethoxysilylpropyl methacrylate, diethoxysilylpropyl methacrylate, dibutoxysilylpropyl methacrylate, diisopropoxysilylpropyl methacrylate, trimethoxysilylpropyl acrylate, triethoxysilylpropyl acrylate, tributoxysilylpropyl acrylate, dimethoxymethylsilylpropyl acrylate, diethoxymethylsilylpropyl acrylate, dibutoxymethylsilylpropyl acrylate, diisopropoxymethylsilylpropyl acrylate, dimethoxysilylpropyl acrylate, diethoxysilylpropyl acrylate, dibutoxysilylpropyl acrylate, diisopropoxysilylpropyl acrylate, maleic anhydride, N-phenylmaleimide, N-butylmaleimide, butadiene, isoprene, chloroprene, ethylene, vinyl acetate, 2-(2-oxo-1-imidazolidinyl)ethyl 2-methyl-2-propenoate, 1-[2-[[2-hydroxy-3-(2-propyl)propyl)]amino]ethyl]-2-imidazolidinone, N-vinyl pyrrolidone, N-vinyl imidazole, crotonic acid, vinyl sulfonic acid, and combinations thereof.

In other embodiments of this invention, multi-functional monomers are used. Multi-functional monomers refers to monomers that have two or more polymerizable vinylic moieties present in the monomer, which are typically present at different ends of the monomer. Generally, these multi-functional monomers may be represented by the general formula V:

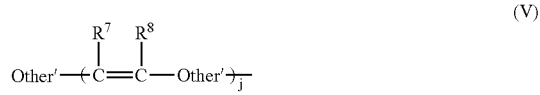

(V)

wherein Other' comprises linking atoms, comprising up to 50 non-hydrogen atoms (of course hydrogen can also be included in the multifunctional monomers, but not in the backbone of the "other" atoms); j is 2, 3 or 4; and each $R^7$ and $R^8$ is independently selected from the group consisting of hydrogen, alkyl, substituted alkyl, cycloalkyl, substituted alkyl, substituted aryl and combinations thereof; and, optionally, $R^7$ and $R^8$ are joined in a ring structure, wherein said ring has (including the two carbon atoms and $R^7$ and $R^8$) from 4 to 20 non-hydrogen atoms in the ring. In addition that atoms that comprise the other' atoms may be linked together. Other' atoms in the linking group are more preferably up to 20 non-hydrogen atoms and typically include N and O atoms. Some illustrative examples of multi-functional monomers that may be used include N-methylene-bisacrylamide, N-hexamethylene-bisacrylamide, bis and tris-acrylates (in general), trimethylolpropane triacrylate ester; ethylene glycol dimethacrylate; diphenyl bismaleamide and the like.

Typically, multi-functional monomers are used in two embodiments of this invention. First, bi-functional monomers are useful to form cross-linked polymeric polyfunctional "core" molecules, as discussed herein. Second, multi-functional monomers may be used to form branched or hyper-branched polymers, as discussed herein, when used in conjunction with conventional initiators and the acrylamide-type monomers discussed herein. In some embodiments, a chain transfer agent is needed to effect a controlled polymerization when using the multi-functional initiators. Chain transfer agents are known in the art, and may be chosen from those known to those of skill in the art. Chain transfer agents that may be used include alcohols (such as methanol, ethanol and isopropanol), and thio compounds (e.g., thiols), hydroxyethyl mercaptan, $C_1$-$C_{12}$ branched or linear alkyl mercaptans, mercaptopropionic esters, and polyhalogenated hydrocarbons (such as carbon tetrachloride).

Accelerators

Suitable accelerators that may be included in the polymerization system include alkylating and acylating agents, Lewis Acids, ketones, aldehydes, anhydrides, acid esters, imides, oxidants and reducing agents. Specific accelerators include acetic acid, acetic anhydride, camphor sulfonic acid, acetole (1-hydroxyacetone) and the like. Other accelerators useful herein are recited in Hawker et al., "Development of a New Class of Rate-Accelerating Additives for Nitroxide-Mediated 'Living' Free Radical Polymerization," *Tetrahedron*, Vol. 53, No. 45, pp. 15225-15236 (1997), which is incorporated herein by reference.

Solvent

Various solvents can be employed for polymerization in solution phase. Selection of solvent is dependent on the monomer, among other factors. In preferred embodiments, the polymerization is effected in aqueous solution—with the solvent being water or an aqueous medium (as defined above in connection with the separation medium). For polymerization in bulk, the monomer (or slightly diluted monomer) is the "solvent".

Polymerization Reaction

A reaction mixture comprising the stable free-radical control agent (or precursor thereof), monomer and the free-radical initiator (or precursor thereof) is formed. Typically, control agent and monomer are combined, optionally with other components, and then initiator is added as a last component to form the reaction mixture. Alternatively, the initiator and control agent can be added together as a final step (e.g., as a control agent-initiator adduct). Similar protocols can be followed in bulk or in aqueous solution.

Control of the polymerization reaction for preparing the controlled-architecture polymers of the invention is provided by controlling various combinations of the following: selection of initiator; selection of control agent; selection of monomer; amount of control agent; the ratio of initiator to control agent; the ratio of monomer to initiator; timing of addition of monomers; and polymerization reaction conditions. In a preferred approach, these control features are adjusted such that each initiator starts substantially one chain (dependent upon initiator efficiency), each chain is initiated at substantially the same time, and each chain grows at substantially the same rate (within statistical variations with respect to initiation and propagation). Additional discussions about each of these control features is presented below.

The amount of stable free-radical control agent used in the invention is preferably controlled. In a preferred approach, the amount of stable free radical control agent (e.g., on a molar basis) corresponds substantially to, and preferably matches, the amount of propagating polymer chains (e.g., on a molar basis) throughout the duration of the polymerization reaction. Without being bound by theory, since a certain statistical fraction of propagating, living polymer control chains will terminate during a radical polymerization reaction, the stable free radical control agents of the present invention have a mechanism available for destruction of a statistical fraction of the stable free radical (e.g., through a decomposition reaction or a neutralization reaction)— thereby maintaining the preferred correspondence between the number of control agent molecules and the number of propagating chains. In this context, the phrase "decomposition reaction" refers to the stable free radical control agent reacting with itself or with another stable free radical control agent to yield a product or products that does not have a free radical or is not a stable free radical. Similarly, in this context, the phrase "neutralization reaction" refers to the free radical control agent reacting with a reagent added to the polymerization reaction that removes or destroys the free radical associated with the control agent. In some embodiments, the X moiety allows the free radical to destabilize itself (i.e., a decomposition reaction) so that the control agent has a limited lifetime, or is destabilized by the addition of a reagent (i.e., a neutralization reaction). Hence, the use of nitroxide control agents offers benefits associated with living kinetics—such that molecular weight control is realizable (e.g., linear increase in molecular weight as a function of conversion), and architectural flexibility is maximized (see below). The controlled free radical polymerizations of the invention provide a high degree of control over molecular weight, particularly at high molecular weight (e.g., greater than about 75,000), and typically with narrow molecular weight distribution (polydispersity index ($M_W/M_N$) generally not more than about 2.0 and typically between 1.1 and 1.8, as discussed above). Such control translates directly into beneficial applications, as discussed above.

Hence, according to the preferred approach, the amount of stable free-radical control agent can be determined for a given architecture as follows. The number (e.g., moles) of initiators per target polymer molecule is determined based on architecture design (discussed in greater detail below), and then multiplied by the number (e.g., moles) of target polymer molecules, to obtain the total number (e.g., moles) of initiator in the reaction mixture. The number (e.g. moles) of stable free radical control agent molecules is, in the preferred method, then matched to the total number (e.g., moles) of initiator in the reaction mixture. Hence, the molar ratio of control agent to initiator is preferably about 1:1, assuming an initiator efficiency of about 1. When the preferred control agent—initiator adduct is employed in the polymerization reaction, a 1:1 ratio of initiator to control agent is established as a matter of course, based on equivalents. For lower initiator efficiencies, however, the amount of control agent can be appropriately adjusted. The relative amount of control agent to initiator can be adjusted, for example, by the adjusting (increasing or decreasing relative to the 1:1 balance) the amount of free radicals (initiators and/or control agents) in the reaction mixture. Such adjustments can be from several sources, including, for example, stable free radical control agent, control agent precursors, additional free radical initiators, initiator precursors, or radicals derived from other reactions.

Although a 1:1 ratio of free-radical initiator and control agent is generally preferred, other ratios are also contemplated. In general, the ratio of free-radical initiator to free-radical control agent, based on equivalents—and assuming the amount of initiator is approximately equivalent to the number of radical produced (i.e., initiator efficiency of about 1)—can typically range of from about 1:0.1 to about 1:4, more preferably from about 1:0.3 to about 1:2 and most preferably from about 1:0.4 to about 1:1.6.

The monomer to initiator ratio can vary depending upon the particular architecture of interest, the desired molecular weight, the initiator efficiency and the conversion. For each polymer arm extending from a multi-arm core (e.g., of a star polymer), for example, the monomer to initiator ratio can range from about 10:1 to about 1,000,000:1, more preferably from about 50:1 to about 500,000:1 and most preferably from about 100:1 to about 100,000:1, by mole, assuming an initiator efficiency of about 1 and about 100% conversion.

When an accelerator is present, the ratio of free radical control agent to accelerator can range from about 1:0.1 to about 1:4, more preferably from about 1:0.3 to about 1:2 and most preferably from about 1:0.4 to about 1:1.6, by mole.

Polymerization reaction conditions to be controlled include temperature, pressure, reaction time, and head-space atmosphere, among others. The temperature can generally range from about 0° C. to about 300° C., preferably from about 0° C. to about 200° C., more preferably from about 20° C. to about 150° C., and most preferably from about 70° C. to about 130° C. The reaction pressure can vary from atmospheric pressure to about 100 atmospheres, and preferably from about atmospheric pressure to about 10 atm. The atmosphere of the reaction-vessel head-space, above the polymerization mixture, can air, nitrogen, argon or another suitable atmosphere. The polymerization reaction time can range from about 0.1 hours to about 72 hours, preferably from about 0.5 hours to about 36 hours, and more preferably from about 1 hour to about 24 hours. The polymerization reaction conditions can be established, in general, prior to or after the reaction components (free-radical initiator or precursor thereof, control-agent initiator or precursor thereof and monomer) are combined.

The polymerization reaction is exemplified in Examples 2A through 2E.

Post-Reaction Workup

A number of different workup procedures can be used to purify the polymer of interest. Briefly, such approaches include: (i) precipitation, and fractionating reprecipitation of the polymers; (ii) membrane separation (e.g., aqueous dialysis) of the polymers; and/or (iii) freeze-drying of the polymers.

Linear Polymers

Linear polymers can be prepared using the nitroxide-mediated, living free radical methods described above, according to several possible schemes. (FIGS. 4A through 4D).

In one approach (FIG. 4A), a free radical initiator, I., is added to a reaction vessel comprising stable free radical control agent, C., and monomer, M, to form a reaction mixture. The initiator then reacts with the monomer under polymerization conditions to form a linear polymer.

In another approach (FIG. 4B), an initiator-control agent adduct, I-C, is added to a reaction vessel comprising monomer, M, to form a reaction mixture. The free-radical initiator and stable free-radical control agent are formed in situ, and the free-radical initiator then reacts with the monomer under polymerization conditions to form a linear polymer.

In a further approach, (FIG. 4C), a two-arm initiator, .I-CORE-I., is added to a reaction vessel comprising stable free radical control agent, C., and monomer, M, to form a reaction mixture. Each of the initiators on the core then reacts with monomer under polymerization conditions to propagate a polymer chain from each initiation site, and to thereby form a linear polymer.

In yet an additional approach, (FIG. 4D), a two-arm initiator-control agent adduct, C-I-CORE-I-C, is added to a reaction vessel comprising monomer, M, to form a reaction mixture. Core-bound free-radical initiators and stable free-radical control agents are formed in situ, and each of the free-radical initiators then react with the monomer under polymerization conditions to propagate a polymer chain from each initiation site, and to form a linear polymer. A more detailed discussion of a multi-arm intiator—for the general case—is presented below in connection with the discussion of star polymers.

The latter two approaches (FIG. 4C, FIG. 4D) are preferred with respect to forming a linear polymer having a desired target molecular weight with a relatively low polydispersity index, since the polydispersity index is directly related to the number of propagation steps (i.e., degree of polymerization) from each initiation site.

Linear copolymers can be formed according to these approaches by appropriate control of the monomer during chain propagation. For example, a random copolymer can be formed by incorporating two or more different monomers into the reaction mixture. A block copolymer can be formed by reaction with a first monomer to depletion, then reacting with a second monomer.

Star Polymers

Generally, multifunctional initiators are preferably used for the formation of star architectures. Multi-functional initiators may be characterized by the following general formula (VI):

$$(Core)_z\text{-}(YE)_d \tag{VI}$$

where (Core) is the core and YE is the initiator, such that the YE bond is labile enough to reversibly or irreversibly cleave through a radical mediated reaction, heat or UV light thereby forming initiating sites (sometimes referred to herein as "i"). In addition, z is defined above, but is typically 1 or more and d is 2 or more. In other embodiments discussed below, incorporating into a polymer or polymer fragment backbone a monomer functionalized with initiators or initiator-control agent adducts can form a multi-functional initiator.

In some embodiments, the YE initiator is incorporated into a polymer fragment or backbone and can be characterized by the general formula (VII): $P\text{-}(YE)_d$ where P is a polymer or polymer fragment (e.g., an oligomer). This general formula is shown schematically in FIGS. 6A and 6D. These same multi-functional initiators may also be used in the branched embodiments of this invention, but for star architecture, d will be equal to the number of arms desired and typically is either 4, 6, 8, 12 or more. For branching embodiments, d may vary more widely. Moreover, those of skill in the art will appreciate that the combination of multi-functional initiators when used in conjunction with second monomers that are functionalized (discussed below) and/or macromonomers (discussed above), branching of the arms of a star is readily possible as well as hyper-branching architecture polymers.

More specifically, some embodiments of this invention will employ a multi-functional initiator that may be characterized by the general formula (VIII):

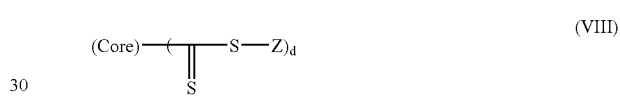

wherein core is a core molecule, S is sulfur and Z is selected from the group consisting of amino and alkoxy, as defined above. In addition, d is 2 or more, preferably 4 or more and even more preferably 6 or more. In specific embodiments, d may be 3, 4, 5, 6, 7 or 8.

In the multifunctional initiators herein, the core molecule may be a polymer that incorporates the initiator portion into the backbone or one or more chains of the polymer or may be a multi-functional molecule. More specific examples of these types of cores include:

where YE, d, $R^5$ and $R^6$ are as defined above and g is 2 or more.

Thus, using these types of core molecules, more specific examples of multi-functional, non-nitroxide initiators include:

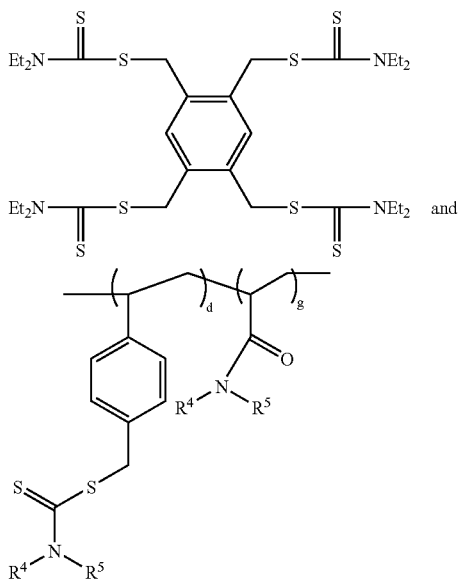

where d, g, R[5] and R[6] are as defined above.

The core of the multi-functional agents described herein may also be a dendritic molecule, with specific examples shown in FIGS. 2D and 2E.

In addition, the core may also be a polymerized cross-linked molecule. In a cross-linked embodiment, the core is polymerized using living type free radical polymerization techniques known to those of skill in the art with at least two different monomers, one of which is a bi-functional monomer (the most preferred bi-functional monomer is dimaleimid, with other bifunctional monomers being discussed herein). The other monomer is a mono-functional monomer (a preferred second monomer is styrene). The bi-functional and mono-functional monomers are chosen so that the first monomer has a higher affinity for the second monomer (as compared to the affinity for itself) and the second monomer has a higher affinity for the first monomer (also as compared to the affinity for itself). Because of this alternating affinity, when the two monomers are polymerized, a highly cross-linked core is formed. The ratio of bi-functional monomer to mono-functional monomer, as well as initiator concentration, polymerization control method and concentrations will vary according to the core that is desired. In some embodiments, the core is formed with a desired number of arms on it, but not so large as to precipitate out of the polymerization solution. Controlling the concentration of bi-functional monomer typically controls the number of arms. Since core polymerization is a "living" process, the end result of the core polymerization process is a core that has arms on it that have "living" kinetics, meaning that by adding more monomer, the arms can be grown to a desired length (measured in molecular weight). In a radical mediated mechanism, the control agent caps the ends of the arms, so that a free radical is present when the control agent un-caps the arms under polymerization conditions. After the core is polymerized to a desired size (e.g., the desired number of arms or molecular weight), the monomer used for its separation ability is added to grow the arms to the desired molecular weight. For example, N,N-dimethylacrylamide may be used.

In the case of star polymers, polyfunctional nitroxide initiators capable of initiating multiple free radical polymer-izations are particularly preferred. Such initiator-control agent adducts include, for example, polyfunctional adducts of the formula XII:

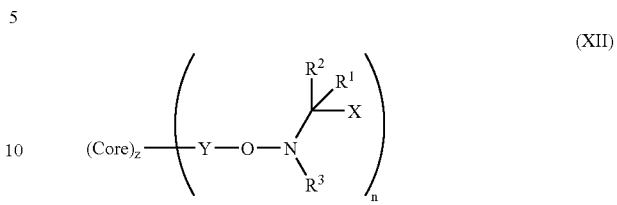

where n ranges from 2 to about 100, preferably from 2 to about 50, more preferably from 2 to about 20, and/or the other specific ranges set forth above in connection with the star-polymer discussion, Core represents a polyfunctional core molecule, and each of Y, R[1], R[2], and R[3] are as described above. Hence, when n=2, the polyfunctional adduct characterized by the above formula is a two-arm initiator, such as is represented schematically in FIG. 4D and discussed above in connection therewith. More specifically, Core is a polyfunctional core molecule; Y is a residue capable of initiating a free radical polymerization upon homolytic cleavage of the Y—O bond, the residue being selected from the group consisting of fragments derived from a free radical initiator, alkyl, substituted alkyl, alkoxy, substituted alkoxy, aryl, substituted aryl, and combinations thereof; X is a moiety that is capable of destabilizing the control agent on a polymerization time scale; and each R[1] and R[2], independently, is selected from the group consisting of alkyl, substituted alkyl, cycloalkyl, substituted cycloalkyl, heteroalkyl, heterocycloalkyl, substituted heterocycloalkyl, aryl, substituted aryl, heteroaryl, substituted heteroaryl, alkoxy, aryloxy, silyl, boryl, phosphino, amino, thio, seleno, and combinations thereof; and R[3] is selected from the group consisting of tertiary alkyl, substituted tertiary alkyl, aryl, substituted aryl, tertiary cycloalkyl, substituted tertiary cycloalkyl, tertiary heteroalkyl, tertiary heterocycloalkyl, substituted tertiary heterocycloalkyl, heteroaryl, substituted heteroaryl, alkoxy, aryloxy and silyl; and z=1 or more and n is at least 2.

Schematically, preparation of a star polymer, such as a 4-arm star, is shown in FIG. 5A. Briefly, a four-arm initiator, CORE-(IC)$_4$, is added to a reaction vessel comprising monomer, M, to form a reaction mixture. Core-bound free-radical initiators and stable free-radical control agents are formed in situ, and each of the free-radical initiators then react with the monomer under polymerization conditions to propagate a polymer chain from each initiation site, and to form a 4-arm star polymer. Following initiation, the growth of each arm is controlled by the same living kinetics described above for the general case, making it possible to assemble star polymers whose arms include individual homopolymers as well as di, tri or higher order block copolymers, or random copolymers.

A variation of the aforementioned approach for preparation of a 4-arm star is shown schematically in FIG. 5B. Briefly, a four-arm initiator, CORE-(I.)$_4$, is added to a reaction vessel comprising stable free radical control agent, C., and monomer, M, to form a reaction mixture. Each of the initiators on the core then reacts with monomer under polymerization conditions to propagate a polymer chain from each initiation site, and to thereby form a 4-arm star polymer.

In an alternative, less preferred, approach (FIG. 5C), multi-arm polymers are formed by growing end-functionalized linear oligomers or polymers (e.g., in a manner analogous to the methods described above in connection with FIG. 4A through FIG. 4D), I-POLYMER-f. The functionalized oligomer or polymer is then reacted with a multi-functionalized core molecule, CORE-(f)$_4$, to form a four-arm star polymer.

Although controlled, living free radical polymerization is a preferred method that is general to all of the polymers of the invention, it is contemplated some of the controlled-architecture polymers—particularly linear polymers and star-polymers—can be prepared using other polymerization approaches. Although the robustness, applicability and/or control through such other mechanisms may not compare favorably with controlled, living free radical approaches for some applications, these other approaches may be suitable in particular applications. Hence, linear polymers and star-polymers can be prepared, in the general case, by successive addition of monomer to a mulit-arm core (i.e., a polyfunctional core molecule) comprising two or more, and preferably three or more initiating units. In particular, anionic polymerization and cationic polymerization approaches can be employed for this reaction scheme.

Branched Polymers

Branched polymers can be prepared by several approaches. Preferred approaches can generally be classified as "grafting from" or "grafting onto" approaches.

Figure 6A:
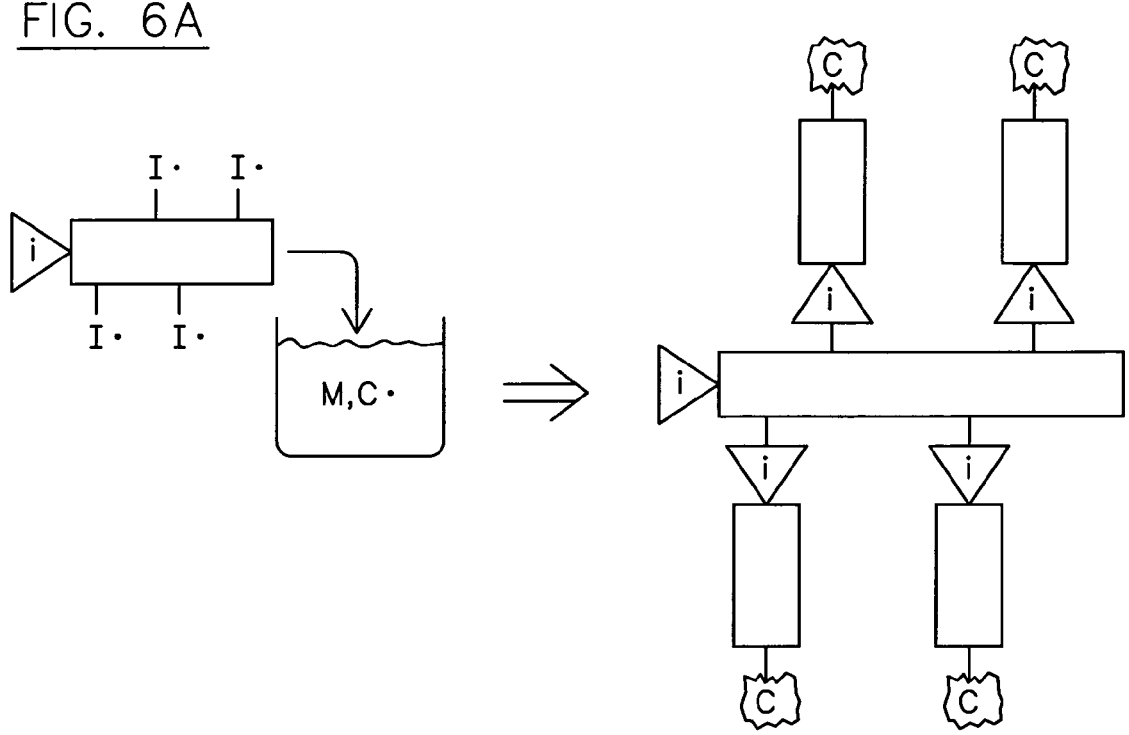
FIGS. 6A through 6D are schematic representations of various schemes for preparing branched or grafted polymers. In these figures, "I." represents a free radical initiator, M represents monomer, "C." represents a stable free radical control agent, "I-C" or "C-I" represent an initiator-control agent adduct, "f" represents a functional group, "CORE" represents a poly-functional core molecule, "i" represents a free-radical initiator fragment (i.e., initiation site), the "C" within squiggly lines represents a "living" control agent end-group of a polymer chain, and the rectangular boxes represent linear chains or segments of polymer.

With reference to FIG. 6A, according to one "grafting from" approach, linear oligomers or polymers having initiator-functionalized side groups, are formed—preferably in a manner analogous to the methods described above in connection with FIG. 4A through FIG. 4D, I-POLYMER-(I.)$_n$. The initiator-functionalized oligomer or polymer is added to a reaction vessel comprising stable free radical control agent, C., and monomer, M, to form a reaction mixture. Each of the initiators then reacts with monomer under polymerization conditions to propagate each of the chains and to form a branched polymer.

Figure 6B:
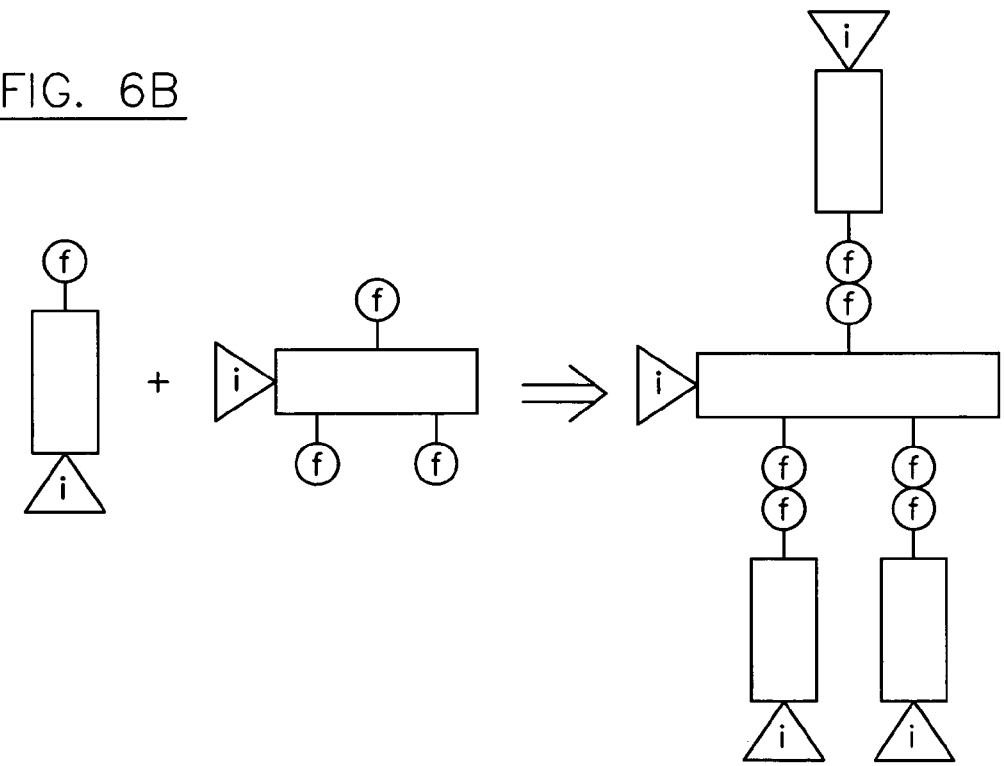

In a less preferred, "grafting onto" approach (FIG. 6B), a branched polymer is formed by growing end-functionalized linear oligomers or polymers (e.g., in a manner analogous to the methods described above in connection with FIG. 4A through FIG. 4D), I-POLYMER-f. The functionalized oligomer or polymer is then reacted with a linear oligomer or polymer having functionalized side groups to form a branched polymer.

In another approach (FIG. 6C), a macromolecular branched polymer can be formed by a "graft onto" method. Linear oligomers or polymers having vinyl-functionalized end groups (i.e., having a carbon-carbon double bond) are formed—preferably in a manner analogous to the methods described above in connection with FIG. 4A through FIG. 4D, and used as a co-monomer (typically in much smaller concentrations) with the monomer of choice for a main chain. The vinyl-functionalized oligomer or polymer, as well as the second, main monomer, are then reacted with initiator in the presence of a control agent to form the branched polymer.

Figure 6C:
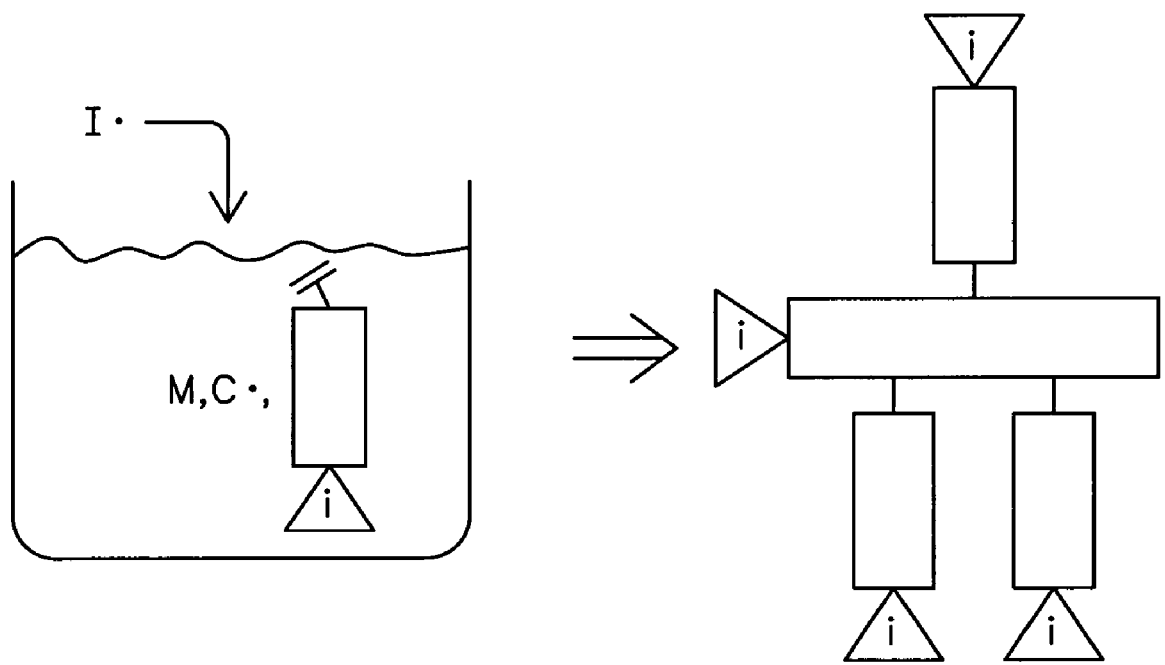
Figure 6D:
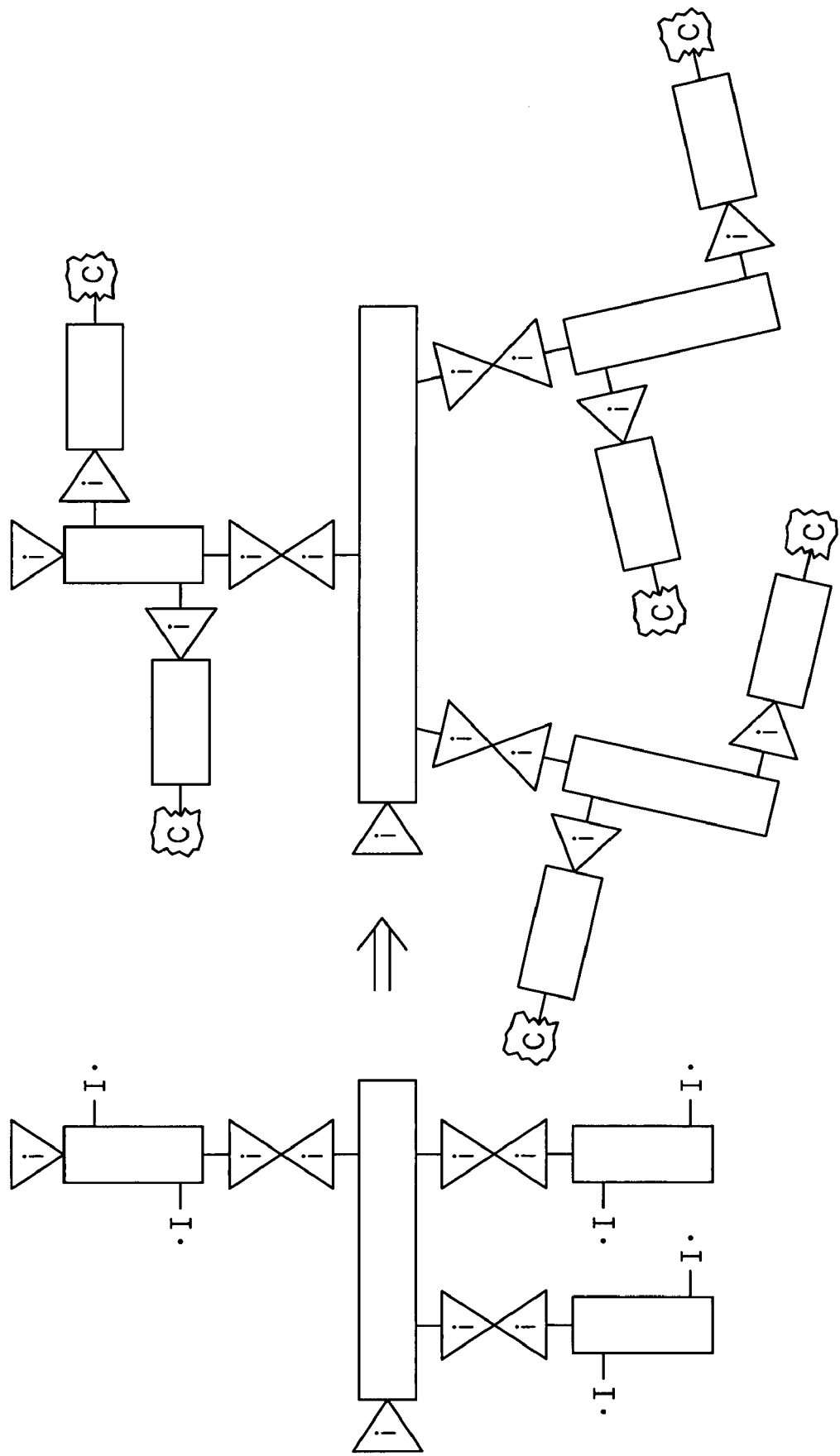

A graft-on-graft polymer can be formed as shown schematically in FIG. 6D, based on a variation of the approach outlined in connection with the discussion of FIG. 6C. Briefly, a branched polymer having initiator-functionalized side groups is formed based on the methods detailed above or by other methods. The branched polymer is then added to a reaction vessel comprising stable free radical control agent, C., and monomer, M, to form a reaction mixture. Each of the initiators then reacts with monomer under polymerization conditions to propagate each of the chains and to form a branch-on-branch (graft-on-graft) polymer.

In another embodiment shown generally by FIGS. 6C and 6D, a monomer having one polymerizable end (typically a vinylic group) also includes an initiator and/or an initiator-control agent adduct. This monomer, referred to herein as a "second" monomer and may be characterized by the general formula (XIII): M-YE (where M is the monomer atoms and YE is as discussed above) or formula (XIV): M-I-C monomer (where M is the monomer portion and I-C is as discussed above, e.g., initiator-control agent adduct) and M includes a vinylic moiety. These second monomers may be used in a two step polymerization embodiment or a one step polymerization embodiment. In the two step embodiment, the second monomer is used as a second monomer in a first part of the polymer synthesis method in order to form the backbone of the polymer with at least one first monomer (the vinylic moiety in the monomer portion in the M-YE or M-I-C molecule polymerizes, typically with additional monomer added in to spread out the initiator portion of the molecule along the polymer backbone). This backbone thus contains additional initiator and/or initiator-control agent, which is used in the second part of the polymerization process, namely polymerization of a desired monomer to a desired molecular weight in a polymerization system using the initiator and control agent present in the backbone. In some embodiments, the YE portion or I-C portion is protected in the first part of the polymerization to avoid reaction. In some other embodiments, the YE or I-C portion of the monomer is subsequently added to specified second monomers. In the one step embodiment, the second monomer is put into the same polymerization system as the desired monomer (as a specified ratio, such as 90% at least one first monomer and 10% second monomer; other ratios between monomers can be used to control the amount of branching, but is preferably in the range of at least one first monomer to second monomer of about 99:1 to about 85:15, and more preferably in the range of from about 99:1 to about 90:10). The free radical polymerization is started so that the second monomer is randomly incorporated into the polymer, but also serves to grow polymer branches from the points at which the molecule is incorporated. This forms a random hyper-branched polymer. This process has been used to polymerize N,N-dimethylacrylamide with a control agent and initiator attached to make a hyper-branched polymer useful as a separation media for DNA capillary electrophoresis. These second monomers, when incorporated into a polymer or polymer fragment (e.g., an oligomer), can fall within the definition of multi-functional initiator, discussed above.

The second monomers may also or alternatively be the general formula (XV):

(XV)

where Y, E and $R^4$ are as defined above; Other is as defined above in conjunction with macromonomers and generally is any other atoms in the monomer, but is preferably comprises up to 20 non-hydrogen atoms; and d is also defined above, e.g., is 1 or more, preferably 1 and alternatively 20 or more in a macromonomer embodiment (see formula I'). This general formula is shown schematically in FIGS. 6C and 6D. A specific example of a macromonomer of different molecular weights is shown in FIG. 3 and discussed in detail in Example 2H. Another general formula may characterize the second monomers, which would entail replacing the YE in the above formula with the initiator-control agent fragment shown in formula XII, above.

In conjunction with the processes discussed above, non-linear polymers of this invention may also be prepared by using multi-functional monomers (typically bi-functional monomers), as discussed above.

Of course, numerous other variations exist for preparing non-linear polymers that encompass the general approaches outlined in detail herein, and exemplified below.

Non-linear copolymers can be formed according to these approaches by appropriate control of the monomer during chain propagation, generally as described above in connection with linear polymers.

The following examples illustrate the principles and advantages of the invention.

EXAMPLES

Syntheses were carried out under an inert atmosphere in a glove box under a nitrogen or argon atmosphere. Polymerization experiments were generally carried out in 1 mL glass vials fitted in an aluminum block, and sealed with a Teflon faced silicon rubber gasket backed with a stainless steel lid, unless the conditions of the experiment indicate otherwise. Agitation was achieved by orbital shaking at five to six Hz. Heating was achieved using resistive heaters mounted onto the aluminum block. The total polymerization reaction volume was 0.4-0.6 mL. The starting components for polymerizations were delivered in aqueous or monomer solutions, and typical concentrations were 0.001 to 0.1 mol/L. In general the initiator was the last component added to the polymerizations. After the reactions had been heated for a predetermined time at a predetermined temperature, the complete contents of each reaction was disolved in 10 mL of water and analyzed by SEC (size exclusion chromatography). Size Exclusion Chromatography was performed using automated rapid GPC system. In the current setup we used dimethylformamide containing 0.1% of trifluoroacetic acid as an eluent and polystyrene-based columns. All of the molecular weight results obtained are relative to linear polystyrene standards. Monomers were degassed by applying three freeze-pump-thaw cycles.

Example 1

Preparation of Initiator-Control Agent Adducts

Example 1A

Synthesis of 6-Arm and 12-Arm Initiators

Synthesis of Methyl (3,5-ditetrahydropyranyloxy)benzoate, 1

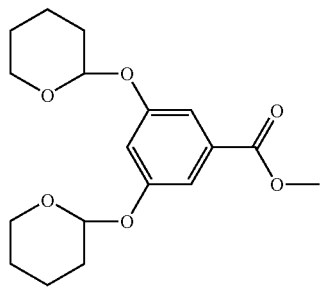

To a mixture of methyl 3,5-dihydroxybenzoate (25 g, 150 mmol) and 2,3-dihydro-2H-pyran (40 g, 450 mmol) in 250 ml of dichloromethane was added 4 drops of concentrated hydrochloric acid. The mixture was stirred overnight at room temperature. When conversion was complete (all the solid was dissolved) the crude product mixture was partitioned between water and dichloromethane. The aqueous phase was extracted three times with dichloromethane. The organic fractions were collected, dried ($MgSO_4$), filtered and then concentrated to dryness. The product was purified by chromatography using as eluant, 50 vol.-% petroleum ether in dichloromethane and then gradually changing to pure dichloromethane and eventually 5 vol.-% diethyl ether in dichloromethane. Yield 87%; $^1$H NMR ($CDCl_3$) δ 1.54-1.99 (m, 12H, $CH_2$), 3.58-3.62 (m, 2H) and 3.82-3.92 (m, 2H,) ($CH_2O$), 3.86 (s, 3H, $CH_3$), 5.42-5.46 (m, 2H, CH), 6.93-6.96 (m, 1H, ArH) and 7.34-7.36 ArH); $^{13}$C NMR ($CDCl_3$) δ 18.60 and 18.65, 25.15, 30.22, 52.16, 61.99 and 62.04, 96.30 and 96.46, 109.79 and 109.96 and 110.13 and 110.21, 110.86, 131.86, 157.87 and 157.94 and 166.82 (double peaks correspond to different diastereomers).

Synthesis of 3,5-ditetrahydropyranyloxy benzyl alcohol, 2

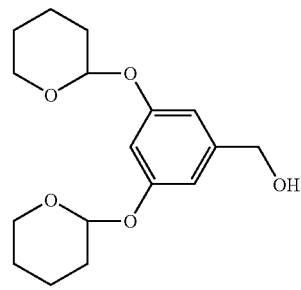

To a suspension of lithium aluminum hydride (9.5 g, 250 mmol) in 100 ml of anhydrous tetrahydrofuran was added dropwise a solution of 1 (42 g, 130 mmol) in 100 ml of anhydrous tetrahydrofuran. The mixture was stirred at room temperature under nitrogen. When conversion was complete (1 h) the reaction was quenched by slowly and carefully adding water dropwise until the gray solid turned white. The solid was filtered off by suction filtration and the filtrate evaporated to dryness. The crude product mixture was partitioned between water and dichloromethane. The aqueous phase was extracted three times with dichloromethane. The organic fractions were collected, dried ($MgSO_4$), filtered and then concentrated to dryness. The product was purified by chromatography using as eluant, pure dichloromethane and then gradually changing to 20 vol.-% diethyl ether in dichloromethane.

Yield 89%; $^1$H NMR ($CDCl_3$) δ 1.53-2.01 (m, 13H, $CH_2$ and OH) 3.53-3.61 (m, 2 H) and 3.82-3.92 (m, 2H)($CH_2O$), 4.58 (d, J=6.1, 2H, $ArCH_2$), 5.36-5.41 (m, 2H, CH), and 6.67 (s, 3H, ArH); $^{13}$C NMR ($CDCl_3$) δ 18.72 and 18.75, 25.20, 30.34, 62.01 and 62.05, 65.27, 96.33 and 96.47, 104.50 and 104.66, 108.14 and 108.18, 143.21, 158.24 and 158.30 (double peaks correspond to different diastereomers).

Synthesis of 3,5-ditetrahydropyranyloxy Benzyl Bromide, 3

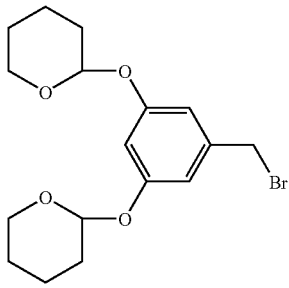

To a solution of 2 (2.0 g, 6.5 mmol), carbon tetrabromide (2.4 g, 7.2 mmol) and N,N-diisopropyl ethylamine (1.2 ml, 7.2 mmol) in 50 ml of dichloromethane was added in portions triphenylphosphine (1.9 g, 7.2 mmol). After stirring at room temperature until conversion was complete (2 h) the reaction was quenched with 2 ml of water. The crude product mixture was partitioned between water and dichloromethane. The aqueous phase was extracted three times with dichloromethane. The organic fractions were collected, dried (MgSO$_4$), filtered and then concentrated to dryness. The product was purified by chromatography using as eluant, 50 vol.-% petroleum ether in dichloromethane and then gradually changing to pure dichloromethane. The product was stored at less than 0° C. Yield 68%; $^1$H NMR (CDCl$_3$) δ 1.49-1.98 (m, 12H, CH$_2$), 3.50-3.55 (m, 2H) and 3.78-3.88 (m, 2H)(CH$_2$O), 4.31 (d, J=10.1, 1H) and 4.36 (d, J=11.2, 1H)(CH$_2$Br), 5.32-5.35 (m, 2H, CH), and 6.64-6.67 (m, 3H, ArH); $^{13}$C NMR (CDCl$_3$) δ 18.65 and 18.68, 25.19, 30.30, 33.62, 61.97, 96.37 and 96.50, 105.21 and 105.44, 110.39 and 110.48, 139.46 and 158.21 (double peaks correspond to different diastereomers).

Synthesis of 4:

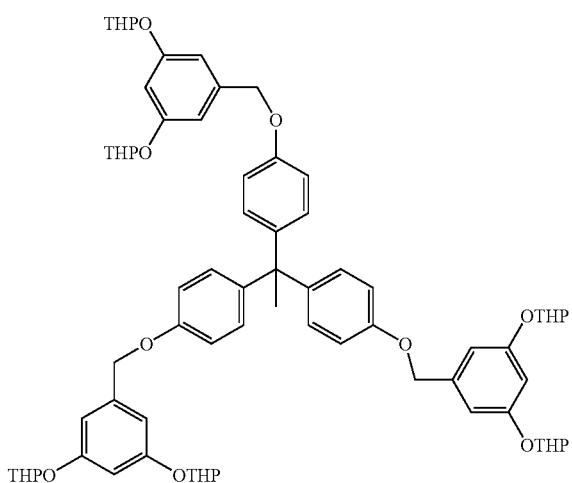

4

A mixture of 3 (5.0 g, 13.5 mmol), 1,1,1-tris-(4-hydroxyphenyl)-ethane (1.25 g, 4.08 mmol), potassium carbonate (10 g, 57.9 mmol), 18-crown-6 (0.10 g, 0.30 mmol) in 250 ml of acetone was refluxed under nitrogen overnight. The mixture was concentrated to dryness. The crude product mixture was partitioned between water and dichloromethane. The aqueous phase was extracted three times with dichloromethane. The organic fractions were collected, dried (MgSO$_4$), filtered and concentrated to dryness. The product was purified by chromatography column using as eluant, pure dichloromethane and changing to 5 vol.-% diethyl ether in dichloromethane. Yield 90%;

Synthesis of 5:

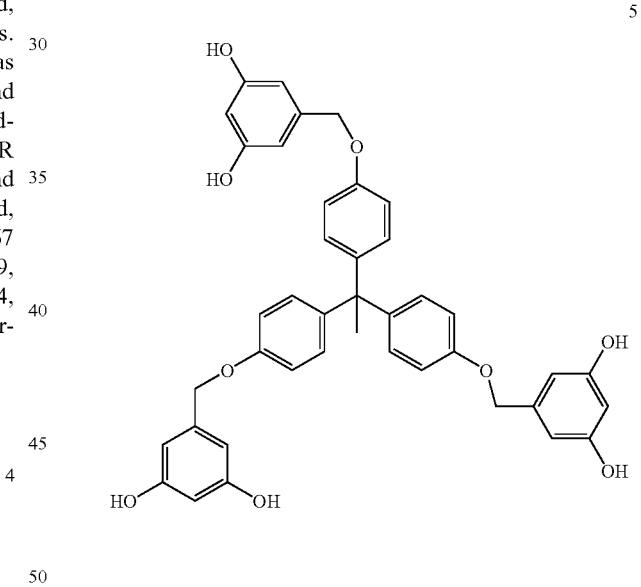

5

To a solution of 4 (4.3 g, 3.65 mmol) in 150 ml of methanol (50 ml of THF was added to aid dissolution) was added p-toluenesulfonic acid monohydrate (14 mg, 0.071 mmol). The reaction mixture was stirred until conversion was complete (3.5 h) and then potassium bicarbonate (36 mg, 0.35 mmol) was added and stirred for another ten minutes. The reaction mixture was concentrated to dryness. The crude product was purified by chromatographic column using as eluant, 10 vol.-% methanol in dichloromethane, changing to 15 vol.-% methanol in dichloromethane. Yield 95%;

Synthesis of 6

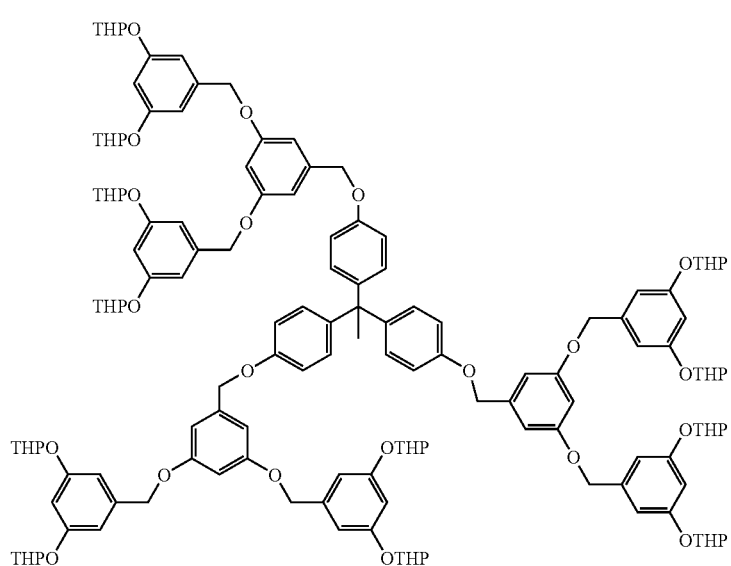

A mixture of 3 (4.4 g, 12 mmol), 5 (1.22 g, 1.8 mmol), potassium carbonate (5 g, 35.7 mmol), 18-crown-6 (0.10 g, 0.30 mmol) in 100 ml of acetone was refluxed under nitrogen overnight. The mixture was concentrated to dryness. The crude product mixture was partitioned between water and dichloromethane. The aqueous phase was extracted three times with dichloromethane. The organic fractions were collected, dried ($MgSO_4$), filtered and concentrated to dryness. The product was purified by chromatography column using as eluant, pure dichloromethane and slowly changing to 10 vol.-% diethyl ether in dichloromethane.

Synthesis of 7

To a solution of 6 (2.0 g, 0.83 mmol) in 100 ml of was added p-toluenesulfonic acid monohydrate (20 mg, 0.1 mmol). The reaction mixture was stirred overnight. Potassium bicarbonate (20 mg, 0.2 mmol) was added and stirred for another 10 minutes. The reaction mixture was concentrated to dryness. The crude product was purified by chromatographic column using as eluant, 5 vol.-% methanol in dichloromethane, changing slowly to changing to 15 vol.-% methanol in dichloromethane. Yield 90%;

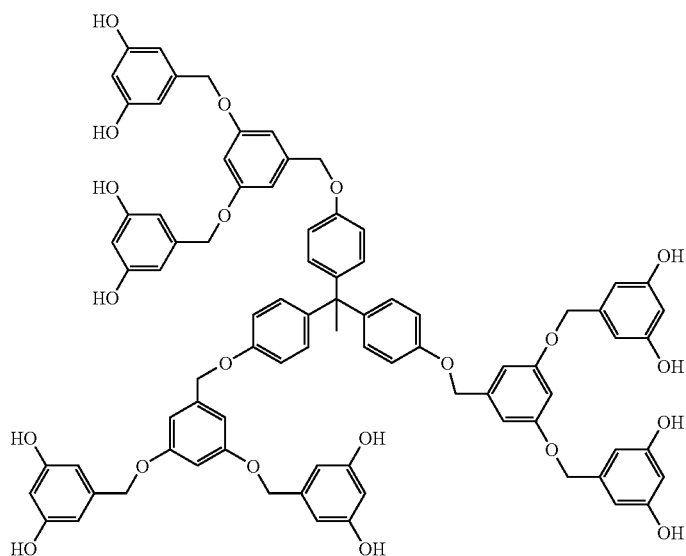

Synthesis of 6-arm-initiator

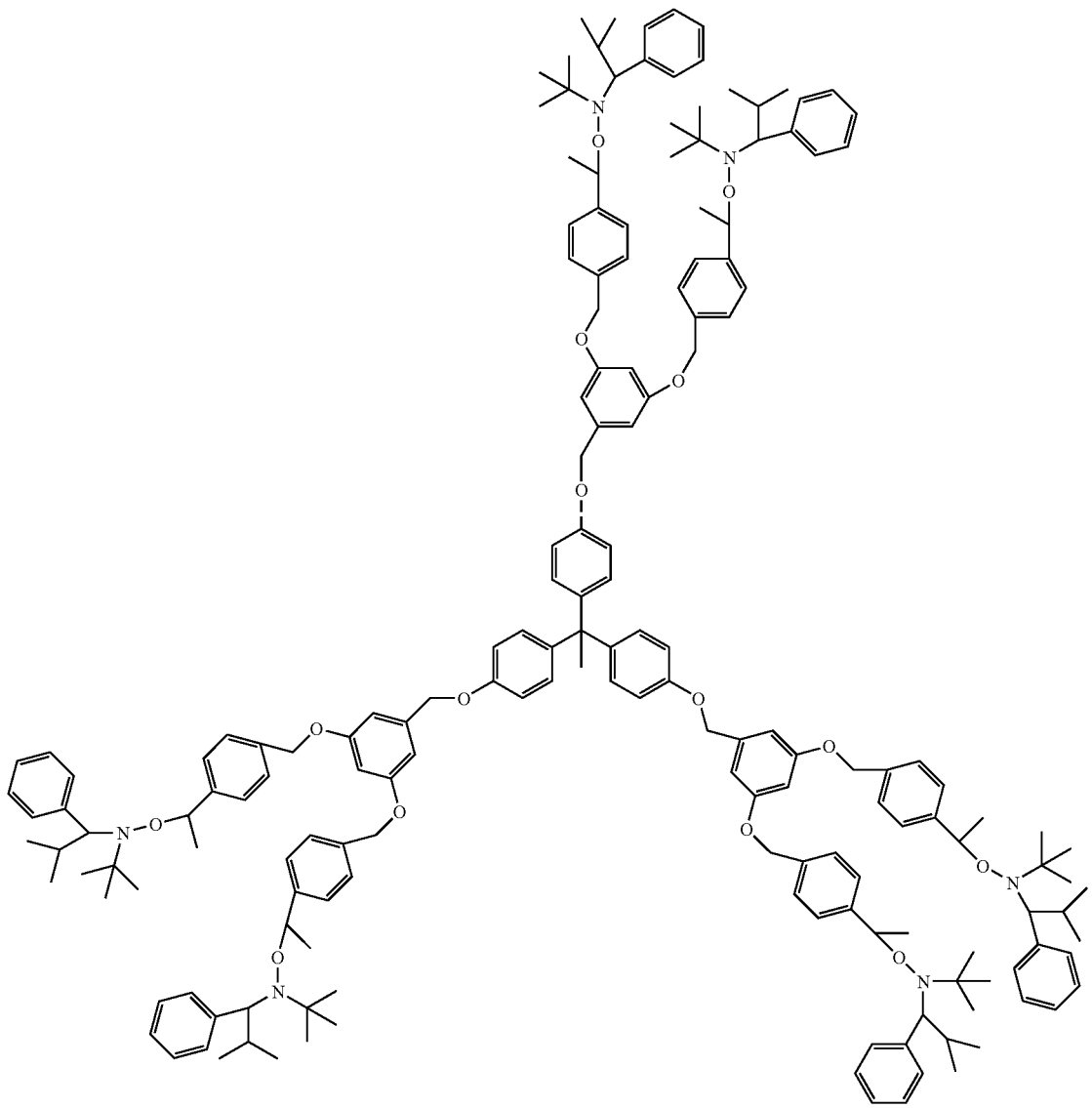

A mixture of 5 (0.5 g, 0.74 mmol), 8 (1.84 g, 5.95 mmol), potassium carbonate (4 g, 28.6 mmol), 18-crown-6 (0.10 g, 0.30 mmol) in 50 ml of acetone was refluxed under nitrogen for 24 hr.

The mixture was concentrated to dryness. The crude product mixture was partitioned between water and dichloromethane. The aqueous phase was extracted three times with dichloromethane. The organic fractions were collected, dried (MgSO$_4$), filtered and concentrated to dryness. The product was purified by chromatography column using as eluant, 1/1 petroleum ether/dichloromethane and slowly changing pure dichloromethane.

8

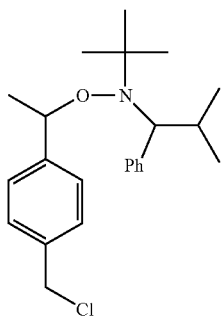

Synthesis of 12-arm-initiator
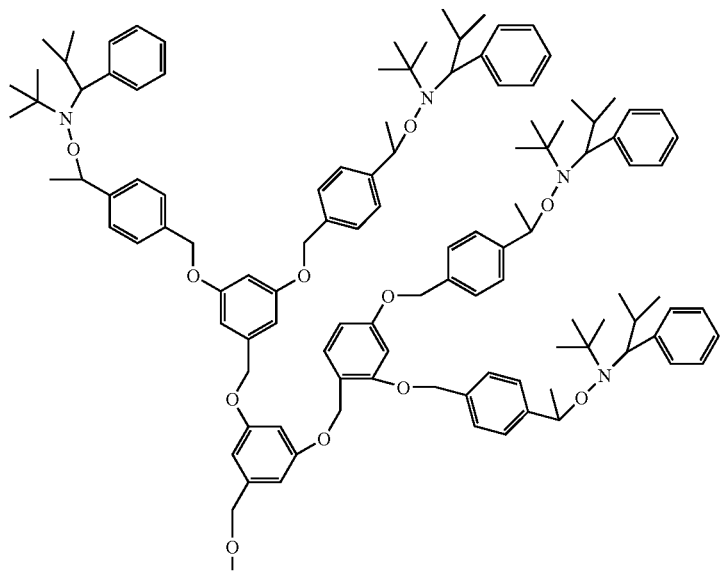
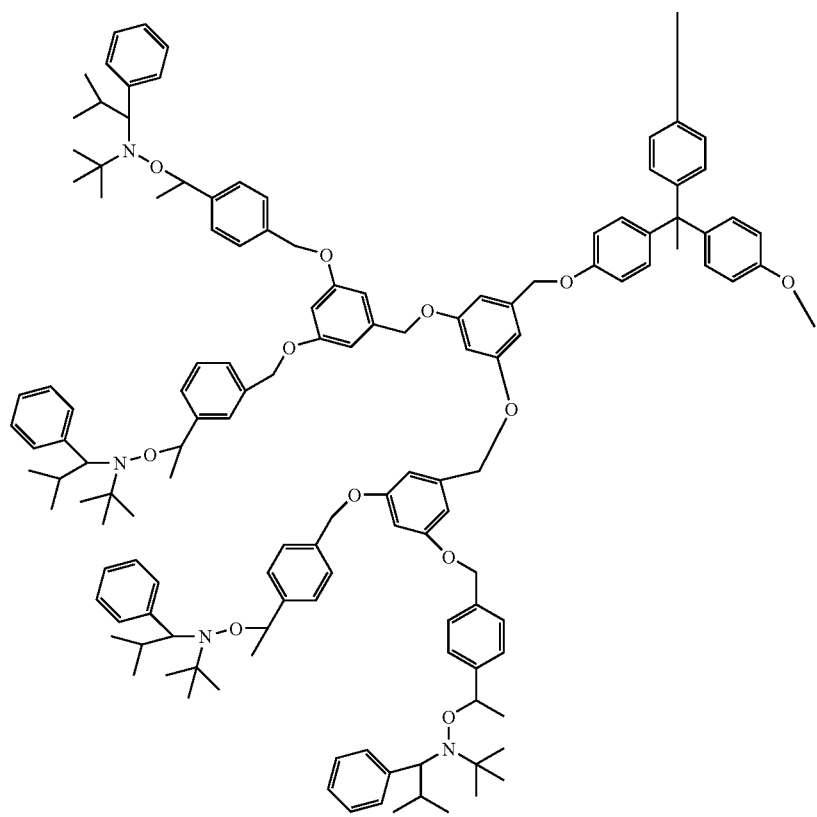

-continued

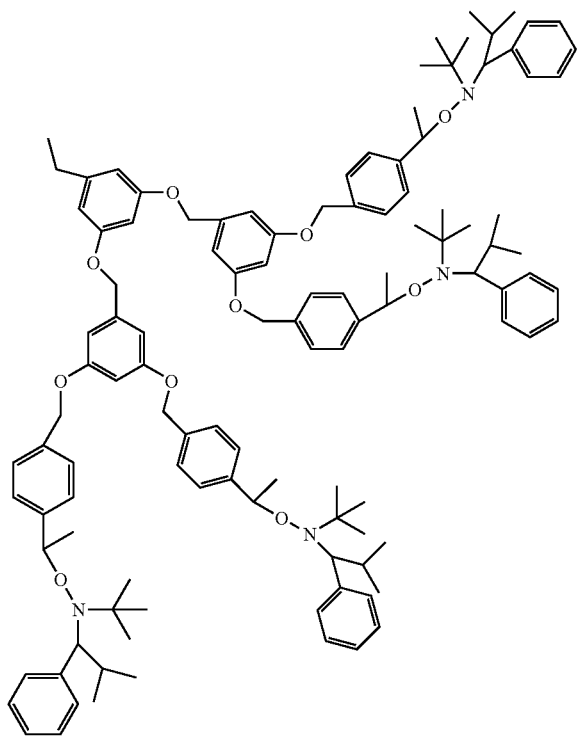

A mixture of 7 (0.6 g, 0.43 mmol), 8 (2.40 g, 6.41 mmol), potassium carbonate (4 g, 28.6 mmol), 18-crown-6 (0.10 g, 0.30 mmol) in 50 ml of acetone was refluxed under nitrogen for 24 hr. The mixture was concentrated to dryness. The crude product mixture was partitioned between water and dichloromethane. The aqueous phase was extracted three times with dichloromethane. The organic fractions were collected, dried ($MgSO_4$), filtered and concentrated to dryness. The product was purified by chromatography column using as eluant, 1/1 petroleum ether/dichloromethane and slowly changing pure dichloromethane.

Example 1B

Synthesis of 2-arm-initiator

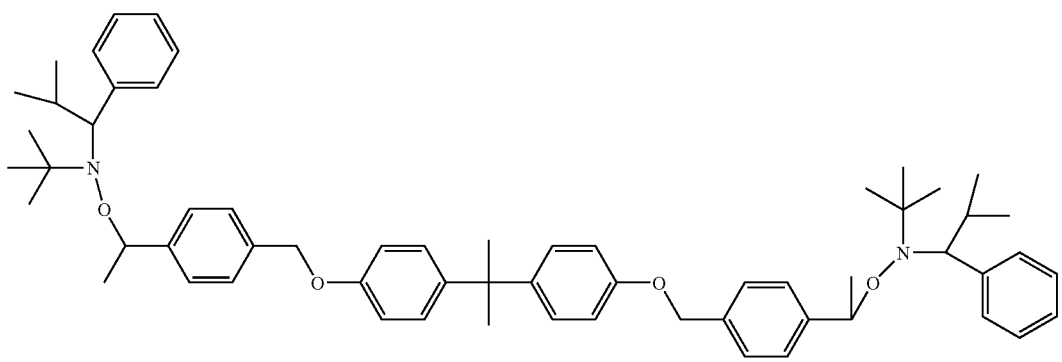

The 2-arm initiator is prepared similar to the corresponding 6- and 12-arm compound, as just discussed, but starting with bisphenol-A.

Example 1C

Synthesis of 1-arm initiator

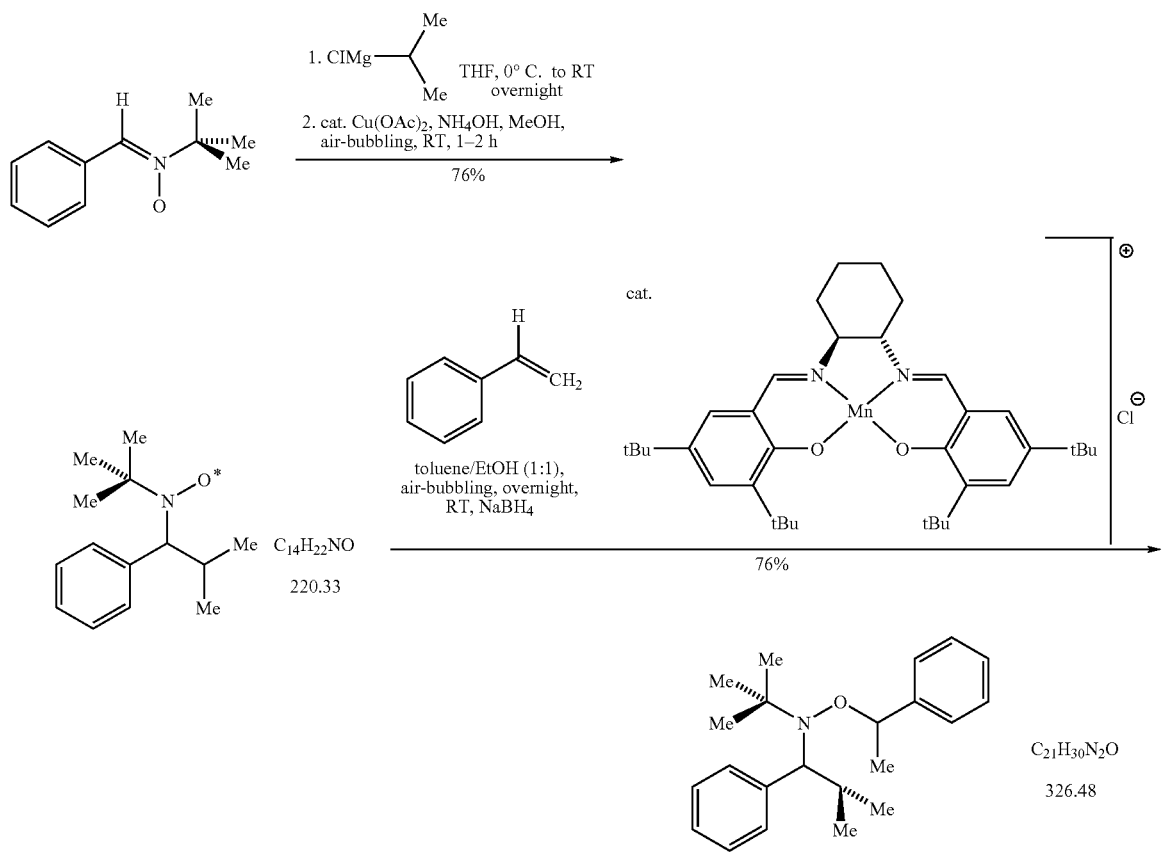

Procedures in these examples were performed substantially in accord with the following literature, which are incorporated herein by reference for all purposes:

C. J. Hawker et al., *J. Am. Chem. Soc.* 1999, 121, 3904-3920.

C. J. Hawker et al., *J. Polym. Sci. Part A: Polym. Chem.* 1998, 36, 2161-2167.

An oven- and flame dried 25 mL Schlenk-flask with stirring bar, rubber septum was charged under argon atmosphere with 355 mg (5.0 mmol) of N-tert-Butyl-α-phenylnitrone, and the nitrone was dissolved in 10 mL of anhydrous THF at room temperature. The yellowish solution was cooled to ca. 0° C. (ice bath) and isopropylmagnesium chloride (2 M in THF, 2.0 mL, 4.0 mmol) were added dropwise at this temperature with a syringe. The reaction mixture was stirred overnight with warming to room temperature (bright yellow to brownisch clear solution). Both, t.l.c. and GC/MS (M+=221) showed formation of the intermediate hydroxylamine and the corresponding nitroxide (M+=220). The reaction was quenched by addition of 10 mL of sat. aq. NH4Cl solution and the solvent was evaporated under reduced pressure. The residue was diluted in ether (20 mL) and the aqueous phase was extracted twice with 10 mL of ether. The combined organics were washed subsequentely with 20 mL of each water and sat. aq. NaCl solution, dried over MgSO4, filtered and evaporated. Although the crude product mixture is already of sufficient purity for the oxidation step, the products were isolated by flash chromatography on silica gel using EtOAc/hexanes (7:1) as an eluent to yield 378 g (85%) of an orange oil. Both, t.l.c. and GC/MS (vide infra) show that the crude product consists of the hydroxylamine and the corresponding nitroxide in a ration of ca. 1:1 due to air oxidation during work-up and purification.

A 100 mL round bottomed flask was charged with 375 mg (ca. 1.7 mmol based on hydroxylamine) of the product mixture (hydroxylamine and nitroxide) and the mixture was dissolved in 10 of MeOH of commercial quality at room temperature. Ca. 2 mL of an aq. solution of NH4OH (ca. 28%) and a spatula tip of Cu(OAc)2 were added. Through the vigiriously stirred reaction mixture was bubbled air at room temperature. The reaction mixture turned from yellow to dark blue-green within ca. 10 min. and the reaction was carried on for another 30 min. Upon completion (checked by t.l.c., GC/MS), the organic solvent was removed under reduced pressure, the residue was diluted with 50 mL of dichloromethane. The aqueous phase was extracted twice with 20 mL of dichloromethane and the combined organic were subsequently washed with each 50 mL of a 5-% aq. KHSO4 solution, sat. aq. NaHCO3 solution, water and sat. aq. NaCl solution. Drying over MgSO4, filtration, and evaporation followed by purification by column chromatography on silica gel using EtOAc/hexanes (1:19) as eluent (collection of the yellow fraction) yielded 332 mg (89%) of an deep orange viscous oil which solidified in the refrigerator (−20° C.). Both, GC/MS and $^1$H NMR spectroscopy in the presence of 2 eq. of pentafluorophenyl hydrazine showed homogeneity of the product obtained.

A 100 mL round-bottomed flask equipped with a stirring bar and a PE stopper penetrated by a long stainless steel needle (air inlet) and two short needles (air outlet) was charged with the nitroxide (661 mg, 3.0 mmol). EtOH/toluene (1:1) (30 mL) and Jacobsen's Mn-salen complex (286 mg, 0.45 mmol) were added. Subsequently, 473 mg (4.5 mmol, 485 μL) of 4-vinylpyridine were added via syringe followed by 227 mg (6.0 mmol) of NaBH$_4$. Through the (dark brown, cloudy) reaction mixture was bubbled air for ca. 12 h at room temperature. After filtration over a short plug of silica gel, EtOH and toluene removed under reduced pressure and the residue was dissolved in 25 mL of EtOAc/hexanes (1:1). The filter residue was washed with EtOAc/hexanes (1:1), and the organics were combined. The organics were washed with water and sat. aq. NaCl solution, dried (MgSO$_4$), filtration, and evaporated under reduced pressure. The alkoxymanie was eluted from the residue by means of MPLC with EtOAc/hexanes (1:4) to yield 747 mg (76%) of a dark yellow viscous oil. Purity and product homogeneity were determined by t.l.c. and $^1$H- and $^{13}$C NMR spectroscopy. $^1$H- and $^{13}$C NMR spectroscopy showed that the product was a mixture of diastereoisomers in a ratio of ca. 1:1.

Compound 8 was synthesized similar to the 1-arm initiator starting with 4-vinylbenzylchloride.

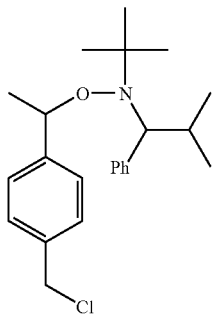

8

Example 2

Preparation of Controlled-Architecture Polymers

Example 2A

Preparation of 12-arm Star Polymer

Three stable free radical polymerization (SFRP) were carried out under bulk polymerization conditions. Each polymerization was designed to have the following final conditions for the growth of the star-shaped polymer: total volume of 0.4 mL, N,N-dimethylacrylamide as monomer, 0.00001, 0.0002 and 0.001 mole equivalence of initiator to monomer. The initiator used was the 12-arm dendrimer where each arm carries an adduct of the initiator/control agent (the organic soluble 2,2,5-trimethyl-3-(1-phenylethoxy)-4-phenyl-3-azahexane). This compound predetermines the control agent to initiator ratio to equal one. After dispensing the monomer and the initiator dissolved in monomer (0.002 mol/l) the reactor vessel was sealed and heated at 120° C. for 24 h. After the predetermined heating and agitation time the reactor vessels were cooled to room temperature and opened and the polymerization mixtures were worked up and characterized using the standard procedure outlined for polymerization experiments at the beginning of the Example section. Molecular weight and polydispersity index data of the 12-arm star polymers are presented in Table 1.

TABLE 1

| Initiator | Initiator to monomer ratio (per arm) | Target Mw | Obsv. M$_w$* | PDI |
|---|---|---|---|---|
| 12-arm | 1:10,000 | 12 M | 1.3 M | 1.92 |
| 12-arm | 1:5,000 | 6 M | 1 M | 1.90 |
| 12-arm | 1:1,000 | 1.2 M | 650k | 1.80 |

*M = millions, k = thousands

Example 2B

Preparation of 6-arm Star Polymers

Three stable free radical polymerization (SFRP) were carried out under bulk polymerization conditions. Each polymerization was designed to have the following final conditions for the growth of the star-shaped polymer: total volume of 0.4 mL, N,N-dimethylacrylamide as monomer, 0.00001, 0.0002 and 0.001 mole equivalence of initiator to monomer. The initiator used was the 6-arm dendrimer where each arm carries an adduct of the initiator/control agent (the organic soluble 2,2,5-trimethyl-3-(1-phenylethoxy)-4-phenyl-3-azahexane). This compound predetermines the control agent to initiator ratio to equal one. After dispensing the monomer and the initiator dissolved in monomer (0.002 mol/l) the reactor vessel was sealed and heated at 120° C. for 24 h. After the predetermined heating and agitation time the reactor vessels were cooled to room temperature and opened and the polymerization mixtures were worked up and characterized using the standard procedure outlined for polymerization experiments at the beginning of the Example section. Molecular weight and polydispersity index data of the 6-arm star polymers are presented in table 2.

TABLE 2

| Initiator | Initiator to monomer ratio (per arm) | Target Mw | Obsvd. M$_w$* | PDI |
|---|---|---|---|---|
| 12-arm | 1:10,000 | 6 M | 1.1 M | 1.98 |
| 12-arm | 1:5,000 | 3 M | 800k | 1.95 |
| 12-arm | 1:1,000 | 600k | 395k | 1.50 |

*M = millions, k = thousands

Example 2C 2-arm Linear Polymers

Three stable free radical polymerization (SFRP) were carried out under bulk polymerization conditions. Each polymerization was designed to have the following final conditions for the growth of the linear polymer: total volume of 0.4 mL, N,N-dimethylacrylamide as monomer, 0.0002 and 0.001 mole equivalence of initiator to monomer. The 2-arm initiator was based on bisphenol-A where each arm carries an adduct of the initiator/control agent (the organic soluble 2,2,5-trimethyl-3-(1-phenylethoxy)-4-phenyl-3-azahexane). This compound predetermines the control agent to initiator ratio to equal one. After dispensing the monomer and the initiator dissolved in monomer (0.002 mol/l) the reactor vessel was sealed and heated at 120° C. for 24 h. After the predetermined heating and agitation time the reactor vessels were cooled to room temperature and opened and the polymerization mixtures were worked up and characterized using the standard procedure outlined for polymerization experiments at the beginning of the Example section. Molecular weight and polydispersity index data of the 2-arm linear polymers are presented in table 3.

TABLE 3

| Initiator | Initiator to monomer ratio (per arm) | Target Mw | Obs. $M_w$* | PDI |
|---|---|---|---|---|
| 2-arm | 1:5,000 | 1 M | 870k | 1.93 |
| 2-arm | 1:1,000 | 200k | 218k | 1.59 |

M = millions, k = thousands

Example 2D

1-arm Linear Polymers

Three stable free radical polymerization (SFRP) were carried out under bulk polymerization. Each polymerization was designed to have the following final conditions for the growth of the linear polymer: total volume of 0.4 mL, N,N-dimethylacrylamide as monomer, 0.0002 and 0.001 mole equivalence of initiator to monomer. The 1-arm initiator was based on an adduct of the initiator/control agent (the organic soluble 2,2,5-trimethyl-3-(1-phenylethoxy)-4-phenyl-3-azahexane). This compound predetermines the control agent to initiator ratio to equal one. After dispensing the monomer and the initiator dissolved in monomer (0.002 mol/l) the reactor vessel was sealed and heated at 120° C. for 24 h. After the predetermined heating and agitation time the reactor vessels were cooled to room temperature and opened and the polymerization mixtures were worked up and characterized using the standard procedure outlined for polymerization experiments at the beginning of the Example section. Molecular weight and polydispersity index data of the 1-arm linear polymers are presented in table 4.

TABLE 4

| Initiator | Initiator to monomer ratio (per arm) | Target Mw | $M_w$ | PDI |
|---|---|---|---|---|
| 1-arm | 1:5,000 | 200,000 | 390,000 | 1.76 |
| 1-arm | 1:1,000 | 100,000 | 180,000 | 1.55 |

Example 2E

Preparation of Branched Polymer by Post-Polymerization Branching

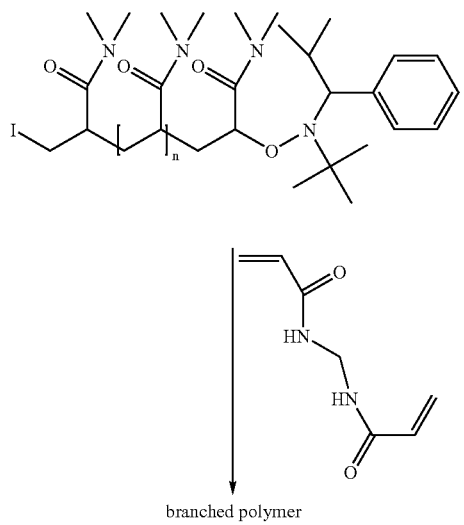

branched polymer

Nine stable free radical polymerization (SFRP) were carried out under aqueous solution polymerization conditions. Each polymerization was designed to have the following final conditions for the growth of the linear polymer: total volume of 0.7 mL, N,N-dimethylacrylamide as monomer (75 volume %), 0.0001, 0.0005 and 0.001 mole equivalence of initiator to monomer. The initiator was based on an adduct of the initiator/control agent (the organic soluble 2,2,5-trimethyl-3-(1-phenylethoxy)-4-phenyl-3-azahexane). This compound predetermines the control agent to initiator ratio to equal one. After dispensing the monomer and the initiator dissolved in monomer (0.002 mol/l) the reactor vessel was sealed and heated at 100° C. for 24 h. After the predetermined heating and agitation time the reactor vessels were cooled to room temperature and opened and 0.00001 and 0.0005 mole equivalents of N,N'-methylenebisacrylamide to monomer were added to the polymerization mixtures and the reactions were heated for an additional 18 h. Work up and characterization was done using the standard procedure outlined for polymerization experiments at the beginning of the Example section. Molecular weight and polydispersity index data of the post-branched polymers are presented in table 5.

TABLE 5

| Initiator | Initiator to monomer ratio (per arm) | Bisacrylamide to monomer | Target Mw | $M_w$ | PDI |
|---|---|---|---|---|---|
| 1-arm | 1:1,000 | 0 | 100,000 | 195,000 | 1.45 |
| 1-arm | 1:1,000 | 1:100,000 | 100,000 | 156,000 | 1.96 |
| 1-arm | 1:1,000 | 1:20,000 | 100,000 | 125,000 | 2.01 |
| 1-arm | 1:2,000 | 0 | 200,000 | 297,000 | 1.58 |
| 1-arm | 1:2,000 | 1:100,000 | 200,000 | 263,000 | 1.80 |
| 1-arm | 1:2,000 | 1:20,000 | 200,000 | 245,000 | 1.95 |
| 1-arm | 1:10,000 | 0 | 1,000,000 | 950,000 | 1.91 |
| 1-arm | 1:10,000 | 1:100,000 | 1,000,000 | 875,000 | 1.95 |
| 1-arm | 1:10,000 | 1:20,000 | 1,000,000 | 820,000 | 2.02 |

Example 2F

Viscosity

Solution viscosity may be estimated by determining the rate at which liquid subjected to a known pressure flows through a tube of known dimensions (Hagen-Poiseuille flow). This is easily measured by a variety of means. For example, two optical emitter-detector pairs may be placed at different locations along the tube and used to detect the passage of the liquid meniscus. From knowledge of the distance separating the detectors, the dimensions of the tube, and the time required for the meniscus to pass from the first to the second detector, the flow rate (Q) may be determined. This is in turn related to the viscosity by $$Q = \frac{\pi R^4 p}{8 \eta L},$$

where R and L are the radius and length of the tube, respectively; p is the pressure drop across the tube; and $\eta$ is the viscosity of the liquid. Although the assumptions involved in deriving this expression are not strictly valid for non-Newtonian liquids such as polymer solutions, such measurements are frequently employed to determine an "effective viscosity" for these materials. In a gravity-driven flow, the pressure is supplied by gravity and is equal to $\rho g h$, where $\rho$ is the density of the fluid, g is 9.8 m/s$^2$, and h is the height of fluid above the entrance to the tube.

Viscosities of polymer solutions were estimated with a capillary viscometer consisting of a 500 μl glass syringe with a Luer hub that was placed in a polyethylene block. Two infrared LEDs were placed at predefined locations on the outside of the block; holes drilled through the block defined a light beam which was interrupted by the passage of the liquid meniscus. A phototransistor which was matched to each LED was placed at the end of the hole and used to detect the light beam. The output of both transistors was conditioned and used to control a millisecond timer.

Repeated measurements on simple liquids of known viscosity were in reasonable agreement with the relation given above. Departures from the expected behavior are due to a number of well-known corrections and will not be reviewed here. (See, for example, C. W. Macosko, *Rheology: Principles, Measurements, and Applications*, Wiley-VCH, 1994) Repeated measurements on polymer solutions yielded flow times comparable in magnitude to those obtained for ethylene glycol, indicating that the viscosity of the former can be estimated from the ratio of flow times. (From the expression above, the flow time, which is inversely proportional to the flow rate Q, is directly proportional to the viscosity.) The following polymers (except for the ethylene glycol standard) are all poly N,N-dimethylacrylamide (PDMA) polymers made with alpha-hydrido nitroxide initiator control agents under controlled polymerization conditions as described herein and then prepared in water at a 10 weight % loading, with the target molecular weight indicated in the below table. For example, the star was made with a 12 arm star dendritic initiator, as described herein. The resulting values are summarized below:

| Material | Flow Time (s) | Viscosity (cps) |
| --- | --- | --- |
| Ethylene glycol | 18.0 | 161 |
| Linear PDMA (195k observed Mw) | 34.5 | 309 |
| Branched PDMA 0.00001% branching (195k observed Mw) | 23.2 | 208 |
| Branched PDMA 0.0005% branching (195k observed Mw) | 19.1 | 171 |
| 12-arm Star PDMA (6 M target Mw, 1 M observed Mw) | 29.0 | ≈250 |

Ramakrishna et al. report viscosities of 1200 cp for linear PDMA of 200 kDa in 6.5 weight % aqueous solution at 30° C.

Example 2G

Static Light Scattering

Static Light Scattering experiments were performed using automated HPLC system Alliance 2690 (Waters), equipped with an evaporative light scattering detector PL-EMD 960 (Polymer Laboratories) for measuring the concentration signal and a triple-angle static light scattering detector MiniDawn (Wyatt Technologies) as a molecular-weight sensitive detector. In the experiment presented, 100 mL of the polymer solution at concentration of about 1 mg/mL was injected into a stream mobile phase (deionized water) at the flow rate of 1 mL/min through a guard column for aqueous SEC. The signals from both static light scattering detector at the three different angles (LS 45°, 90° and 135°) and evaporative light scattering detector (ELSD) were acquired and processed.

It is known that larger molecules scatter more light at low angles than at high angles and the radius of gyration can be calculated from such an angular dependence. By comparing the overlaid light scattering traces at different angles a qualitative estimate of the relative sizes of the polymer molecules was obtained. The trends of the angular dependency of the light scattering signal were about the same for both linear poly-N,N-dimethylacrylamide (PDMA) having a targeted Mw of 1,000,000 (observed $Mw_{SEC}$ of about 1,000,000) and the 12-arm star PDMA having a targeted Mw of 6M—about 500,000 per arm (observed $Mw_{SEC}$ of about 1,300,000). This suggests that the radii of gyration are about the same for the these linear and non-linear polymers.

Figure 7A:
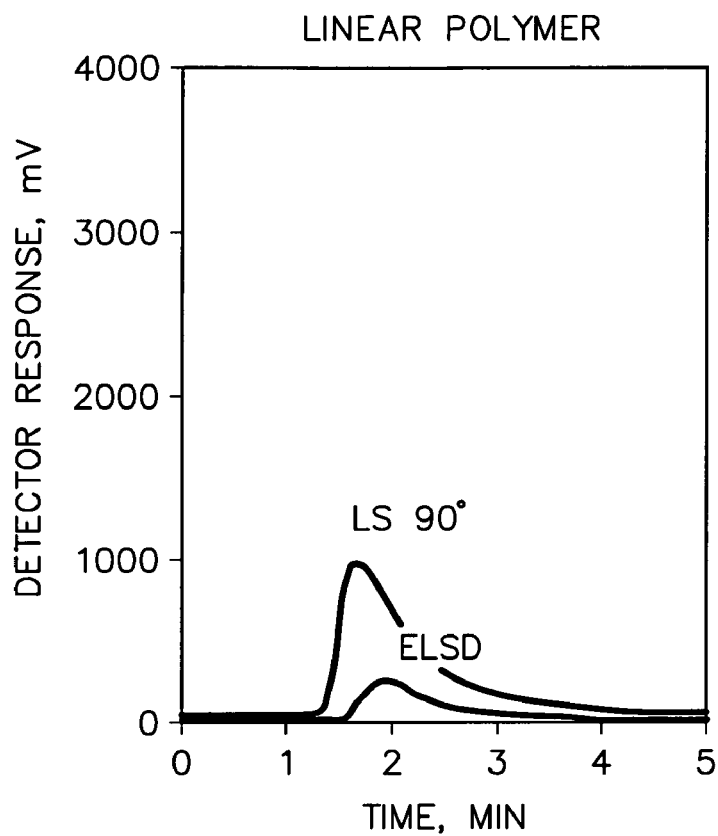
FIGS. 7A and 7B are graphs showing the results of light-scattering and concentration analyses of Example 2G. Detector response (mV) is plotted versus time (min) for comparison of light-scattering signal (90°) (upper trace) to concentration signal (ELSD) (lower trace) for both a linear polymer (FIG. 7A) and a twelve-arm star polymer (FIG. 7B), each of which had a target molecular weight of 500,000 daltons.
Figure 7B:
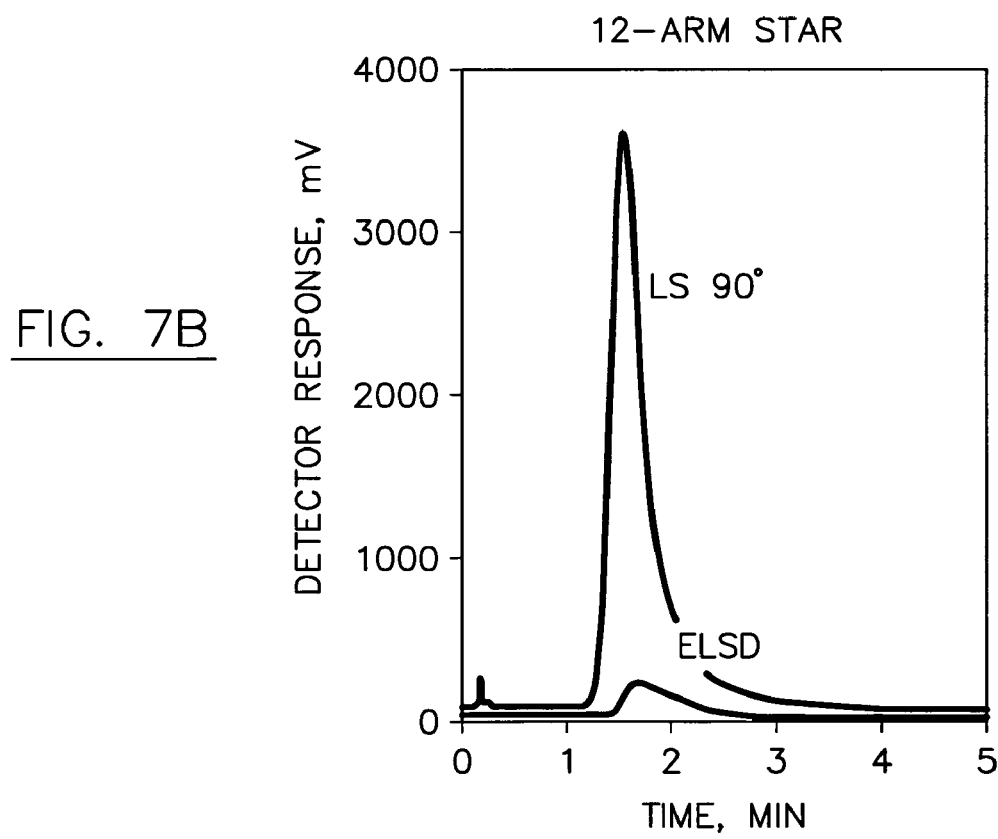

FIGS. 7A and 7B show the light scattering traces at the 90° angle (LS 90°) overlaid with the concentration signal (ELSD). It is known that the ratio of the light scattering and the concentration signals correlates well to the actual molecular weight where that the concentration increment of the refractive index (dn/dc) remains constant. Based on the assumption that the dn/dc value is substantially independent of polymer architecture, the traces in FIG. 7 were consistent with the observation that the molecular weight of the polymer with a star-like architecture is significantly larger than that of the linear polymer.

In light of the qualitative comparison, it was concluded that the star polymer constitutes a molecule of a higher mass concentrated in the same molecular volume as the linear polymer.

Example 2H

Use of Marcomonomers for Hyper-Branched Structures

The synthesis of the starting compound (2,2,5-Trimethyl-3-(1-(4'-chloromethyl)phenylethoxy)-4-phenyl-3-azahexane) has been described by Hawker et al., (*J. Am. Chem. Soc.*, 121, 3904-3920 (1999), which is incorporated herein by reference). As shown in FIG. 3A, this molecule was then modified. This chlorine derivative (2 g, 5.3 mmol) is treated by potassium acetate (1.2 g, 12.2 mmol) in 10 ml of Hexamethyl phosphotriamide (HMPT). The mixture is then allowed to react at room temperature for three days. The crude product is purified by extraction in a mixture water/dichloromethane followed by a chromatographic column using dichloromethane as eluant. Yield 90%.

This initiator is used for the synthesis of poly(dimethylacrylamide) macromonomers according to the scheme shown in FIG. 3B. The acetoxy-alkoxyamine is used to initiate a controlled free radical polymerization of dimethyl acrylamide at 125 C (16 h). Typically, for a 10,000 g/mol targeted, a mixture of 200 mg of this acetoxy initiator, of 6 mg of 2,2,5-trimethyl-4-phenyl-3-azahexane-3-nitroxide, and 5 g of freshly distilled dimethylacrylamide are degassed by three/thaw cycles in a schlenk tube. The reaction mixture was heated at 125 C under argon for 16 hours. The viscous reaction mixture is then dissolved in dichloromethane and purified by precipitation in hexanes. The polymer is then dried under vacuum to remove all the solvents.

To the obtained polymer dissolved in ethanol (2 g of polymer, 10,000 g/mol, in 10 ml of solvent) is added an aqueous solution of potassium hydroxide (0.015 g/ml) (2 equivalent of potassium hydroxide permole of acetoxy group). The mixture is heated at reflux for 3 hours. The polymer is then purified by several precipitations into hexanes to give an α-hydroxy poly (dimethylacrylamide). $^1$H NMR shows a disappearance of the signal at 5.2 ppm from the initial ester protecting group (CO—O—CH$_2$—). The obtained α-hydroxy polydimethylacrylamide is thoroughly dried by lyophilization to insure to remaining trace of water.

To a mixture maintained at 0° C. of the hydroxy derivative polymer (1 g, 0.1 mmol) dissolved in dry THF (2-4 ml), 40 ul of acryloyl chloride were added (5 equivalents per mole of hydroxy group). A mixture of triethylamine (48 mg) and dimethylaminopyrridine (6 mg) in dry THF (2 ml) is gradually added on the mixture. The reaction mixture was stirred for an additional period of 1 h and allowed to warm to room temperature. Salts were removed by filtration. The polymer is then purified by several careful precipitations in hexanes.

These macromonomers are prepared with different molecular weights. For examples, the typical characteristics of these structures are summarized in the table 6 below:

TABLE 6

|  | A | B | C |
|---|---|---|---|
| Mw (g/mol) | 8500 | 26000 | 46300 |
| Polydispersity | 1.13 | 1.12 | 1.13 |

Figure 3C:
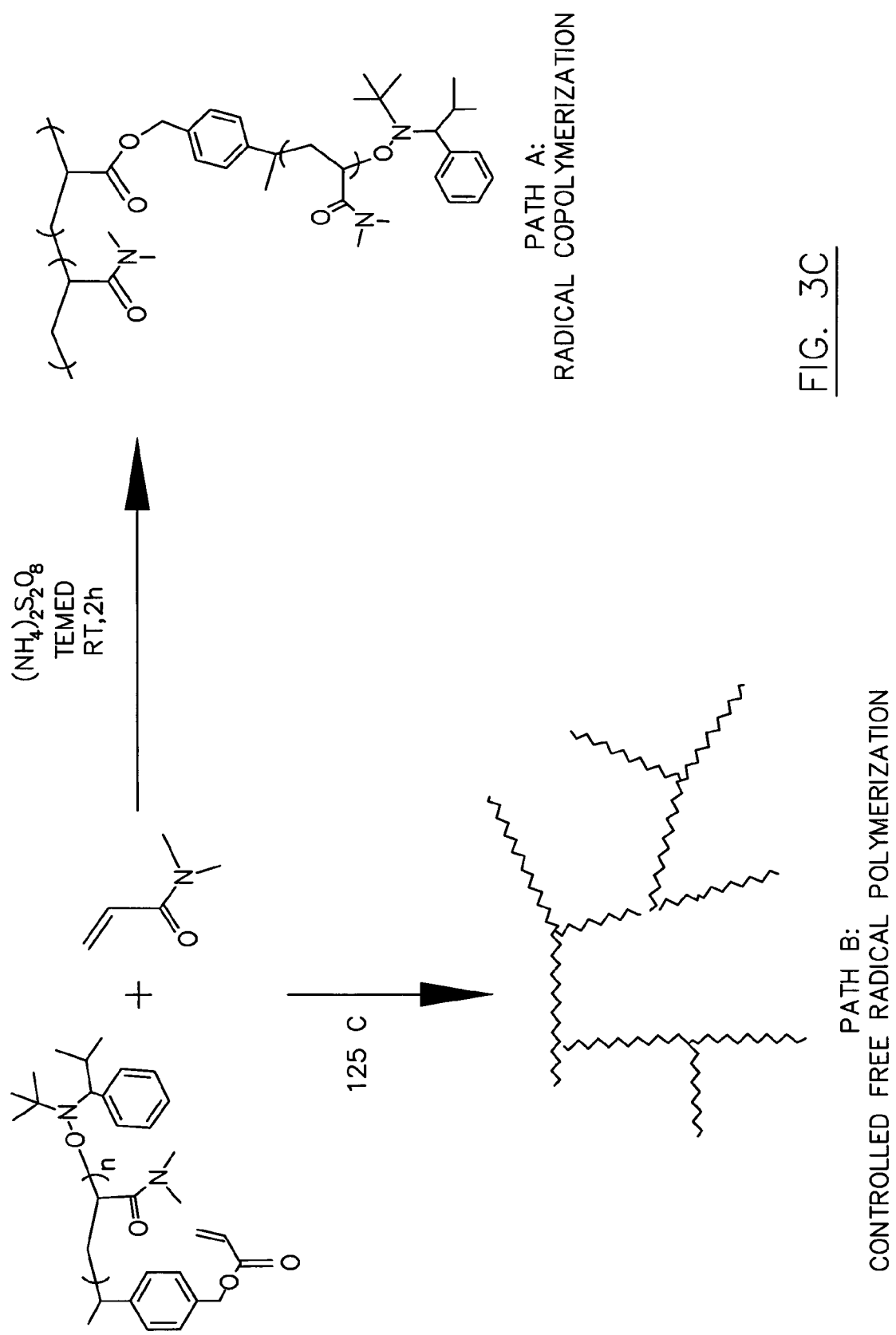

The macromonomers prepared are used both as comonomers and as initiators in a radical polymerization (controlled or not) in two different paths according to the scheme shown if FIG. 3C. In path A, a free radical polymerization is carried forming a branched polymer by mixing macromonomer and non-macromonomer. Path B refers to the use of macromonomers as macroinitiators in the monomer mixture (macromonomer+monomer): the control is provided by the structure of the macromonomers, which are alkoxyamines. The resulting material is an hyper-branched structure. The polymerizations using these macromonomers also use N,N dimethylacrylamide as monomer and are initiated by a redox system comprising ammonium persulfate and N,N,N',N'-tetramethylethylene diamine at room temperature. After a couple of hours, the reaction is found to be very viscous and the resulting polymers are analyzed by gel permeation chromatography.

Example 3

Capillary Gel Electrophoresis

Example 3A

Polymer Loading Effect on Capillary Electrophoresis

Capillary electrophoresis was carried out using ABI PRISM 310 Genetic Analyser instrument from the Perkin-Elmer (PE) Applied Biosystems equipped with a laser-based fluorescence detector measuring a response at four different wavelengths.

Briefly, both cathodic and anodic reservoirs were filled with the 3700 Running Buffer with EDTA from the PE Applied Biosystems, and a fused silica capillary, having 61 cm length and 50 μm i.d., was connected to the system. The capillary was filled with a polymer solution using a syringe pump of the electrophoretic system prior the injection. Then, the DNA mixture diluted in the running buffer was electrokinetically injected into the capillary by applying 2.5 kV for 30 seconds. The electrophoresis was performed at 50° C. by applying 12.2 kV for 120 minutes. The DNA sequencing ladder from pGEM template contained fragments of up to about 3,000 base pairs derivatized with four different fluorescence dyes. The detector output traces at all of the four different wavelength as produced by the instrument were collected by the data acquisition software from PE Applied Biosystems.

A qualitative evaluation of the raw electrophoretic data was done by identifying four characteristic landscape features of the sequence ladder profile that correlated with an estimated number of base pairs, bp (FIG. 8) by comparison with the raw data and the analyzed sequencing data using a commercially available polymer separation medium (POP6, Perkin-Elmer). Three separate regions were identified in each raw electrophoreogram (160 bp-330 bp, 330 bp-500 bp, and 500 bp-700 bp).

Figure 8:
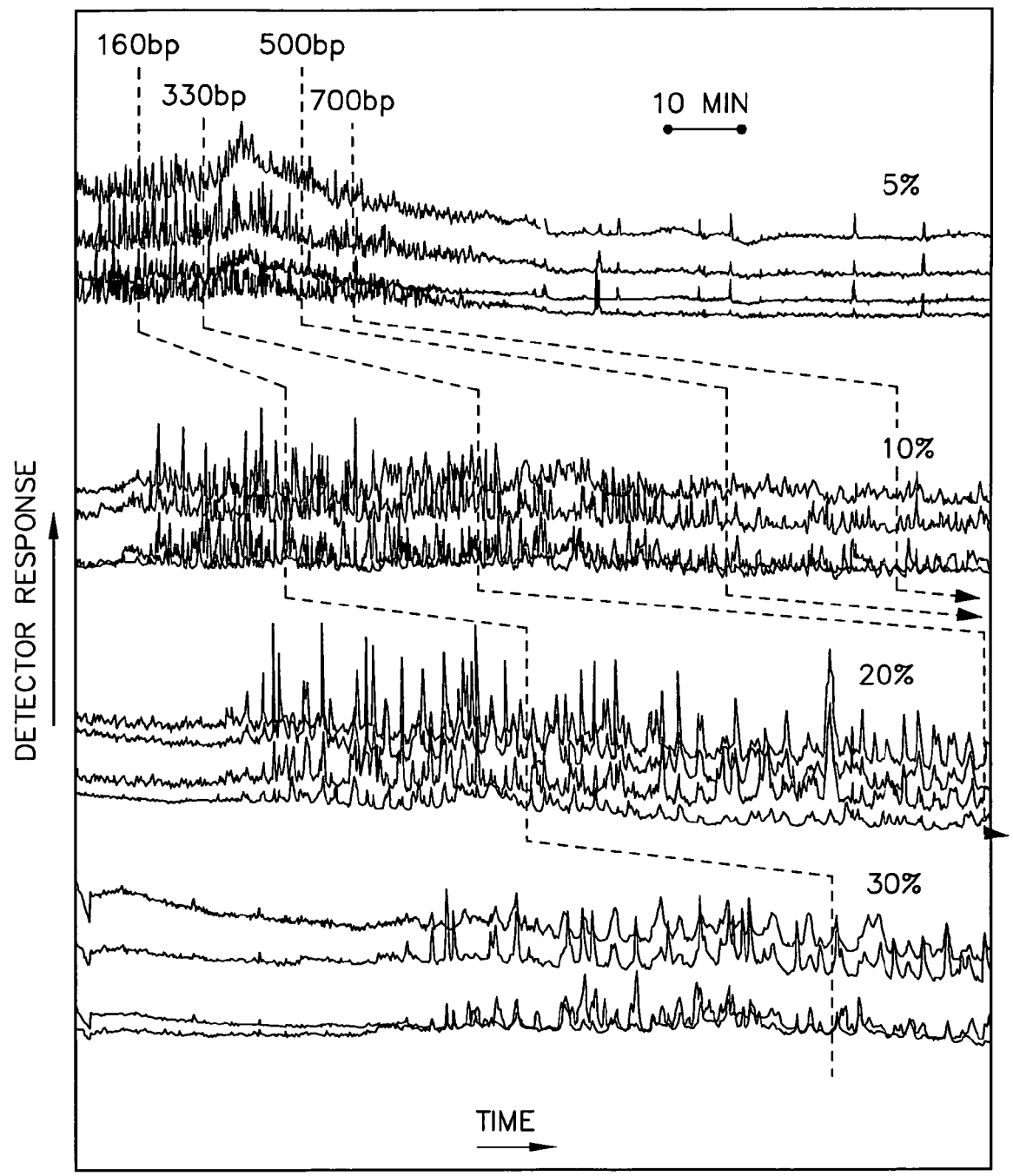
FIG. 8 is a graph showing the effect of polymer loading on DNA separation based on experiments of Example 3A. Detector response (mV) is plotted versus time (minutes) for a various separation media comprising a twelve-arm star polymer (poly N,N-dimethylacrylamide) with a weight-average molecular weight of 1.3M at different concentrations (5%, 10%, 20% and 30%). The four traces represent the response for the four types of labeled DNA bases (A, G, C, T).

FIG. 8 demostrates the controlled separation performance of the system with four different loadings of the 12-arm star polymer. The polymer was dissolved in the 3700 Running Buffer with EDTA from the PE Applied Biosystems at various weight concentrations. At 5 weight % loading of the 12-arm star polymer (PDMA) having an observed Mw$_{SEC}$ of 1.3M, the majority of the DNA fragments migrated through the polymer solution within about 45 minutes and about 700 basepairs were identified. At 10 weight % loading, the majority of the DNA fragments passed through the detector in about 2 hours and about 700 base pairs were identified. At 20 weight %, the first DNA fragments were detected only about 20 minutes after injection and after 2 h about 300 base pairs were identified. At 30 weight %, no DNA fragments were detected for the first 40 minutes and after 2 h about 160 basepairs were identified. These results suggested that the peaks were resolved better at higher polymer loadings; however, a substantial portion of the largest DNA fragments did not migrate into the detector in the time range of the measurement.

Example 3B

Capillary Electrophoresis with Blended-Polymer Separation Medium

Capillary electrophoresis was carried out using the same instrumentation and procedure as those described in the previous example.

The raw electrophoretic data was qualitatively evaluated by identifying the characteristic landscape features of the sequence ladder profile in the same way as described in the previous example. In addition, the average resolution was calculated as a ratio of the distance between two identified fragments, divided by the difference in the numbers of their base pairs, and their average peak width.

Figure 9:
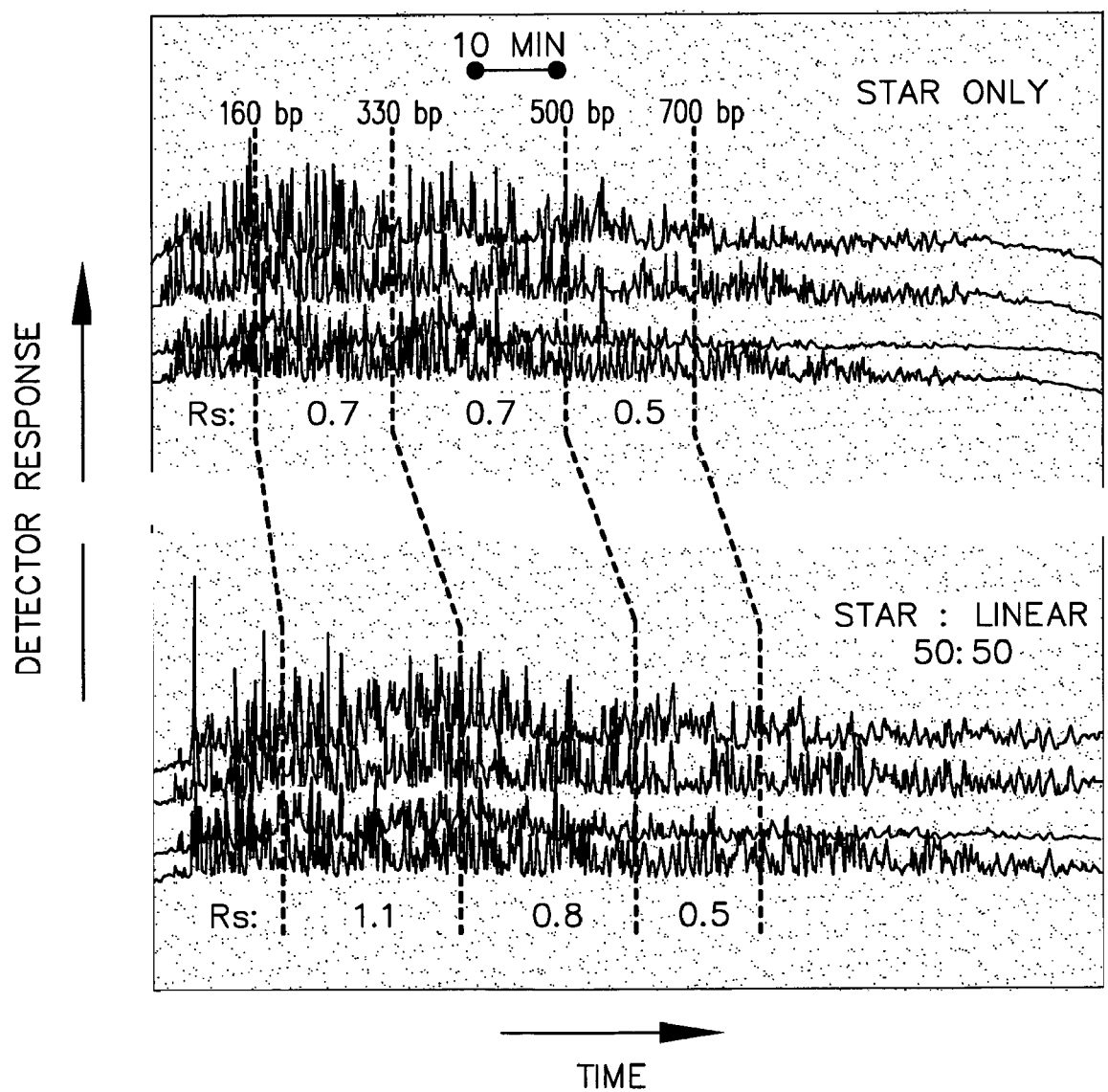
FIG. 9 is a graph showing the effect of polymer blending on DNA separation based on experiments of Example 3B. Detector response (mV) is plotted versus time (minutes) for two separation media comprising (i) a twelve-arm star polymer (poly N,N-dimethylacrylamide) having weight-average molecular weight of 1.5M at 10% polymer concentration—alone (top set of traces) or (ii) a 50:50 blend of a twelve-arm star polymer (poly N,N-dimethylacrylamide) and a linear polymer (poly N,N-dimethylacrylamide) having weight-average molecular weights of 1.5M and 1 M respectively (bottom set of traces) at 10% total polymer loading. The four traces (in each of the upper and lower sets) represent the response for the four types of labeled DNA bases (A, G, C, T). "Rs" relates to the relative resolution.

Blending of polymers with narrow polydispersities, and/or different molecular weight, and/or different architectures could be advantageous in terms of addressing the separation of different size DNA fragments within one sample. Therefore, a 12-arm star polymer having an observed $Mw_{SEC}$ of 1.5M (targeted Mw of 12M) was dissolved in the 3700 Running Buffer with EDTA from the PE Applied Biosystems at 10 weight % and tested as described in the previous example. For comparison, a 50:50 blend comprising a 12-arm star polymer having an observed $Mw_{SEC}$ of 1.5M and a linear polymer having an observed $Mw_{SEC}$ of 1.1 M was prepared with a total polymer concentration of 10 weight %. This blend was analyzed in the manner mentioned above. Three separate regions were identified in each raw electrophoreogram (160 bp-330 bp, 330 bp-500 bp, and 500 bp-700 bp) and the average resolution was estimated as mentioned above for each section. The results of these experiments including the resolution values are shown in FIG. 9. These data suggested that the addition of the linear polymer enhanced the separation of the shorter DNA fragments without deteriorating the resolution of the longer DNA fragments.

In light of the detailed description of the invention and the examples presented above, it can be appreciated that the several objects of the invention are achieved. The explanations and illustrations presented herein are intended to acquaint others skilled in the art with the invention, its principles, and its practical application. Those skilled in the art may adapt and apply the invention in its numerous forms, as may be best suited to the requirements of a particular use. Accordingly, the specific embodiments of the present invention as set forth are not intended as being exhaustive or limiting of the invention.

What is claimed is:

1. A non-linear polymer comprising repeat units having the formula:

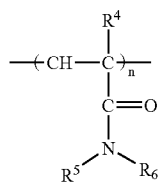

where $R^4$ is H or an alkyl group; and $R^5$ and $R^6$, independently, are selected from the group consisting of hydrogen, alkyl, substituted alkyl, cycloalkyl, substituted cycloalkyl, heteroalkyl, heterocycloalkyl, substituted heterocycloalkyl, aryl, substituted aryl, heteroaryl, substituted heteroaxyl, alkoxy, aryloxy, and combinations thereof; and n is 10 or more; and wherein the polymer includes at least a fragment of a material having the formula

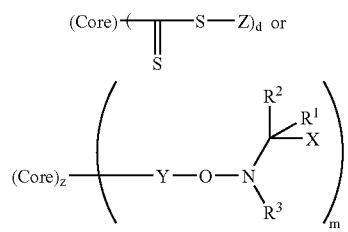

wherein Core is a core molecule, S is sulfur, Z is selected front the group consisting of amino and alkoxy, each of $R^1$, $R^2$ and $R^3$ are the same or different straight chain, branched or cyclic substituted or unsubstituted alkyl groups, X is a moiety that is capable of destabilizing a free radical, d is 2 or more, m ranges from about 2 to about 100, and z is 1 or more.

2. A polymer according to claim 1 wherein said polymer consists essentially of said units.

3. A polymer according to claim 1 wherein said polymer is a copolymer.

4. A polymer according to claim 1 wherein said polymer is a block copolymer.

5. A polymer according to claim 1 wherein said polymer is a random copolymer.

6. A polymer according to claim 1 wherein said polymer has a star architecture, with a weight average molecular weight of greater that 75,000 daltons and an aqueous solution containing about 5% w/v of said polymer has a viscosity of less than about 600 cpa.

7. A polymer comprising repeat units derived from monomers having the formula T or I':

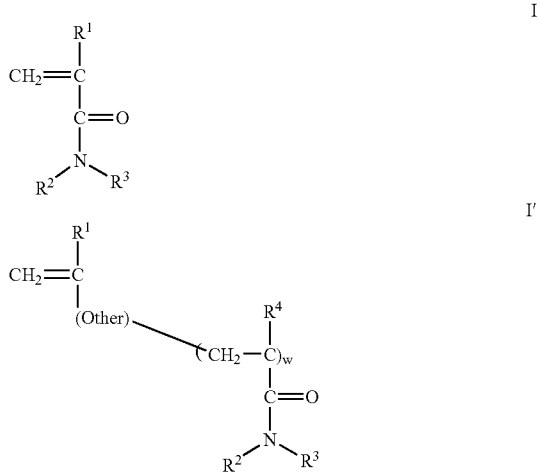

where $R^1$ is selected from the group consisting of hydrogen or alkyl; and $R^2$ and $R^2$ independently, are selected from the group consisting of hydrogen, alkyl, substituted alkyl, cycloalkyl, substituted cycloalkyl, heteroalkyl, heterocycloalkyl, substituted heterocycloalkyl, aryl, substituted aryl, heteroaryl, substituted heteroaryl, alkoxy, aryloxy, and combinations thereof; w is a number up to 1000; and Other is a linker and contains up to 20 non-hydrogen atoms; and wherein the polymer includes at least a fragment of a material having the formula

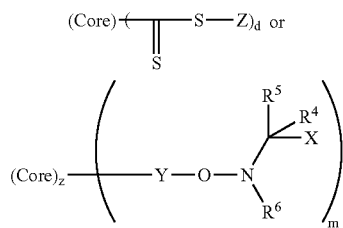

wherein Core is a core molecule, S is sulfur, Z is selected from the group consisting of amino and alkoxy, each of $R^4$, $R^5$ and $R^6$ are the same or different straight chain, branched or cyclic substituted or unsubstituted alkyl group, X is a moiety that is capable of destabilizing a free radical, d is 2 or more, m ranges from about 2 to about 100, and z is 1 or more.

8. The polymer of claim 7, wherein the polymer is a block copolymer.

9. The polymer of claim 7, wherein the polymer is linear.

10. The polymer of claim 7, wherein the polymer is a graft copolymer.

11. The polymer of claim 7, wherein the polydispersity index is not more than about 1.8.

12. The polymer of claim 7, wherein the polydispersity index is not more than about 1.5.

13. The polymer of claim 7, wherein the polymer has a weight average molecular weight of at least 500,000.

14. The polymer of claim 7, wherein the polymer has a weight average molecular weight of at least 500,000.

15. The polymer of claim 7, wherein the polymer has a weight average molecular weight of at least 1,000,000.

16. The polymer of claim 7, wherein the polymer has a low critical solubility temperature of at least about 80° C.

17. The polymer of claim 7, wherein the polymer has a low critical solubility temperature of at least about 90° C.

18. A polymer according to claim 1, wherein the polymer has a polydispersity index no greater than 2.0.

19. A polymer according to claim 1, wherein said polymer is soluble or dispersible in water or in aqueous medium, and has a weight average molecular weight of at least about 75,000.

20. A polymer according to claim 7, wherein said polymer is soluble or dispersible in water or in aqueous medium, and has a weight average molecular weight of at least about 75,000.

* * * * *

UNITED STATES PATENT AND TRADEMARK OFFICE
CERTIFICATE OF CORRECTION

PATENT NO. : 7,259,217 B2 Page 1 of 1
APPLICATION NO. : 10/775672
DATED : August 21, 2007
INVENTOR(S) : Klaerner et al.

It is certified that error appears in the above-identified patent and that said Letters Patent is hereby corrected as shown below:

Column 64, claim 1, line 6: "heteroaxyl," should read
-- heteroaryl, --.

Column 64, claim 6, line. 41: "cpa." should read -- cps. --.

Column 64, claim 7, line 44: "formula T or I':" should read
-- formula I or I': --.

Column 64, claim 7, line 67: "$R^2$ and $R^2$" should read
-- $R^2$ and $R^3$ --.

Column 66, claim 13, line 9: "at least 500,000." should read
-- at least 300,000. --.

Signed and Sealed this

Sixteenth Day of September, 2008

JON W. DUDAS
*Director of the United States Patent and Trademark Office*